US008710046B2

(12) United States Patent
Guzzo et al.

(10) Patent No.: US 8,710,046 B2
(45) Date of Patent: Apr. 29, 2014

(54) 5-$HT_3$ RECEPTOR MODULATORS, METHODS OF MAKING, AND USE THEREOF

(75) Inventors: Peter R. Guzzo, Niskayuna, NY (US); David D. Manning, Duanesburg, NY (US); William Earley, East Greenbush, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 13/384,050

(22) PCT Filed: Jun. 30, 2010

(86) PCT No.: PCT/US2010/040617
§ 371 (c)(1),
(2), (4) Date: Feb. 10, 2012

(87) PCT Pub. No.: WO2011/008572
PCT Pub. Date: Jan. 20, 2011

(65) Prior Publication Data
US 2012/0270857 A1    Oct. 25, 2012

Related U.S. Application Data

(60) Provisional application No. 61/225,368, filed on Jul. 14, 2009.

(51) Int. Cl.
*C07D 487/04*    (2006.01)
*C07D 403/04*    (2006.01)
*A61K 31/5517*   (2006.01)
*A61P 25/00*     (2006.01)

(52) U.S. Cl.
USPC ...... 514/212.06; 514/220; 514/293; 514/305; 540/460; 540/496; 540/498; 540/520; 546/82

(58) Field of Classification Search
USPC ............ 514/212.06, 220, 293, 305; 540/460, 540/496, 498, 520; 546/82
See application file for complete search history.

(56) References Cited

U.S. PATENT DOCUMENTS

| | | | |
|---|---|---|---|
| 3,642,821 A | 2/1972 | Hester | |
| 3,734,919 A | 5/1973 | Hester | |
| 6,552,017 B1 | 4/2003 | Robichaud et al. | |
| 6,743,785 B2 | 6/2004 | Al-Awar et al. | |
| 7,307,094 B2 | 12/2007 | Fairfax et al. | |
| 7,553,846 B2 | 6/2009 | Yang et al. | |
| 7,863,271 B2 | 1/2011 | Yang et al. | |
| 2009/0298809 A1 | 12/2009 | Manning et al. | |

FOREIGN PATENT DOCUMENTS

| | | |
|---|---|---|
| WO | 00/77002 A1 | 12/2000 |
| WO | 2006005613 A1 | 1/2006 |
| WO | 2007/011820 A2 | 1/2007 |
| WO | 2007/019078 A2 | 2/2007 |
| WO | 2008/019363 A2 | 2/2008 |
| WO | 2008/086404 A1 | 7/2008 |
| WO | 2009/155054 A2 | 12/2009 |

OTHER PUBLICATIONS

Examination Report for New Zealand Patent Application No. 597613 (Oct. 3, 2012).
International Search Report for PCT/US2010/040617 (Apr. 12, 2011).
International Written Opinion for PCT/US2010/040617 (Apr. 12, 2011).
CAS Registry No. 67465-18-3 (Dec. 1990).
CAS Registry No. 28740-86-5 (Dec. 1990).
Hester et al., "Pyrrolo[3,2,1-jk][1,4]Benzodiazepines and Pyrrolo[1,2,3-ef][1,5]Benzodiazepines Which Have Central Nervous System Activity," J. of Med. Chem., 13(5):827-35 (1970).
Supplemental European Search Report and Written Opinion for Application No. 10800312.0, dated Dec. 19, 2012.
Translation of Office Action dated Jun. 11, 2013 for Mexican Patent Application No. MX/a/2012/000572 (redacted).
Office Action for Chinese Application 201080041834.7 dated Dec. 4, 2013.
Office Action for Mexican Application MX/a/2012/000572 dated Dec. 17, 2013 (redacted).
Sui Hong et al., "Research and Application of Subtypes, Regulators, and Antagonists of 5-HT3 Receptors," Foreign Medical Sciences, Section of Pathophysiology and Clinical Medicine 2(25):179-182 (2005).

*Primary Examiner* — Bruck Kifle
(74) *Attorney, Agent, or Firm* — LeClairRyan, a Professional Corporation

(57) ABSTRACT

Novel 5-$HT_3$ receptor modulators are disclosed. These compounds are used in the treatment of various disorders, including chemotherapy-induced nausea and vomiting, post-operative nausea and vomiting, and irritable bowel syndrome. Methods of making these compounds are also described in the present invention.

44 Claims, No Drawings

5-HT₃ RECEPTOR MODULATORS, METHODS OF MAKING, AND USE THEREOF

This application is a national stage application under 35 U.S.C. 371 of PCT Application No. PCT/US2010/040617, filed Jun. 30, 2010, which claims the priority benefit of U.S. Provisional Patent Application Ser. No. 61/225,368, filed Jul. 14, 2009, which is hereby incorporated by reference in its entirety.

FIELD OF THE INVENTION

The present invention relates to serotonin type-3 (5-HT$_3$) receptor modulators, compositions, their use in the treatment of diseases in which the 5-HT$_3$ receptor is implicated, for example, in the treatment of Irritable Bowel Syndrome (IBS), chemotherapy-induced nausea and vomiting (CINV), and post-operative nausea and vomiting (PONV), and the use of the compounds in combination therapy.

BACKGROUND OF THE INVENTION

Irritable Bowel Syndrome (IBS) has a major impact on the healthcare system in that IBS management in the U.S. is estimated to cost 8 billion dollars annually in direct medical care costs and as high as 25 billion dollars in indirect economic costs.

Compounds which alter the activity of certain serotonin receptors have shown benefit for the symptomatic treatment of IBS. To that end, the only U.S. drug in this class is alosetron, a serotonin type-3 (5-HT$_3$) receptor antagonist. Shortly following its introduction in 2000, alosetron was withdrawn from the market due to instances of ischemic colitis occurring in IBS patients. Later, the drug was reinstated by the FDA because the demand by patients was so great for a treatment for IBS. In 2002, the US Food and Drug Administration approved alosetron hydrochloride (LOTRONEX®) tablets under restricted conditions for patients in whom the medical benefits outweigh the risks.

Ramosetron, a 5-HT$_3$ receptor antagonist originally developed and marketed for emesis associated with cancer therapy, was approved in Japan for the treatment of IBS. Since its introduction in 2008 no reports of ischemic colitis have appeared.

5-HT$_3$ receptor modulators with improved safety profiles are therefore highly desired for the treatment of IBS. A 5-HT$_3$ receptor modulator is an agent which can either inhibit (e.g., an antagonist) or partially activate (e.g., a partial agonist) the 5-HT$_3$ receptor.

Nausea and vomiting caused by chemotherapy remain among the most distressing side effects for patients undergoing treatment for cancer. Depending upon the chemotherapy agents or regimens given, up to 90% of patients may suffer from some form of chemotherapy-induced nausea and vomiting (CINV). Symptoms from CINV can be severely debilitating and often result in patients refusing further courses of chemotherapy, with obviously unfavorable consequences as regards to progression of the cancer. Furthermore, CINV is burdensome on the medical system, consuming time from the healthcare staff, who could otherwise attend to other patients or medical issues.

CINV is divided into two main categories: acute CINV and delayed CINV. Acute CINV occurs within the first 24 hours of treatment; delayed CINV occurs from 24 hours to 120 hours following treatment. Delayed CINV remains a highly under treated side effect in patients undergoing chemotherapy, as healthcare providers tend to underestimate the number of patients who suffer from delayed CINV. Furthermore, delayed CINV greatly impairs patients' ability to provide care to themselves once they have been discharged.

Compounds that target 5-HT$_3$ receptors are effective antiemetics; they constitute the single greatest advance in the management of nausea and vomiting in patients with cancer. Blocking the 5-HT$_3$ receptor signal in the CNS or periphery appears to prevent acute emesis. 5-HT$_3$ receptor modulators are approved to prevent acute CINV. Palonosetron is also approved for the prevention of delayed CINV. In addition, the combination of the neurokinin antagonist aprepitant (EMEND®), a 5-HT$_3$ receptor modulator, and the corticosteroid dexamethasone has been shown to be highly effective in preventing both acute and delayed cisplatin-induced emesis.

Palonosetron has received approval for the treatment of post operative nausea and vomiting (PONV). Therefore, 5-HT$_3$ receptor modulators may be useful for the treatment of PONV.

Clearly, there is a need for improved therapy for IBS, CINV, and PONV. The present invention is directed to achieving this objective.

SUMMARY OF THE INVENTION

The present invention relates to a compound of formula I:

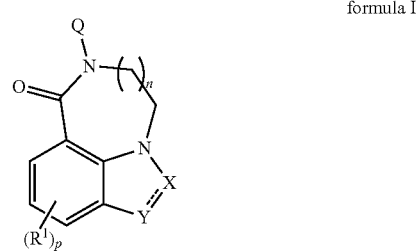

formula I wherein:
------ represents an optional double bond;
Q is a saturated, bicyclic, heterocyclic amine, wherein the saturated, bicyclic, heterocyclic amine comprises at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, and —NR$^7$R$^8$;
X is CH, CH$_2$, CR$^2$, C(R$^2$)$_2$, N, NH, C=O, or SO$_2$;
Y is CH, CH$_2$, CR$^2$, C(R$^2$)$_2$, N, NH, NR$^3$, O, or C=O;
R$^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^2$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^2$R$^8$;
R$^2$ is individually selected at each location from the group consisting of H, halogen, —OR$^4$, —NR$^4$R$^5$, —NR$^4$C(O)R$^5$, —NR⁴C(O)₂R⁵, —NR⁵C(O)NR⁵R⁶, —S(O)$_q$R⁵, —CN, —C(O)R⁵, —C(O)NR⁴R⁵, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —NR⁷R⁸, and phenyl which is optionally substituted 1-3 times with halogen, $C_1$-$C_4$ alkyl, $C_1$-$C_4$ haloalkyl, $C_1$-$C_4$ alkoxy, —CN, —OR⁷, or —NR⁷R⁸;

R³ is selected from the group consisting of H, $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —NR⁷R⁸, and phenyl which is optionally substituted 1-3 times with halogen, $C_1$-$C_4$ alkyl, $C_1$-$C_4$ haloalkyl, $C_1$-$C_4$ alkoxy, —CN, —OR⁷, or —NR⁷R⁸;

R⁴ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R⁶, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R⁵ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R⁴ and R⁵ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

R⁶ is $C_1$-$C_4$ alkyl, $C_1$-$C_4$ haloalkyl, or phenyl;

R⁷ and R⁸ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R⁶, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;

p is 0, 1, 2, or 3; and q is 0, 1, or 2;

or an oxide thereof, a pharmaceutically acceptable salt thereof, a solvate thereof, or prodrug thereof.

Another aspect of the present invention relates to a compound of formula II:

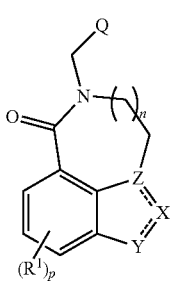

formula II wherein: ˉˉˉˉˉ represents an optional double bond;

Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, and —NR⁷R⁸;

X is CH, CH₂, CR², C(R²)₂, N, NH, C═O, or SO₂;

Y is CH, CH₂, CR², C(R²)₂, N, NH, NR³, O, or C═O;

Z is C or N;

R¹ is individually selected at each location from the group consisting of H, halogen, —OR⁴, —NR⁴R⁵, —NR⁴C(O)R⁵, —NR⁴C(O)₂R⁵, —NR⁵C(O)NR⁵R⁶, —S(O)$_q$R⁵, —CN, —C(O)R⁵, —C(O)NR⁴R⁵, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —NR⁷R⁸, and phenyl which is optionally substituted 1-3 times with halogen, $C_1$-$C_4$ alkyl, $C_1$-$C_4$ haloalkyl, $C_1$-$C_4$ alkoxy, —CN, —OR⁷, or —NR⁷R⁸;

R² is individually selected at each location from the group consisting of H, halogen, —OR⁴, —NR⁴R⁵, —NR⁴C(O)R⁵, —NR⁴C(O)₂R⁵, —NR⁵C(O)NR⁵R⁶, —S(O)$_q$R⁵, —CN, —C(O)R⁵, —C(O)NR⁴R⁵, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —NR⁷R⁸, and phenyl which is optionally substituted 1-3 times with halogen, $C_1$-$C_4$ alkyl, $C_1$-$C_4$ haloalkyl, $C_1$-$C_4$ alkoxy, —CN, —OR⁷, or —NR⁷R⁸;

R³ is selected from the group consisting of H, $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR⁷, —NR⁷R⁸, and phenyl which is optionally substituted 1-3 times with halogen, $C_1$-$C_4$ alkyl, $C_1$-$C_4$ haloalkyl, $C_1$-$C_4$ alkoxy, —CN, —OR⁷, or —NR⁷R⁸;

R⁴ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R⁶, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R⁵ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R⁴ and R⁵ are taken together with the nitrogen to which they are attached to form a five to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

R⁶ is $C_1$-$C_4$ alkyl, $C_1$-$C_4$ haloalkyl, or phenyl;

R⁷ and R⁸ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, C$_1$-C$_4$ alkyl, C$_1$-C$_4$ haloalkyl, and C$_1$-C$_4$ alkoxy;

n is 0, 1, or 2, with the provisos that: (1) when Z is N, then n is 1 or 2; and (2) when Z is C, then n is 0, 1, or 2;

p is 0, 1, 2, or 3; and q is 0, 1, or 2;

or an oxide thereof, a pharmaceutically acceptable salt thereof, a solvate thereof, or prodrug thereof.

The present invention also relates to a method of treating a disease or condition which is susceptible to treatment with a 5-HT$_3$ receptor modulator. This method involves selecting a patient with a disease or condition which is susceptible to treatment with a 5-HT$_3$ receptor modulator and administering to the patient a therapeutically effective amount of a compound of formula I or II or a pharmaceutically acceptable salt thereof.

A further aspect of the present invention relates to methods of making the compounds of the present invention.

It has now been found that compounds of formulae I and II are 5-HT$_3$ receptor modulators. This invention provides compounds that bind to the serotonin type-3 (5-HT$_3$) receptor with high affinity. This activity is consistent with the effects of other reported 5-HT$_3$ receptor modulators, several of which have been approved to treat human disease including IBS (e.g. alosetron, ramosetron), CINV (e.g. ondansetron, palonsetron, granisetron), and PONV (palonosetron). The compounds provided by formula I and II are useful for the treatment of irritable bowel syndrome, nausea, emesis (vomiting), and other disorders described herein. The 5-HT$_3$ receptor modulators of the present invention may treat a range of IBS symptoms (e.g. IBS-D, IBS-M and IBS-C).

DETAILED DESCRIPTION OF THE INVENTION

The present invention relates to a compound of formula I:

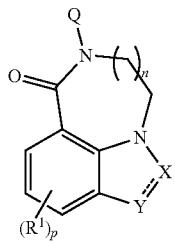

formula I wherein:

------ represents an optional double bond; and

Q is a saturated, bicyclic, heterocyclic amine, wherein the saturated, bicyclic, heterocyclic amine comprises at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of C$_1$-C$_3$ alkyl, halogen, —CN, —OR$^7$, and —NR$^7$R$^8$;

X is CH, CH$_2$, CR$^2$, C(R$^2$)$_2$, N, NH, C=O, or SO$_2$;

Y is CH, CH$_2$, CR$^2$, C(R$^2$)$_2$, N, NH, NR$^3$, O, or C=O;

R$^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl, and heteroaryl is optionally substituted with from 1 to 3 substituents independently selected at each occurrence thereof from C$_1$-C$_3$ alkyl, halogen, —CN, —OR$^7$, —NR$^7$R$^8$, and phenyl which is optionally substituted 1-3 times with halogen, C$_1$-C$_4$ alkyl, C$_1$-C$_4$ haloalkyl, C$_1$-C$_4$ alkoxy, —CN, —OR$^7$, or —NR$^7$R$^8$;

R$^2$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl, and heteroaryl, wherein each of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl, and heteroaryl is optionally substituted with from 1 to 3 substituents independently selected at each occurrence thereof from C$_1$-C$_3$ alkyl, halogen, —CN, —OR$^7$, —NR$^7$R$^8$, and phenyl which is optionally substituted 1-3 times with halogen, C$_1$-C$_4$ alkyl, C$_1$-C$_4$ haloalkyl, C$_1$-C$_4$ alkoxy, —CN, —OR$^7$, or —NR$^7$R$^8$;

R$^3$ is selected from the group consisting of H, C$_1$-C$_6$ alkyl, C$_3$-C$_6$ alkenyl, C$_3$-C$_6$ alkynyl; C$_3$-C$_6$ cycloalkyl, C$_4$-C$_7$ cycloalkylalkyl, aryl, and heteroaryl, wherein each of C$_1$-C$_6$ alkyl, C$_3$-C$_6$ alkenyl; C$_3$-C$_6$ alkynyl, C$_3$-C$_6$ cycloalkyl, C$_4$-C$_7$ cycloalkylalkyl, aryl, and heteroaryl is optionally substituted with from 1 to 3 substituents independently selected at each occurrence thereof from C$_1$-C$_3$ alkyl, halogen, —CN, —NR$^7$R$^8$, and phenyl which is optionally substituted 1-3 times with halogen, C$_1$-C$_4$ alkyl, C$_1$-C$_4$ haloalkyl, C$_1$-C$_4$ alkoxy, —CN, —OR$^7$, or —NR$^7$R$^8$;

R$^4$ is H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, —C(O)R$^6$, phenyl, or benzyl, wherein phenyl or benzyl is optionally substituted 1 to 3 times with halogen, cyano, C$_1$-C$_4$ alkyl, C$_1$-C$_4$ haloalkyl, or C$_1$-C$_4$ alkoxy;

R$^5$ is H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, phenyl, or benzyl, wherein phenyl or benzyl is optionally substituted 1 to 3 times with halogen, cyano, C$_1$-C$_4$ alkyl, C$_1$-C$_4$ haloalkyl, or C$_1$-C$_4$ alkoxy; or R$^4$ and R$^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, C$_1$-C$_4$ alkyl, C$_1$-C$_4$ haloalkyl, and C$_1$-C$_4$ alkoxy;

R$^6$ is C$_1$-C$_4$ alkyl, C$_1$-C$_4$ haloalkyl, or phenyl;

R$^7$ and R$^8$ are each independently H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, C$_1$-C$_4$ alkyl, C$_1$-C$_4$ haloalkyl, and C$_1$-C$_4$ alkoxy;

n is 1 or 2;

p is 0, 1, 2, or 3; and q is 0, 1, or 2;

or an oxide thereof, a pharmaceutically acceptable salt thereof, a solvate thereof, or prodrug thereof.

Another aspect of the present invention relates to a compound of formula II:

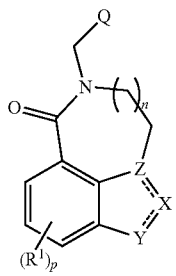

formula II wherein:
▭▭▭▭▭ represents an optional double bond; and
Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, and —$NR^7R^8$;
X is CH, $CH_2$, $CR^2$, $C(R^2)_2$, N, NH, C=O, or $SO_2$;
Y is CH, $CH_2$, $CR^2$, $C(R^2)_2$, N, NH, $NR^3$, O, or C=O;
Z is C or N;
$R^1$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^2$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^3$ is selected from the group consisting of H, $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;
$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;
$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or
$R^4$ and $R^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;
$R^6$ is $C_1$-$C_4$ alkyl, $C_1$-$C_4$ haloalkyl, or phenyl;
$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;
n is 0, 1, or 2, with the provisos that: (1) when Z is N, then n is 1 or 2; and (2) when Z is C, then n is 0, 1, or 2;
p is 0, 1, 2, or 3; and
q is 0, 1, or 2;
or an oxide thereof, a pharmaceutically acceptable salt thereof, a solvate thereof, or prodrug thereof.

As used above, and throughout the description of the invention, the following terms, unless otherwise indicated, shall be understood to have the following meanings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multi-cyclic ring system of 6 to about 14 carbon atoms, preferably of 6 to about 10 carbon atoms, and includes arylalkyl groups. Representative aryl groups include phenyl and naphthyl.

The term "heteroaryl" means an aromatic monocyclic or multi-cyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring.

The term "cycloalkyl" means a non-aromatic mono- or multi-cyclic ring system of about 3 to about 7 carbon atoms, preferably of about 5 to about 7 carbon atoms. Exemplary monocyclic cycloalkyls include cyclopentyl, cyclohexyl, cycloheptyl, and the like.

The term "cycloalkylalkyl" means an cycloalkyl-alkyl-group in which the cycloalkyl and alkyl are as defined herein. Exemplary cycloalkylalkyl groups include cyclopropylmethyl and cyclopentylmethyl.

Arylalkyl means an alkyl residue attached to an aryl ring. Examples are benzyl, phenethyl, and the like. Attachment can be through the alkyl or aryl.

The term "haloalkyl" means both branched and straight-chain alkyl substituted with one or more halogen, wherein the alkyl group is as herein described.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "halogen" means fluorine, chlorine, bromine, or iodine.

The term "compounds of the invention", and equivalent expressions, are meant to embrace compounds of general formula I or II as hereinbefore described, which expression includes the prodrugs, the pharmaceutically acceptable salts, the oxides, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "method of treating" means amelioration or relief from the symptoms and/or effects associated with the disorders described herein.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound of formula I or II in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy,* 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. Since the compounds of formulae I and II contain a basic nitrogen, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The abbreviations Me, Et, and Ph represent methyl, ethyl, and phenyl, respectively. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations," is incorporated herein by reference in its entirety.

The term "therapeutically effective amount" is meant to describe an amount of compound of the present invention effective in modulating 5-$HT_3$ activity and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

The term "pharmaceutical composition" means a composition comprising a compound of formula I or II and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs," p. 113-191 (1991); Advanced Drug Delivery Reviews, H. Bundgard, 8, p. 1-38 (1992); *Journal of Pharmaceutical Sciences*, 77:285 (1988); Nakeya et al, *Chem. Pharm. Bull.*, 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The present invention relates to compounds of formulae I and II, wherein Q is a substituted or unsubstituted bicyclic, heterocyclic amine. In accordance with the present invention, the bicyclic, heterocyclic amines are saturated and contain at least one nitrogen in the ring. They may contain additional nitrogens, as well as other heteroatoms, such as oxygen and sulfur. In one embodiment of the present invention, the compounds of formula I or II include at least 2 atoms, preferably from 2 to 5 and preferably carbon atoms, connecting the amide nitrogen to any nitrogen in the amine group Q.

In one embodiment, Q of formula I or II is a bicyclic amine of empirical formula $C_{7-10}N_{1-2}$. In another embodiment of the present invention, Q is an azabicycloheptane, azabicyclooctane, or azabicyclononane. Suitable heterocyclic amines include, but are not limited to, quinuclidine, tropane, azabicyclo[3.3.1]nonane, methyl azabicyclo[3.3.1]nonane, 9-azabicyclo[3.3.1]nonan-3-one, 3,9-dimethyl-3,9-diazabicyclo[3.3.1]nonane, 3,9-diazabicyclo[3.3.1]nonane, 3-oxa-9-azabicyclo[3.3.1]nonane, 3-thia-9-azabicyclo[3.3.1]nonane, 9-methyl-3,9-diazabicyclo[3.3.1]nonane, 3-methyl-3,9-diazabicyclo[3.3.1]nonane, 3-oxa-9-azabicyclo[3.3.1]nonane, 3-thia-9-azabicyclo[3.3.1]nonane, and azabicyclo[3.2.2]nonane.

In one embodiment of the present invention, the saturated, bicyclic, heterocyclic amine (i.e., Q) is attached to the amide nitrogen of the tricyclic core of formula I or II (through the methylene unit in formula II) in the (S) configuration. In another embodiment of the present invention, the saturated, bicyclic, heterocyclic amine (i.e., Q) is attached to the amide nitrogen of the tricyclic core of formula I or II (through the methylene unit in formula II) in the (R) configuration. In yet another embodiment, Q is substituted and is, itself, chiral. Another embodiment of the present invention is a mixture of stereoisomeric compounds of formula I or II.

In another embodiment of the present invention, Q is a saturated, bicyclic, heterocyclic amine or methyl-substituted saturated, bicyclic, heterocyclic amine, in which the nitrogen is tertiary. In one embodiment, Q is selected from the group consisting of:

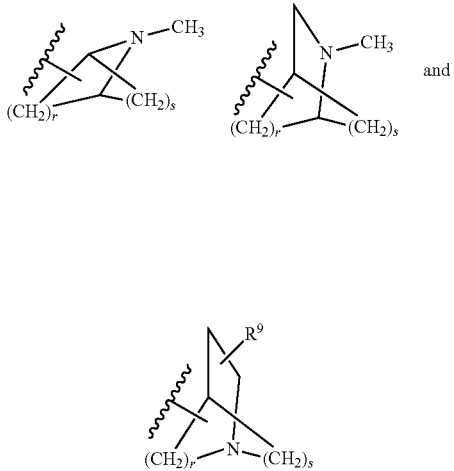

wherein r=1, 2, 3, or 4; s=0, 1, 2, 3, or 4; and $R^9$ is hydrogen or methyl. In these figures, the Q group is connected to the tricyclic core structure through any carbon ring member (i.e., not a terminal N-methyl).

Other suitable heterocyclic amines include:

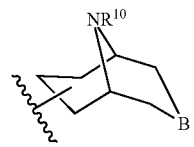

wherein $R^{10}$ is hydrogen or $C_1$-$C_3$ alkyl and B is NH, $NCH_3$, O, S, SO, or $SO_2$.

One embodiment of the present invention is the compound of formula I or II, wherein X is CH. In another embodiment of the present invention X is N. In yet another embodiment X is C=O. In another embodiment X is $SO_2$. In yet another embodiment, X is $CR^2$.

In one embodiment, Y is N or NH. In another embodiment, Y is CH or $CR^2$, wherein $R^2$ is alkyl.

In another embodiment, Z is C. In a further embodiment, Z is N.

In yet another embodiment, $R^2$ is substituted phenyl. In yet another embodiment, $R^2$ is 4-fluorophenyl. In a further embodiment, at least one of $R^1$ is H or Cl.

In yet another embodiment, $R^4$ and $R^5$ combine with the nitrogen to which they are attached to form a 5- to 7-membered heterocyclic ring structure having from 1 to 3 heteroatoms. Suitable heteroatoms include nitrogen, oxygen, and sulfur. In one embodiment, the 5- to 7-membered heterocyclic ring structure is selected from the group consisting of piperidine, pyrrolidine, piperazine, N-methylpiperazine, morpholine, thiomorpholine, [1,2]oxazinane, isoxazolidine, and 2-oxo-2H-pyridine.

With regard to compounds of formulae I and II, examples of —X—Y— include:

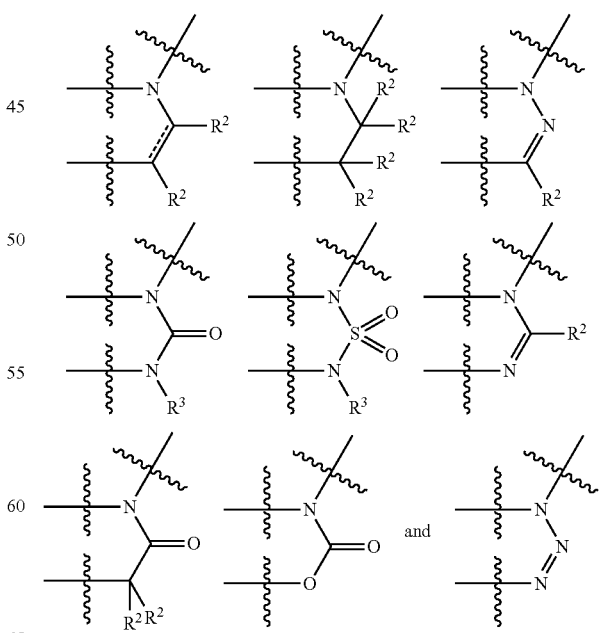

With regard to compounds of formula II, examples of —X—Y— also include:

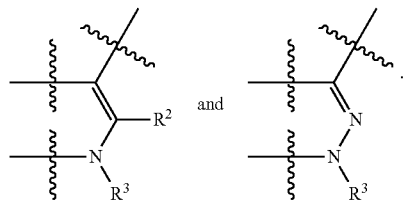

Suitable aryl groups for the substituents of the present invention are selected from the group consisting of phenyl, benzyl, naphthyl, indanyl, and indenyl. Suitable heteroaryl groups for the substituents of the present invention are selected from the group consisting of pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

Within these embodiments, the selection of a particular preferred substituent at any one of Q, X, Y, Z, and $R^1$ through $R^8$ does not affect the selection of a substituent at any of the others of Q, X, Y, Z, and $R^1$ through $R^8$. That is, preferred compounds provided herein have any of the preferred substituents at any of the positions.

In one embodiment of the present invention, the compound of formula I is selected from the group consisting of:

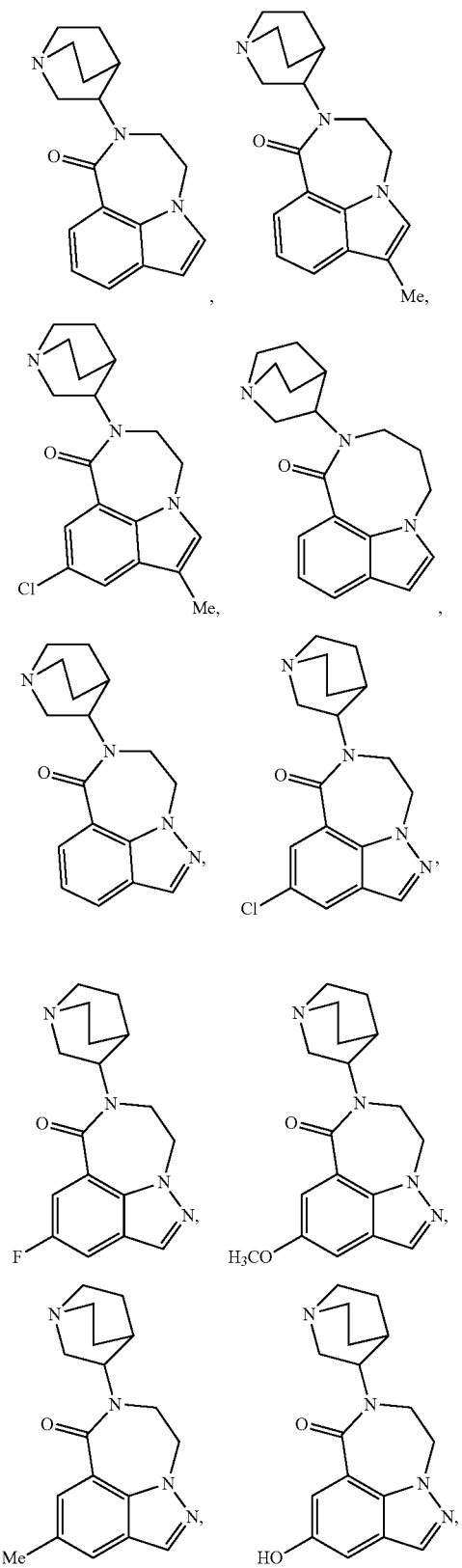

-continued

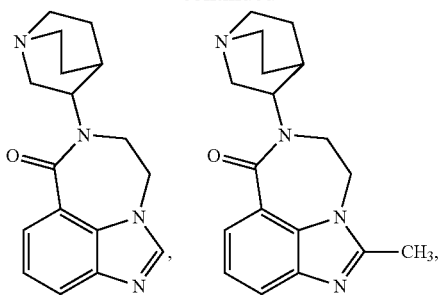

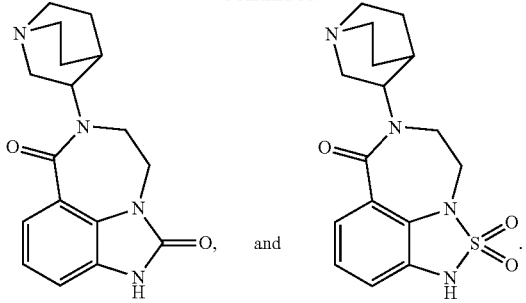

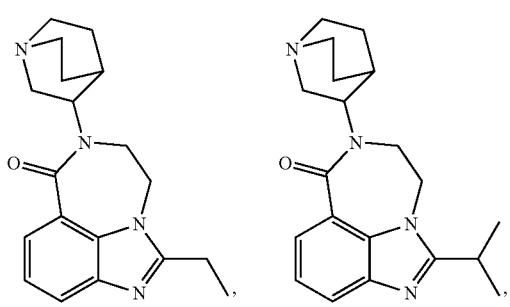

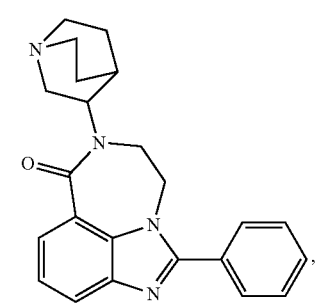

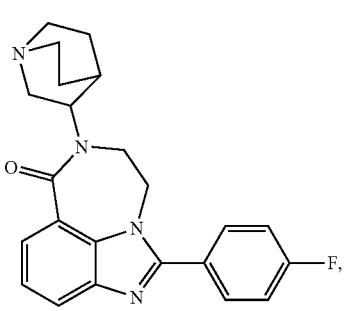

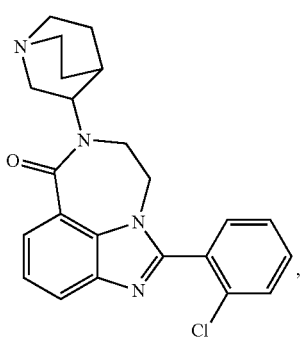

In another embodiment, the compound of formula II is selected from the group consisting of:

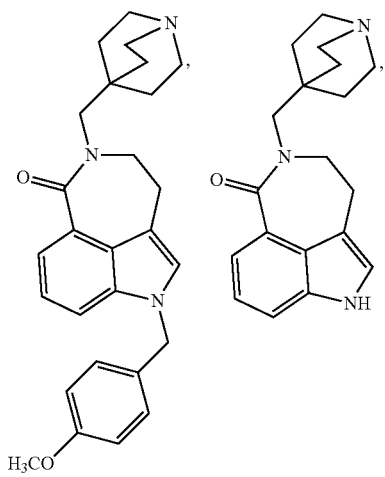

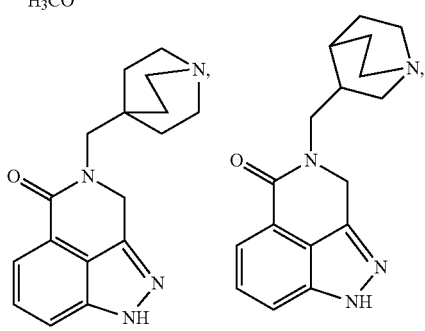

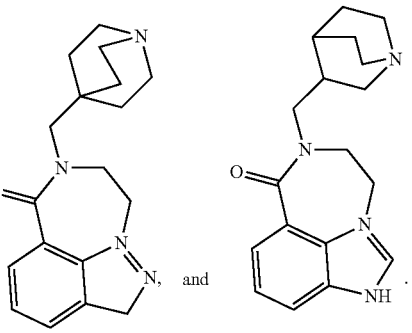

One embodiment of the present invention relates to pharmaceutically acceptable salts, or non-salt forms, of any of the compounds of formula I or II described herein.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula I or II, wherein one or more of the atoms, e.g., C or H, are replaced by the corresponding radioactive isotopes of that atom (e.g., C replaced by $^{14}C$ and H replaced by $^{3}H$), or a stable isotope of that atom (e.g., C replaced by $^{13}C$ or H replaced by $^{2}H$). Radioisotopes of hydrogen, carbon, phosphorous, fluorine, iodine and chlorine include $^{3}H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to bind to neurotransmitter proteins. In addition, in the case of stable isotopes, such compounds may have the potential to favorably modify the biological properties, e.g., pharmacological and/or pharmacokinetic properties, of compounds of formulae I and II. The details concerning selection of suitable sites for incorporating radioactive isotopes into the compounds are known to those skilled in the art.

Compounds of the present invention as described herein are useful as 5-HT$_3$ receptor modulators. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all compounds of formula I or II, except those that are in the public's possession.

While it may be possible for compounds of formula I or II to be administered as the raw chemical, it will often be preferable to present them as part of a pharmaceutical composition. Accordingly, another aspect of the present invention is a pharmaceutical composition containing a therapeutically effective amount of a compound of formula I or II, or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

In one embodiment of the present invention, the pharmaceutical composition further comprises one or more other therapeutic ingredients, e.g., other compounds effective in the treatment of IBS, CINV or PONV, that are known to persons of skill in the art. Such other therapeutic agents are described below.

Another aspect of the present invention relates to a method of treating a disease or condition which is susceptible to treatment with a 5-HT$_3$ receptor modulator. This method involves selecting a patient with a disease or condition which is susceptible to treatment with a 5-HT$_3$ receptor modulator and administering to the patient a therapeutically effective amount of a compound of formula I or II or a pharmaceutically acceptable salt thereof.

Diseases or conditions which are susceptible to treatment with a 5-HT$_3$ receptor modulator in accordance with the present invention include, but are not limited to, general anxiety disorders, social phobias, vertigo, obsessive-compulsive disorders, panic disorders, post-traumatic stress disorders, bulimia nervosa, drug withdrawal effects, alcohol dependency, pain (including visceral pain), sleep related central apneas, chronic fatigue syndrome, Parkinson's Disease Psychosis, schizophrenia, cognitive decline and defects in schizophrenia, Parkinson's Disease, Huntington's Chorea, presenile dementias, Alzheimer's Disease, psychological disorders, obesity, substance abuse disorders, dementia associated with neurodegenerative disease, cognition deficits, fibromyalgia syndrome (see US. Patent Application Publication No 2004/0204467, which is hereby incorporated by reference in its entirety), rosacea (see PCT Publication No. WO 2007/138233, which is hereby incorporated by reference in its entirety), cardiovascular disorders mediated by serotonin, chemotherapy induced nausea and vomiting (CINV), post-operative induced nausea and vomiting (PONV), radiation induced nausea and vomiting (RINV), gastrointestinal disorders (e.g. of the esophagus, stomach and both large and small intestines), including irritable bowel syndrome (IBS) and gastroesophageal reflux disease (GERD) (see European Patent No. EP0430190, U.S. Pat. No. 6,967,207, and U.S. Pat. No. 5,352,685, which are hereby incorporated by reference in their entirety), bronchial asthma, pruritus, migraine (see Costall et al., *Current Drug Targets—CNS & Neurological Disorders*, 3:27-37 (2004) and Israili, *Current Med. Chem.— CNS Agents*, 1:171-199 (2001), which are hereby incorporated by reference in their entirety), and epilepsy (see PCT Publication No. WO 2007/010275, which is hereby incorporated by reference in its entirety).

As described above, the compounds of the present invention are useful as 5-HT$_3$ modulators. A 5-HT$_3$ receptor modulator is an agent which can either inhibit (e.g., an antagonist) or partially activate (e.g., a partial agonist) the 5-HT$_3$ receptor. A 5-HT$_3$ receptor modulator which is a partial agonist can bind the 5-HT$_3$ receptor but only results in partial efficacy relative to a full receptor agonist. Modulators which are partial agonists may be considered ligands which display both agonistic and antagonistic effects depending upon the level of serotonin (endogenous 5-HT$_3$ agonist). For example, when both full agonist (e.g. serotonin) and partial agonist are present, the partial agonist acts as a competitive antagonist, competing with the full agonist for receptor occupancy and producing a net decrease in the receptor activation observed with the full agonist alone (Williams et al., *Principles and Practice of Pharmacology for Anaesthetists*, 4$^{th}$ Ed., Calvey et al., eds., Blackwell Science Asia Pty Ltd., Carlton South, Vic (2001), which is hereby incorporated by reference in its entirety). Clinically, partial agonists can activate receptors to give a desired submaximal response when inadequate amounts of the endogenous ligand are present or they can reduce the overstimulation of receptors when excess amounts of endogenous ligand are present (Zhu, *Biomed. Pharmacother.* 59(3):76-89 (2005), which is hereby incorporated by reference in its entirety).

Thus, in one embodiment of the present invention, the compound of formula I or II or pharmaceutically acceptable salt thereof is a 5-HT$_3$ receptor antagonist.

In another embodiment of the present invention, the compound of formula I or II or pharmaceutically acceptable salt thereof is a 5-HT₃ receptor partial agonist, which may result in a net increase or a net decrease in activation of the 5-HT₃ receptor in the patient.

In another embodiment of the present invention, the above method further involves administering a therapeutically effective amount of one or more schizophrenia or Parkinson's Disease adjuncts. Suitable schizophrenia adjuncts include, but are not limited to, valproate and levomepromazine. Suitable Parkinson's Disease adjuncts include, but are not limited to, transdermal rotigotine, rotigotine and/or rasagiline as a levodopa adjuncts, levodopa, carbidopa, dopamine agonists (bromocriptine, pramipexole, or ropinirole), COMT inhibitors (entacapone or tolcapone), MAO-B inhibitors (rasagiline or selegiline), amantadine, anticholinergic agents (benztropine or trihexyphenidyl), and salfinamide. The compositions may additionally comprise alprazolam, haloperidol, chlorpromazine, risperidone, paliperidone, olanzapine, ziprasidone, quetiapine, clozapine, lithium carbonate, diazepam, carbamazepine, selective serotonin re-uptake inhibitors (SSRI's) (ZOLOFT® or CELEXA®) or tricyclic antidepressants, such as PAMELOR®.

A further aspect of the present invention relates to a method of treating irritable bowel syndrome (IBS). This method involves selecting a patient with IBS and administering to the patient a therapeutically effective amount of a compound of formula I or II or a pharmaceutically acceptable salt thereof.

In another embodiment of the present invention, the above method further involves administering a therapeutically effective amount of other serotonin 5-HT₃ receptor modulators and/or serotonin 5-HT₄ receptor modulators, some of which are indicated below. Suitable other serotonin 5-HT₃ receptor modulators and/or serotonin 5-HT₄ receptor modulators include, but are not limited to, Alosetron (LOTRONEX®), renzapride, cilansetron, Tegaserod (ZELNORM®), Prucalopride, and ondansetron.

In a further embodiment of the present invention, the above method further involves administering a therapeutically effective amount of a therapeutic agent selected from the group consisting of somatostatin analogs such as Octreotide; muscarinic receptor antagonists such as Darifenacin, and Zamifenacin; laxatives such as methylcellulose (CITRUCEL®), Psyllium (METAMUCIL®, FIBERALL®, REGULOID®, KONSYL®), malt soup extract, polyacrylic resins (e.g., hydrophilic forms such as polycarbophil and calcium polycarbophil), plantago seeds, dioctyl calcium sulfosuccinate, dioctyl potassium sulfosuccinate, dioctyl sodium sulfosuccinate, mineral oil, magnesium citrate, magnesium hydroxide, magnesium sulfate, dibasic sodium phosphate, monobasic sodium phosphate, sodium biphosphate, glycerin, anthraquinones or anthracene laxatives (such as aloe, cascara sagrada, danthron, senna, aloin, casanthranol, frangula, and rhubarb), diphenylmethanes (such as bisacodyl and phenolphthalein), and castor oil and the like; antispasmodics, such as the anticholinergic agents dicyclomine HCl (BENTYL®), hyoscyamine sufate (LEVSIN®), and the like; antidepressants such as imipramine (TOFRANIL®), amitriptylin (ELAVIL®); antidiarrheal agents such as diphenoxylate HCl+atropine sulfate (LOMOTIL®), loperamide (IMODIUM®), natural or synthetic opiates (such as difenoxin, diphenoxylate, pargoric, opium tincture, and loperamide), anticholinergics (such as belladonna alkoloids-atropine hyoscyamine, and hyosine), acetyltannic acid, albumin tannate, alkofanone, aluminum salicylates, catechin, lidamidine, mebiquine, trillium, and uzarin, and the like; prokinetic agents, peripheral opiate narcotic antagonists such as fedotozine, trimebutine, and the like. Suitable prokinetic agents include, but are not limited to, cisapride monohydrate (PROPULSID®), metoclopromide, domperidone, and the like.

Another aspect of the present invention relates to a method of treating emesis. This method involves selecting a patient with emesis and administering to the patient a therapeutically effective amount of a compound of formula I or II or a pharmaceutically acceptable salt thereof.

In another embodiment of the present invention, the above method further involves administering a therapeutically effective amount of one, or more other anti-emetic compounds. Suitable anti-emetic compounds include, but are not limited to, alosetron, alprazolam, aprepitant, dexamethasone, dimenhydrinate, diphenhydramine, dolasetron, tetrahydrocannabinol, nabilone, dronabinol, droperidol, granisetron, haloperidol, lorazepam, metoclopramide, midazolam, olanzapine, ondansetron, palonosetron, proclorperazine, promethazine, and tropisetron.

Yet another aspect of the present invention relates to a method of treating CNS diseases or conditions. This method involves selecting a patient with a CNS disease or condition and administering to the patient an effective amount of a compound of formula I or II or a pharmaceutically acceptable salt thereof. Suitable CNS diseases or conditions include, but are not limited to, schizophrenia and Parkinson's disease. Beneficial effects of 5-HT₃ modulators have been reported in clinical studies of Parkinson's disease (Zoldan J et al., *Advances in Neurology*, 69:541-544 (1996), which is hereby incorporated by reference in its entirety) and schizophrenia (Zhang-Jin et al., *Schizophrenia Research*, 88: 102-110 (2006); Alder et al., *Am. J. Psychiatry*, 162:386-388 (2005), which are hereby incorporated by reference in their entirety). Brain responses in humans have been altered upon treatment with alosetron in IBS patients (Mayer et al., *Aliment Pharmacol. Ther.*, 16:1357-1366 (2002), which is hereby incorporated by reference in its entirety). A 5-HT₃ modulator may be used as an adjunct or in combination with another medication.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Another aspect of the present invention relates to a process of preparing a product compound of formula Ia:

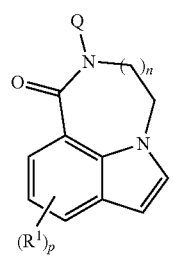

formula Ia

This process involves treating a first intermediate compound of formula III:

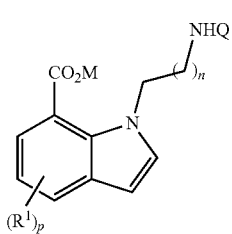

formula III wherein M is H or a counterion, under amide bond formation conditions effective to produce the product compound. Q and $R^1$ are as defined above and additional substituents on the indole are as defined for formula I.

A further aspect of the present invention relates to a process of preparing a product compound of formula Ib:

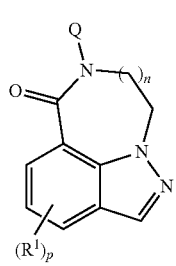

formula Ib

This process involves treating a first intermediate compound of formula IV:

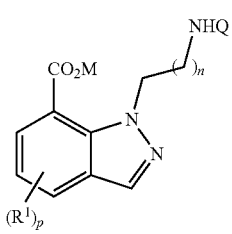

formula IV wherein M is H or a counterion, under amide bond formation conditions effective to produce the product compound. Q and $R^1$ are as defined above and additional substituents on the indazole are as defined for formula I.

A further aspect of the present invention relates to a process of preparing a product compound of Ic:

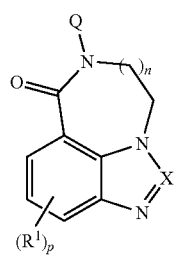

formula Ic

This process involves treating a first intermediate compound of formula V:

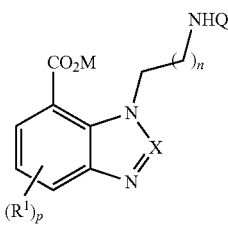

formula V wherein M is H or a counterion, under amide bond formation conditions effective to produce the product compound. Q, X, and $R^1$ are as defined above.

Another aspect of the present invention relates to a process of preparing a product compound of formula IIa:

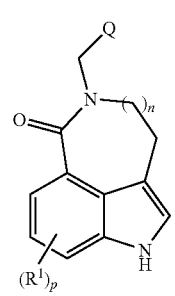

formula IIa

This process involves treating a first intermediate compound of formula VI:

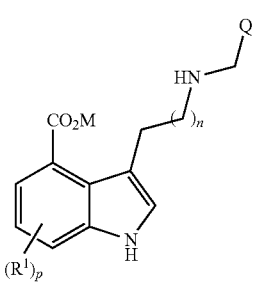

formula VI wherein M is H or a counterion, under amide bond formation conditions effective to produce the product compound. Q and $R^1$ are as defined above and additional substituents on the indole are as defined for formula II.

A further aspect of the present invention relates to a process of preparing a product compound of formula IIb:

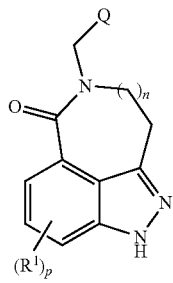

formula IIb

This process involves treating a first intermediate compound of formula VII:

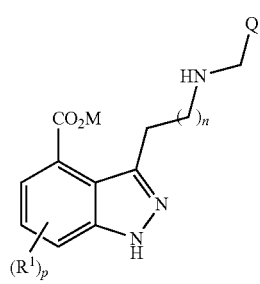

formula VII wherein M is H or a counterion, under amide bond formation conditions effective to produce the product compound. Q and $R^1$ are as defined above and additional substituents on the indazole are as defined for formula II.

A further aspect of the present invention relates to a process of preparing a product compound of formula IIc:

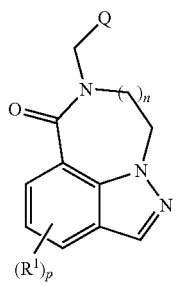

formula IIc

This process involves treating a first intermediate compound of formula VIII:

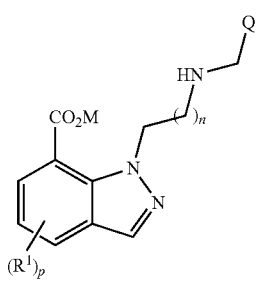

formula VIII wherein M is H or a counterion, under amide bond formation conditions effective to produce the product compound. Q and $R^1$ are as defined above and additional substituents on the indazole are as defined for formula II.

Suitable counterions include, but are not limited to, $Li^+$ and $Na^+$.

The methods of synthesis of the present invention involve standard amide bond formation conditions that are familiar to one skilled in the art of organic synthesis. This typically involves activation of the carboxyl component followed by reaction of the amine. Suitable activating groups include, but are not limited to, acyl halides, acyl azides, acylimidazoles, anhydrides, and esters as described by Montalbetti et al., *Tetrahedron*, 61:10827 (2005), which is hereby incorporated by reference in its entirety. Preferred activating reagents include thionyl chloride ($SOCl_2$), oxalyl chloride ($COCl)_2$, phosphorus oxychloride ($POCl_3$), carbonyl diimidazole (CDI), dicyclohexyl carbodiimide (DCC), 1-ethyl-3-(3-dimethylaminopropyl)carbodiimide) (EDCI), 1-hydroxybenzotriazole (HOBt), O-(1H-benzotriazol-1-yl)-N,N,N',N'-tetramethyluronium hexafluorophosphate (HATU), and 1-propanephosphonic acid cyclic anhydride (T3P).

Compounds useful according to the invention may be prepared by the application or adaptation of known methods, by which is meant methods used heretofore or described in the literature, for example, those described by Larock, *Comprehensive Organic Transformations*, Wiley-VCH Publishers, New York (1989), which is hereby incorporated by reference in its entirety.

A compound of the present invention including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxyl, amino, imino, thio, or carboxy groups, where these are desired in the final product, to avoid their unwanted participation in the reactions. Conventional protecting groups may be used in accordance with standard practice and as described below.

The novel 5-$HT_3$ modulators of formulae I and II of this invention can be prepared by the methods illustrated in the general reaction schemes as, for example, described below, or by modifications thereof, using readily available starting materials, reagents, and conventional synthesis procedures. In these reactions, it is also possible to make use of variants that are known in the art but are not mentioned here. Although the syntheses depicted herein may result in the preparation of enantiomers having a particular stereochemistry, included within the scope of the present invention are compounds of formulae I and II in any stereoisomeric form, and preparation of compounds of formulae I and II in stereoisomeric forms other than those depicted herein would be obvious to one of ordinary skill in the chemical arts based on the procedures presented herein.

General method of constructing a compound of formula Ia (A6 tricyclic core):

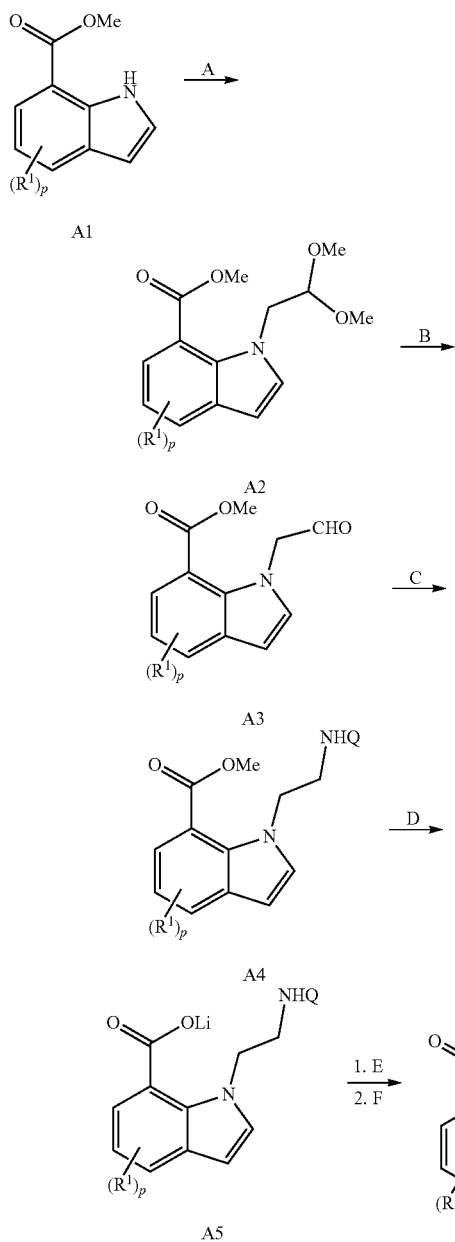

R[1] is consistent with formula I
QNH$_2$ = amine

Conditions: A) i. NaH, DMF; ii. K1, 2-bromo-1,1-dimethoxyethane; B) 1N HCl, THF; C) QNH$_2$, NaBH$_3$CN, 1% HOAc in MeOH; D) hydroxide base; E) T3P, diisopropylethylamine, THF; F) HCl, MeOH or CH$_2$Cl$_2$ Compound A1 where R[1]=OH and OCH$_3$ can be achieved by a method reported by Bissantz et al. (U.S. Patent Application Publication No. 2008/0153862), which is hereby incorporated by reference in its entirety. Conversion of A1 where R[1]=OH to R[1]=Cl can be achieved by a method reported in Bay et. al., *J. Org. Chem.*, 55:3415 (1990), which is hereby incorporated by reference in its entirety. Conversion of A1 where R[1]=OH to R[1]=Br can be achieved by a method reported by Riche et. al., *Justus Liebigs Ann. Chem.*, 121: 359 (1862), which is hereby incorporated by reference in its entirety. Conversion of A1 where R[1]=OH to R[1]=F can be achieved by a method reported by Ashton et. al., *J. Fluorine. Chem.*, 27:263 (1985), which is hereby incorporated by reference in its entirety. Conversion of A1 where R[1]=OH to R[1]=OTf (phenolic triflate ester) can be readily achieved (McCort et al., *Tetrahedron Lett.*, 40:6211 (1999), which is hereby incorporated by reference in its entirety). This material, or where R[1]=bromo, iodo or chloro, can be used as a coupling reagent for transition metal-catalyzed cross coupling reactions (e.g. Suzuki, Stille, Sonogashira) to provide compounds A1 where R[1]=alkyl, aryl, and heteroaryl.

General method of constructing a compound of formula Ib (B6 tricyclic core):

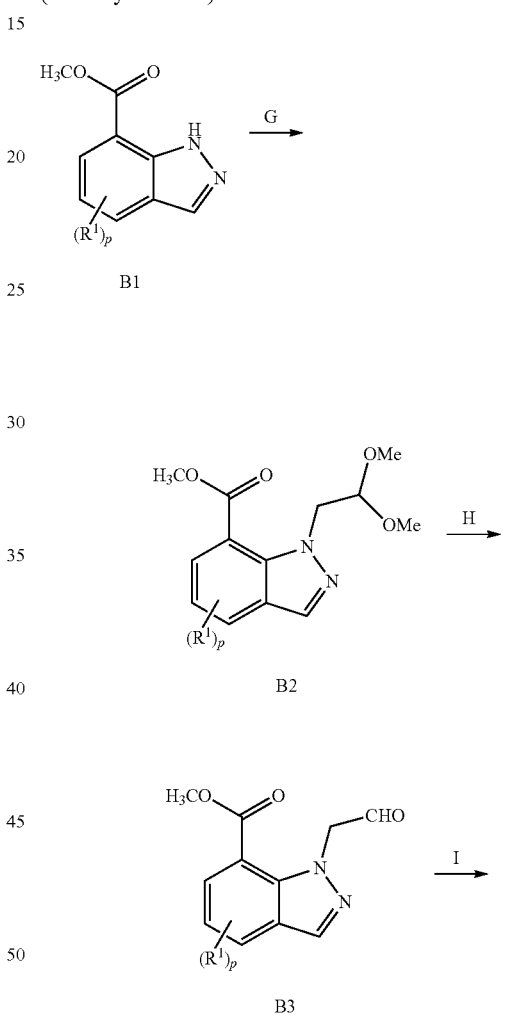

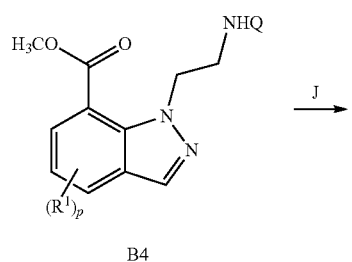

-continued

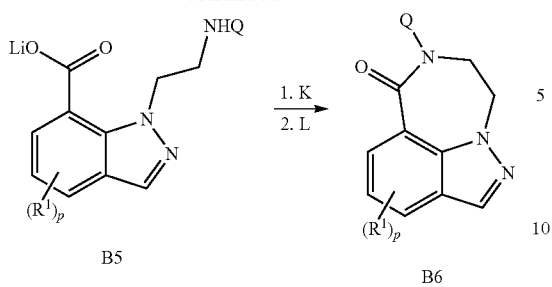

B5

B6

R[1] is consistent with formula I
QNH[2] = amine
Conditions: G) KI, 2-bromo-1,1-dimethoxyethane, DBU, DMSO; H) 2N HCl, 1,4-dioxane; I) QNH[2], NaBH[3]CN, 1% HOAc in MeOH; J) hydroxide base; K) T3P, diisopropylethylamine, THF; L) HCl, MeOH or CH[2]Cl[2]

Compound B1, where $R^1$=Br (5-bromo-7-indazolecarboxylic acid methyl ester), is commercially available from SINOVA, BETHESDA, Md. (catalog number SL-02167). Compound B1, where $R^1$=OH, OCH$_3$, F, or Cl can be prepared from the corresponding o-toluidine by a method reported by Ruechardt et. al., U.S. Pat. No. 3,862,958, which is hereby incorporated by reference in its entirety. Conversion of B1 where $R^1$=OH to $R^1$=OTf (phenolic triflate ester) can be readily achieved (McCort et al., *Tetrahedron Lett.,* 40:6211 (1999), which is hereby incorporated by reference in its entirety). This material, or where $R^1$=bromo, iodo or chloro, can be used as a coupling reagent for transition metal-catalyzed cross coupling reactions (e.g. Suzuki, Stille, Sonogashira) to provide compounds B1 where $R^1$=alkyl, aryl, and heteroaryl.

General method of constructing a compound of formula Ic (C9 tricyclic core):

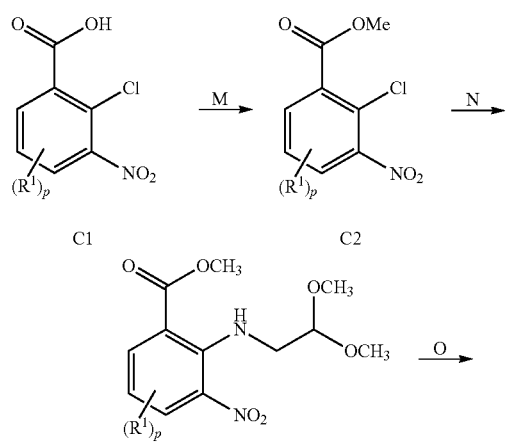

-continued

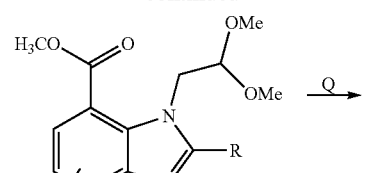

C5

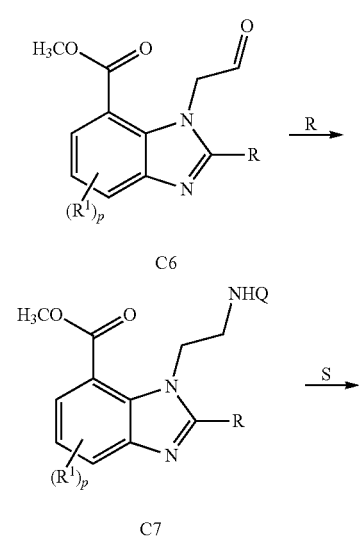

C6

C7

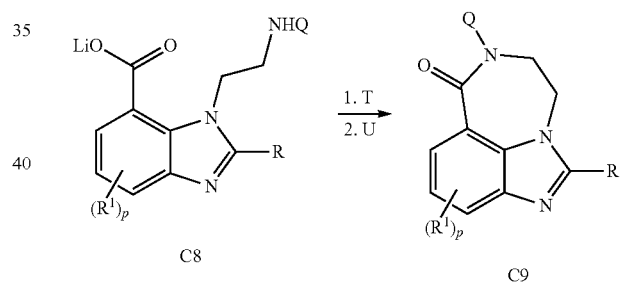

C8

C9

R and R[1] are consistent with formula I
QNH[2] = amine
Conditions: M) thionyl chloride, methanol; N) 2,2-dimethoxyethanamine, triethylamine, THF; O) hydrogen (1 atm), 10% palladium on carbon, ethanol; P1) RCHO, Oxane, DMF, H[2]O; P2) RC(OMe)[3], DMF; Q) TFA, H[2]O, CH[2]Cl[2]; R) QNH[2], NaBH[3]CN, 1% HOAc in MeOH; S) hydroxide base; T) T3P, diisopropylethylamine, THF; U) HCl, MeOH or CH[2]Cl[2]

General method of constructing a compound of formula IIa (D8 tricyclic core):

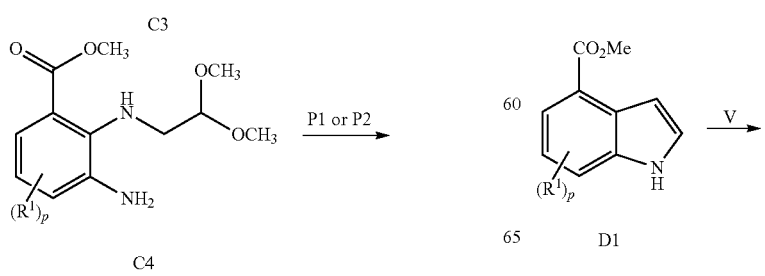

D1

31
-continued

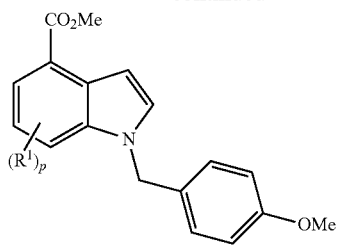

D2

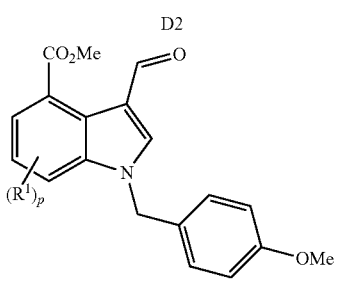

D3

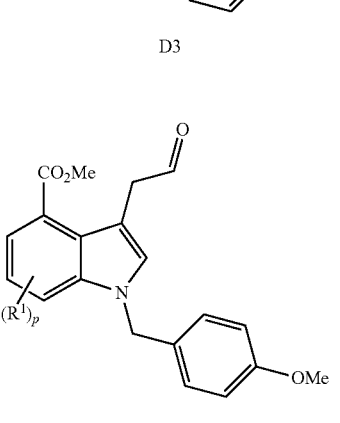

D4

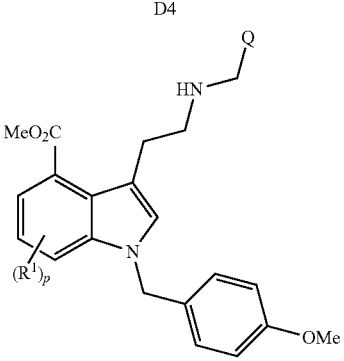

D5

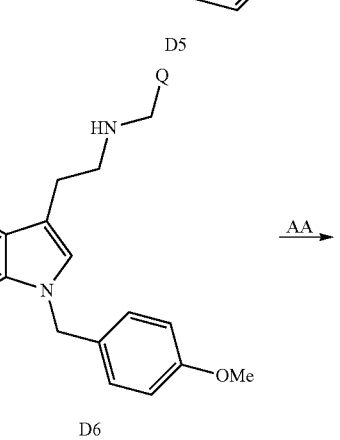

D6

32
-continued

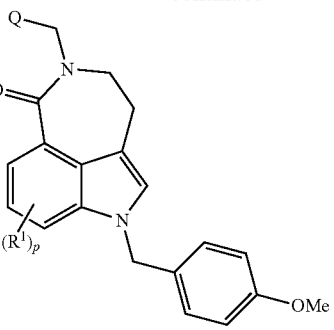

D7

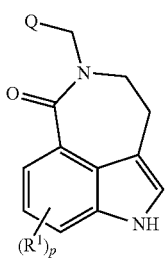

D9

$R^1$ is consistent with formula II
$QCN_2NH_2$ = amine

Conditions: V) 1-(chloromethyl)-4-methoxybenzene, sodium hydride (60%), tetrabutylammonium iodide, DMF; W) phosphorus oxychloride, DMF; X) i. $Ph_3PCH_2OCH_3Cl$, LiHMDS, THF; ii. 1N HCl, THF; Y) $QCH_2NH_2$, $NaBH_3CN$, 1% HOAc in MeOH; Z) hydroxide base; AA) T3P, diisopropylethylamine, THF; AB) aluminum chloride, anisole; AC) HCl, MeOH or $CH_2Cl_2$ Compound D1 where $R^1$=OH and $OCH_3$ can be achieved by a method reported by Krutosikova et al., *Collect. Czech. Chem. Commun.*, 57:1487 (1992), which is hereby incorporated by reference in its entirety. Conversion of D1 where $R^1$=OH to $R^1$=Cl can be achieved by a method reported in Bay et. al., *J. Org. Chem.*, 55:3415 (1990), which is hereby incorporated by reference in its entirety. Conversion of D1 where $R^1$=OH to $R^1$=Br can be achieved by a method reported by Riche et. al., *Justus Liebigs Ann. Chem.*, 121: 359 (1862), which is hereby incorporated by reference in its entirety. Conversion of D1 where $R^1$=OH to $R^1$=F can be achieved by a method reported by Ashton et. al., *J. Fluorine. Chem.*, 27:263 (1985), which is hereby incorporated by reference in its entirety. Conversion of D1 where $R^1$=OH to $R^1$=OTf (phenolic triflate ester) can be readily achieved (McCort et al., *Tetrahedron Lett.*, 40:6211 (1999), which is hereby incorporated by reference in its entirety). This material, or where $R^1$=bromo, iodo or chloro, can be used as a coupling reagent for transition metal-catalyzed cross coupling reactions (e.g. Suzuki, Stille, Sonogashira) to provide compounds D1 where $R^1$=alkyl, aryl, and heteroaryl.

General method of constructing a compound of formula IIb, where n=0 (E4 tricyclic core):

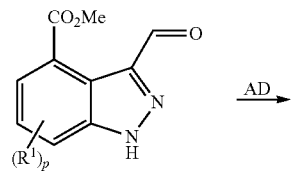

E1

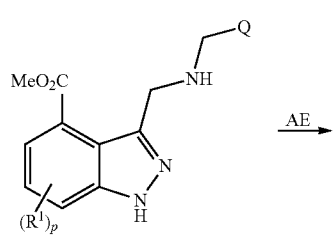

E2

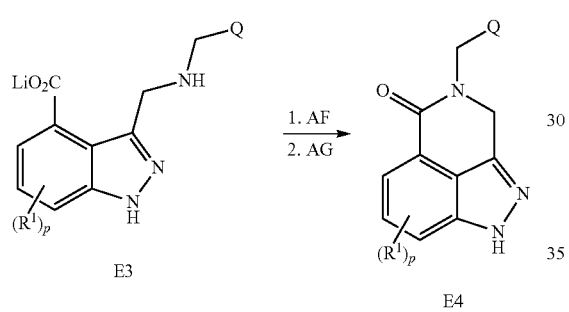

E3    E4

$R^1$ is consistent with formula II
$QCH_2NH_2$ = amine
Conditions: AD) $QCH_2NH_2$, $NaBH_3CN$, 1% HOAc in MeOH; AE) hydroxide base; AF) T3P, diisopropylethylamine, THF; AG) HCl, MeOH or $CH_2Cl_2$ Compound E1, where $R^1$=Br (6-bromo-3-formyl-4-indazole carboxylic acid methyl ester), is commercially available from SINOVA, BETHESDA, Md. (catalog number SL-00263). Compound E1, where $R^1$=Cl (6-chloro-3-formyl-4-indazole carboxylic acid methyl ester), is also commercially available from SINOVA, BETHESDA, Md. (catalog number SL-01561). Compound E1, where $R^1$=F (6-fluoro-3-formyl-4-indazole carboxylic acid methyl ester), is also commercially available from SINOVA, BETHESDA, Md. (catalog number SL-01547).

General method of constructing a compound of formula IIb, where n=1 (F6 tricyclic core):

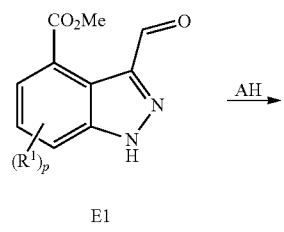

E1

-continued

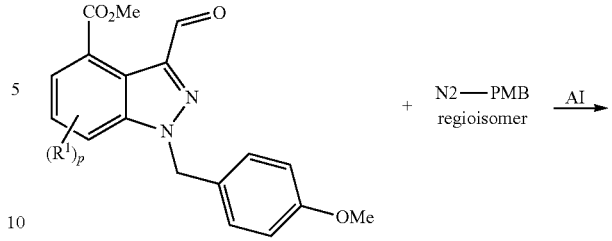

F1

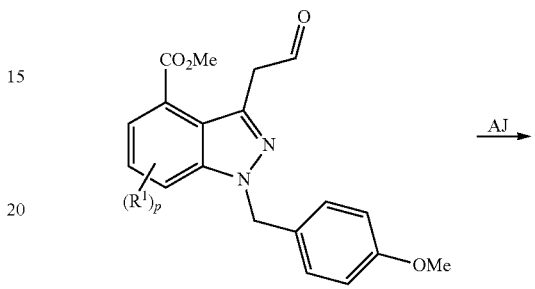

F2

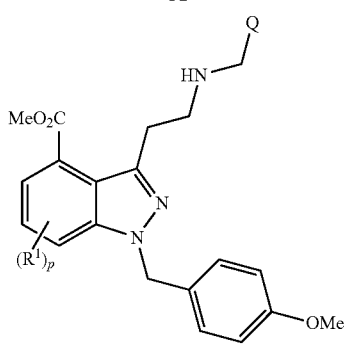

F3

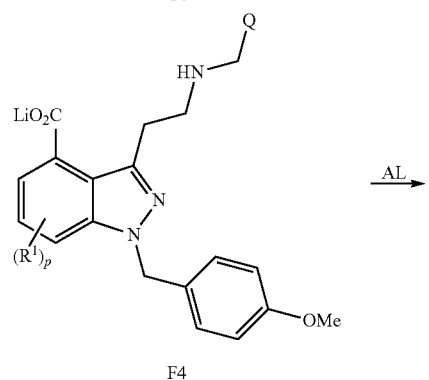

F4

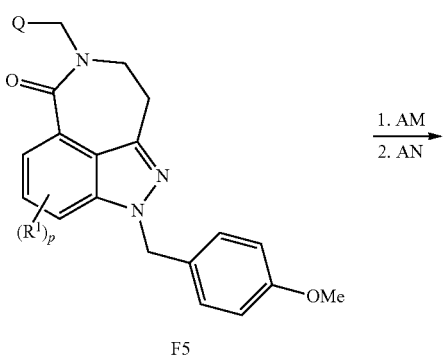

F5

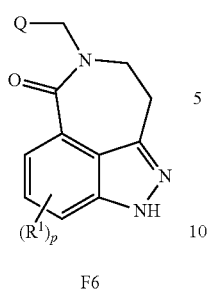

F6

$R^1$ is consistent with formula II
$QCH_2NH_2$ = amine
Conditions: AH) 1-(chloromethyl)-4-methoxybenzene, sodium hydride (60%), tetrabutylammonium iodide, DMF; AI) i. PH$_3$PCH$_2$OCH$_3$Cl, LiHMDS, THF; ii. 1N HCl, THF; AJ) QCH$_2$NH$_2$, NaBH$_3$CN, 1% HOAc IN MeOH; AK) hydroxide base; AL) T3P, diisopropylethylamine, THF; AM) trifluoroacetic acid; AN) HCl, MeOH or CH$_2$Cl$_2$ Compound E1, where $R^1$=Br (6-bromo-3-formyl-4-indazole carboxylic acid methyl ester), is commercially available from SINOVA, BETHESDA, Md. (catalog number SL-00263). Compound E1, where $R^1$=Cl (6-chloro-3-formyl-4-indazole carboxylic acid methyl ester), is also commercially available from SINOVA, BETHESDA, Md. (catalog number SL-01561). Compound E1, where $R^1$=F (6-fluoro-3-formyl-4-indazole carboxylic acid methyl ester), is also commercially available from SINOVA, BETHESDA, Md. (catalog number SL-01547).

General method of constructing a compound of formula IIc (G3 tricyclic core):

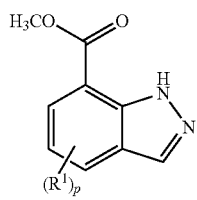

B1

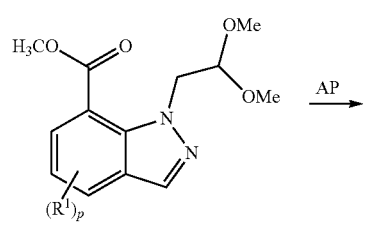

B2

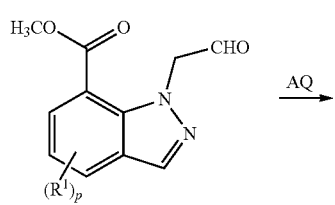

B3

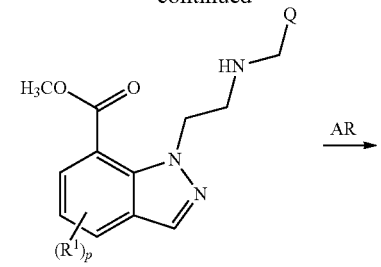

G1

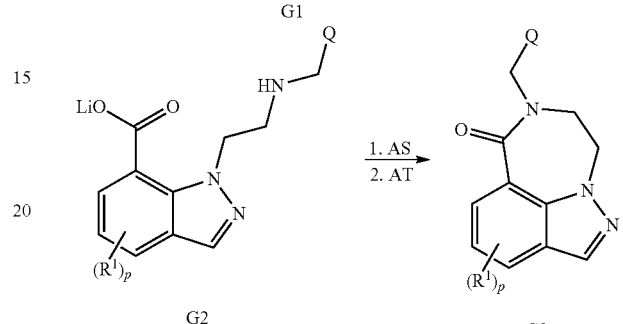

G2    G3

$R^1$ is consistent with formula II
$QCH_2NH_2$ = amine
Conditions: AO) KI, 2-bromo-1,1-dimethoxyethane, DBU, DMSO; AP) 2N HCl, 1,4-dioxane; AQ) QCH$_2$NH$_2$, NaBH$_3$CN, 1% HOAc in MeOH; AR) hydroxide base; AS) T3P, diisopropylethylamine, THF; AT) HCl, MeOH or CH$_2$Cl$_2$ Compound B1, where $R^1$=Br (5-bromo-7-indazolecarboxylic acid methyl ester), is commercially available from SINOVA, BETHESDA, Md. (catalog number SL-02167). Compound B1, where $R^1$=OH, OCH$_3$, F, or Cl can be prepared from the corresponding o-toluidine by a method reported by Ruechardt et. al., U.S. Pat. No. 3,862,958, which is hereby incorporated by reference in its entirety. Conversion of B1 where $R^1$=OH to $R^1$=OTf (phenolic triflate ester) can be readily achieved (McCort et al., *Tetrahedron Lett.*, 40:6211 (1999), which is hereby incorporated by reference in its entirety). This material, or where $R^1$=bromo, iodo or chloro, can be used as a coupling reagent for transition metal-catalyzed cross coupling reactions (e.g. Suzuki, Stille, Sonogashira) to provide compounds B1 where $R^1$=alkyl, aryl, and heteroaryl.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining one or more active ingredients useful in treating the disease. A kit may provide (alone or in combination with a pharmaceutically acceptable diluent or carrier) the compounds of formula I or II and an additional active ingredient (alone or in combination with diluent or carrier), as described above.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The formulations of compounds of formulae I and II, include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or II or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I or II to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula I or II which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

For additional information about pharmaceutical compositions and their formulation, see, for example, Remington, *The Science and Practice of Pharmacy*, 20*th* Edition (2000), which is hereby incorporated by reference in its entirety.

The compounds of formula I or II can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula I or II can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula I or II can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., *Nature Reviews Drug Discovery* 3:115 (2004), which is hereby incorporated by reference in its entirety)).

Compounds of formula I or II can be incorporated into a liposome to improve half-life. Compounds of formula I or II can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula I or II can also be administered via a nanocochleate or cochleate delivery vehicle (BioDelivery Sciences International, Raleigh, N.C.). Compounds of formula I or II can also be delivered using nanoemulsion formulations.

EXAMPLES

The present invention is not limited to the compounds found in the above examples, and many other compounds falling within the scope of the invention may also be prepared using the procedures set forth in the above synthetic schemes. The preparation of additional compounds of formula I or II using these methods will be apparent to one of ordinary skill in the chemical arts.

Unless otherwise noted, reagents and solvents were used as received from commercial suppliers. Proton nuclear magnetic resonance (NMR) spectra were obtained on Bruker spectrometers at 300, 400, or 500 MHz. Spectra are given in ppm (δ) and coupling constants, J, are reported in Hertz. Tetramethylsilane (TMS) was used as an internal standard. Mass spectra were collected using either a Finnigan LCQ Duo LC-MS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex, Torrance, Calif.) with UV detection at 254 nm using a standard solvent gradient program (Method A or Method B).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid Example 1

Preparation of (R)-2-(quinuclidin-3-yl)-3,4-dihydro-[1,4]diazepino[6,7,1-hi]indol-1(2H)-one, hydrochloride salt

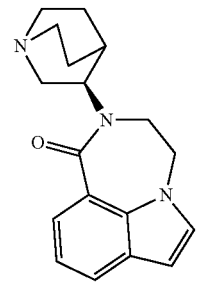 [SMILES: O=C1c2cccc3ccn(c23)CCN1[C@H]1CN2CCC1CC2]

Step A: To a stirred solution of methyl 1H-indole-7-carboxylate (2.0 g, 11.4 mmol) in DMF (10 ml) was added sodium hydride (800 mg, 20 mmol) in portions. The mixture was stirred at room temperature for 1 h, then potassium iodide (160 mg, 0.9 mmol) and 2-bromo-1,1-dimethoxyethane (3.4 ml, 28.5 mmol) were added. The mixture was heated to 80° C. for 15 h. After cooling to room temperature, the reaction was quenched with saturated aqueous ammonium chloride, extracted with ethyl acetate (3×), washed with brine, dried over sodium sulfate, filtered, and concentrated under reduced pressure. The crude material was purified by column chromatography (silica gel, 70:30 hexanes/ethyl acetate) to afford methyl 1-(2,2-dimethoxyethyl)-1H-indole-7-carboxylate (1.77 g, 59%) as a semitransparent liquid: $^1$H NMR (500 MHz, CDCl$_3$) δ 7.77 (dd, J=4.5, 1.0 Hz, 1H), 7.66 (dd, J=4.3, 1.0 Hz, 1H), 7.19 (d, J=1.5 Hz, 1H), 7.10 (t, J=8.0 Hz, 1H), 6.57 (d, J=1.8 Hz, 1H), 4.54-4.52 (dd, J=5.0, 4.5 Hz, 1H), 4.48 (d, J=2.5 Hz, 2H), 3.96 (s, 3H), 3.31 (s, 6H).

Step B: To a stirred solution of methyl 1-(2,2-dimethoxyethyl)-1H-indole-7-carboxylate (1.77 g, 6.7 mmol) from Step A above in THF (30 ml) was added 1N HCl (30 ml). The mixture was heated to 60° C. for 2 h. The solvent was evaporated and the residue purified by column chromatography (silica gel, 70:30 hexanes/ethyl acetate) to afford methyl 1-(2-oxoethyl)-1H-indole-7-carboxylate (1.27 g, 87%) as a light yellow solid: $^1$H NMR (500 MHz, CDCl$_3$) δ 9.77 (s, 1H), 7.84

(dd, J=4.5, 1.0 Hz, 2H), 7.15 (t, J=8.0 Hz, 1H), 7.04 (d, J=1.5 Hz, 1H), 6.67 (d, J=1.5 Hz, 1H), 3.90 (s, 3H), 2.05 (s, 2H); MS (ESI+) m/z 218 (M+H).

Step C: To a stirred suspension of (R)-(+)-3-aminoquinuclidine (1.4 g, 7.0 mmol) in methylene chloride (50 mL) was added sodium hydride (562 mg, 14.0 mmol) in portions and the mixture was stirred for 1 h. Acetic acid (0.6 mL) was added dropwise, followed by methyl 1-(2-oxoethyl)-1H-indole-7-carboxylate (1.3 g, 5.9 mmol) from Step B above and the mixture continued to stir at room temperature for 2 h. Sodium triacetoxyborohydride (4.2 g, 19.6 mmol) was added in one portion and stirring was continued overnight at room temperature. The solvent was removed under reduced pressure and the crude material was purified by column chromatography (silica gel, 90:10:1 methylene chloride/methanol/concentrated ammonium hydroxide) to afford (R)-methyl 1-(2-(quinuclidin-3-ylamino)ethyl)-1H-indole-7-carboxylate (1.64 g, 86%) as a brown solid: $^1$H NMR (500 MHz, CD$_3$OD) δ 7.77 (d, J=4.0 Hz, 1H), 7.62 (d, J=3.8 Hz 1H), 7.30 (d, J=1.5 Hz, 1H), 7.08 (t, J=7.5 Hz, 1H), 6.58 (d, J=1.5 Hz, 1H), 4.50 (t, J=6.5 Hz, 2H), 3.96 (s, 3H), 3.35 (s, 2H), 3.00-2.97 (m, 1H), 2.85-2.58 (m, 7H), 2.21-2.17 (m, 1H), 1.70-1.56 (m, 3H), 1.44-1.42 (m, 1H), 1.27-1.25 (m, 1H); MS (ESI+) m/z 328 (M+H).

Step D: To a stirred solution of (R)-methyl 1-(2-(quinuclidin-3-ylamino)ethyl)-1H-indole-7-carboxylate (1.6 g, 5.0 mmol) from Step C above in THF (20 ml) and H$_2$O (20 ml) was added lithium hydroxide monohydrate (632 mg, 15.1 mmol). The mixture was stirred at room temperature overnight and then concentrated under reduced pressure. The residue was dried overnight under vacuum to afford crude lithium (R)-1-(2-(quinuclidin-3-ylamino)ethyl)-1H-indole-7-carboxylate which was used in the next step without further purification: MS (ESI+) m/z 314 (M+H).

Step E: To a stirred solution of crude lithium (R)-1-(2-(quinuclidin-3-ylamino)ethyl)-1H-indole-7-carboxylate from Step D above in N,N-dimethylformamide (10 mL) was added N,N-diisopropylethylamine (2.3 mL, 13.8 mmol) followed by 1-propanephosphonic acid cyclic anhydride (T3P) (4.1 mL, 13.8 mmol) at room temperature and the mixture was stirred for 17 h. The reaction was quenched with water, extracted with methylene chloride (3×), washed with brine, dried over sodium sulfate, filtered, and concentrated under reduced pressure. The crude material was purified by column chromatography (silica gel, 60:30:10 methylene chloride/methanol/concentrated ammonium hydroxide) and preparative TLC (60:30:10 methylene chloride/methanol/concentrated ammonium hydroxide) to afford (R)-2-(quinuclidin-3-yl)-3,4-dihydro-[1,4]diazepino[6,7,1-hi]indol-1(2H)-one. This material was dissolved in methanol and treated with HCl (1.25 M solution in methanol). The resulting hydrochloride salt was lyophilized from water to afford (R)-2-(quinuclidin-3-yl)-3,4-dihydro-[1,4]diazepino[6,7,1-hi]indol-1(2H)-one hydrochloride (377 mg, 21%) as a light yellow solid: $^1$H NMR (500 MHz, DMSO-d$_6$) δ 7.85 (d, J=4.0 Hz, 1H), 7.77 (dd, J=4.3, 1.0 Hz, 1H), 7.45 (d, J=1.5, 1H), 7.14 (t, J=7.5 Hz, 1H), 6.57 (d, J=1.5, 1H), 4.72 (t, J=8.5 Hz, 1H), 4.50 (br s, 1H), 4.34 (br s, 1H), 3.91 (br s, 1H), 3.43-3.18 (m, 4H), 3.00 (t, J=8.0 Hz, 3H), 2.13 (d, J=1.0 Hz, 1H), 1.83-1.71 (m, 3H), 1.63 (t, J=11.0 Hz, 1H); MS (ESI+) m/z 296 (M+H).

Example 2

Preparation of (S)-2-(quinuclidin-3-yl)-3,4-dihydro-[1,4]diazepino[6,7,1-hi]indol-1(2H)-one, hydrochloride salt

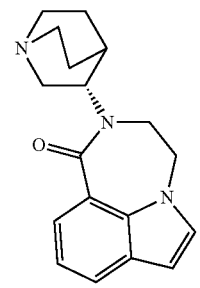 [SMILES: O=C1c2cccc3ccn(c23)CCN1[C@@H]1CN2CCC1CC2]

Step A: To methyl 1H-indole-7-carboxylate (2.0 g, 11.4 mmol) dissolved in DMF (10 ml) was added sodium hydride (800 mg, 20 mmol) in portions. The mixture was stirred at room temperature for 1 h, then potassium iodide (160 mg, 0.9 mmol) and 2-bromo-1,1-dimethoxyethane (3.4 ml, 28.5 mmol) were added. The mixture was heated to 80° C. and stirred overnight. After cooling to room temperature, the mixture was quenched by saturated aqueous ammonium chloride, extracted with ethyl acetate (3×), washed with brine, dried over sodium sulfate, filtered, and concentrated under reduced pressure. The crude material was purified by column chromatography (silica gel, 70:30 hexanes/ethyl acetate) to afford methyl 1-(2,2-dimethoxyethyl)-1H-indole-7-carboxylate (1.77 g, 59%) as a semitransparent liquid: $^1$H NMR (500 MHz, CDCl$_3$) δ 7.77 (dd, J=4.5, 1.0 Hz, 1H), 7.66 (dd, J=4.3, 1.0 Hz, 1H), 7.19 (d, J=1.5 Hz, 1H), 7.10 (t, J=8.0 Hz, 1H), 6.57 (d, J=1.8 Hz, 1H), 4.54-4.52 (dd, J=5.0, 4.5 Hz, 1H), 4.48 (d, J=2.5 Hz, 2H), 3.96 (s, 3H), 3.31 (s, 6H).

Step B: To a stirred solution of methyl 1-(2,2-dimethoxyethyl)-1H-indole-7-carboxylate (1.8 g, 6.7 mmol) from Step A above in THF (30 ml) was added 1N HCl (30 ml). The mixture was heated to 60° C. for 2 h. The solvent was evaporated and the residue purified by column chromatography (silica gel, 70:30 hexanes/ethyl acetate) to afford methyl 1-(2-oxoethyl)-1H-indole-7-carboxylate (1.3 g, 87%) as a light yellow solid: $^1$H NMR (500 MHz, CDCl$_3$) δ 9.77 (s, 1H), 7.84 (dd, J=4.5, 1.0 Hz, 2H), 7.15 (t, J=8.0 Hz, 1H), 7.04 (d, J=1.5 Hz, 1H), 6.67 (d, J=1.5 Hz, 1H), 3.90 (s, 3H), 2.05 (s, 2H); MS (ESI+) m/z 218 (M+H).

Step C: To a stirred suspension of (S)-(−)-3-aminoquinuclidine (1.4 g, 7.0 mmol) in methylene chloride (50 mL) was added sodium hydride (562 mg, 14.0 mmol) in portions and the mixture was stirred for 1 h. Acetic acid (0.6 mL) was added dropwise, followed by methyl 1-(2-oxoethyl)-1H-indole-7-carboxylate (1.3 g, 5.9 mmol) from Step B above and the reaction was stirred at room temperature for 2 h. Sodium triacetoxyborohydride (4.2 g, 19.6 mmol) was then added in one portion and stirring was continued overnight at room temperature. The solvent was removed under reduced pressure and the crude material was purified by column chromatography (silica gel, 90:10:1 methylene chloride/methanol/concentrated ammonium hydroxide) to afford (S)-methyl 1-(2-(quinuclidin-3-ylamino)ethyl)-1H-indole-7-carboxylate (1.39 g, 66%) as a brown solid: ¹H NMR (500 MHz, CDCl₃) δ 7.79 (dd, J=4.5, 1.0 Hz, 1H), 7.69 (dd, J=4.3 Hz 1H), 7.18 (d, J=1.8 Hz, 1H), 7.10 (t, J=7.5 Hz, 1H), 6.57 (d, J=1.8 Hz, 1H), 4.51 (t, J=6.5 Hz, 2H), 3.96 (s, 3H), 3.46 (s, 1H), 3.07-3.03 (m, 1H), 2.90-2.85 (m, 1H), 2.82-2.70 (m, 5H), 2.63-2.60 (m, 1H), 2.29-2.25 (m, 1H), 1.68-1.59 (m, 3H), 1.40-1.39 (m, 1H), 1.25-1.22 (m, 1H); MS (ESI+) m/z 328 (M+H).

Step D: To a stirred solution of (S)-methyl 1-(2-(quinuclidin-3-ylamino)ethyl)-1H-indole-7-carboxylate (1.4 g, 4.3 mmol) from Step C above in THF (20 ml) and water (20 ml) was added lithium hydroxide monohydrate (535 mg, 12.8 mmol). The mixture was stirred at room temperature overnight and then concentrated under reduced pressure. The residue was dried overnight under vacuum to afford crude lithium (S)-1-(2-(quinuclidin-3-ylamino)ethyl)-1H-indole-7-carboxylate which was used in the next step without further purification: MS (ESI+) m/z 314 (M+H).

Step E: To a stirred solution of crude lithium (S)-1-(2-(quinuclidin-3-ylamino)ethyl)-1H-indole-7-carboxylate from Step D above in N,N-dimethylformamide (15 mL) was added N,N-diisopropylethylamine (4.3 mL, 26.1 mmol) followed by 1-propanephosphonic acid cyclic anhydride (T3P) (7.8 mL, 26.1 mmol) and the reaction was stirred at room temperature for 17 h. The reaction was quenched with water, extracted with methylene chloride (3×), washed with brine, dried over sodium sulfate, filtered, and concentrated under reduced pressure. The crude material was purified by column chromatography (silica gel, 60:30:10 methylene chloride/methanol/concentrated ammonium hydroxide) to afford (S)-2-(quinuclidin-3-yl)-3,4-dihydro-[1,4]diazepino[6,7,1-hi]indol-1(2H)-one. This material was dissolved in methanol and treated with HCl (1.25 M solution in methanol) and the mixture was concentrated under reduced pressure. The residue was lyophilized from water to afford (S)-2-(quinuclidin-3-yl)-3,4-dihydro-[1,4]diazepino[6,7,1-hi]indol-1(2H)-one hydrochloride (800 mg, 62%) as a white solid: ¹H NMR (500 MHz, CD₃OD) δ 7.93 (d, J=4.0 Hz, 1H), 7.77 (dd, J=4.5, 1.0 Hz, 1H), 7.26 (d, J=1.8 Hz, 1H), 7.17 (t, J=8.0 Hz, 1H), 6.59 (d, J=1.8 Hz, 1H), 4.71 (br s, 1H), 4.53 (br s, 1H), 4.46 (d, J=5.5 Hz, 1H), 4.08 (br s, 1H), 4.00-3.96 (m, 1H), 3.86-3.69 (m, 3H), 3.46-3.31 (m, 3H), 2.51 (q, J=5.5 Hz, 1H), 2.26 (br s, 1H), 2.19-1.98 (m, 3H); MS (ESI+) m/z 296 (M+H).

Example 3

Preparation of (S)-7-methyl-2-(quinuclidin-3-yl)-3,4-dihydro-[1,4]diazepino[6,7,1-hi]indol-1(2H)-one, hydrochloride salt

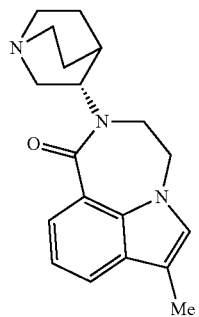 [SMILES: Cc1cn2c3c(cccc13)C(=O)N([C@@H]1CN3CCC1CC3)CC2]

Step A: Phosphorus(V) oxychloride (0.7 ml, 7.6 mmol) was slowly added to DMF (5 ml) at 0° C. The mixture was stirred for 15 min and then was treated with a solution of (S)-2-(quinuclidin-3-yl)-3,4-dihydro-[1,4]diazepino[6,7,1-hi]indol-1(2H)-one (250 mg, 0.8 mmol) from Step E of Example 2 in DMF (5 ml). The reaction mixture was warmed to room temperature and stirred overnight. After removing the solvent under reduced pressure, the residue was dissolved in water and basified using saturated sodium carbonate to precipitate (S)-1-oxo-2-(quinuclidin-3-yl)-1,2,3,4-tetrahydro-[1,4]diazepino[6,7,1-hi]indole-7-carbaldehyde (148 mg, 63%) as a white solid: ¹H NMR (500 MHz, CD₃OD) δ 9.94 (s, 1H), 8.43 (d, J=4.0 Hz, 1H), 8.14 (s, 1H), 8.07 (d, J=3.8 Hz, 1H), 7.41 (t, J=7.5 Hz, 1H), 4.71 (br s, 1H), 4.53 (s, 1H), 4.46 (d, J=5.5 Hz, 1H), 4.08 (br s, 1H), 3.98 (dd, J=12.0, 7.5 Hz, 1H), 3.86-3.69 (m, 3H), 3.45-3.31 (m, 3H), 2.51 (q, J=4.3, 2.5 Hz, 1H), 2.26 (br s, 1H), 2.19-1.98 (m, 3H); MS (ESI+) m/z 324 (M+H).

Step B: Sodium borohydride (36 mg, 1.0 mmol) was added to a suspension of (S)-1-oxo-2-(quinuclidin-3-yl)-1,2,3,4-tetrahydro-[1,4]diazepino[6,7,1-hi]indole-7-carbaldehyde (148 mg, 0.5 mmol) from Step A above in ethanol (15 mL). The reaction mixture was heated at reflux for 2 h and then cooled to room temperature and the solvent was removed under reduced pressure. The crude product, (S)-7-(hydroxymethyl)-2-(quinuclidin-3-yl)-3,4-dihydro-[1,4]diazepino[6,7,1-hi]indol-1(2H)-one was used directly in the next step without further purification: MS (ESI+) m/z 326 (M+H).

Step C: 4-(Dimethylamino)pyridine (13 mg, 0.05 mmol) was added to a solution of (S)-7-(hydroxymethyl)-2-(quinuclidin-3-yl)-3,4-dihydro-[1,4]diazepino[6,7,1-hi]indol-1(2H)-one from Step B above in a mixture of acetic anhydride (0.1 ml, 1.2 mmol) and pyridine (3 ml). The mixture was stirred overnight at room temperature, the solvent was removed under reduced pressure, and the residue was purified by column chromatography (silica gel, 90:10:1 methylene chloride/methanol/concentrated ammonium hydroxide) to afford (S)-(1-oxo-2-(quinuclidin-3-yl)-1,2,3,4-tetrahydro-[1,4]diazepino[6,7,1-hi]indol-7-yl)methyl acetate (124 mg, 71%) as a white solid: MS (ESI+) m/z 368 (M+H).

Step D: (S)-(1-Oxo-2-(quinuclidin-3-yl)-1,2,3,4-tetrahydro-[1,4]diazepino[6,7,1-hi]indol-7-yl)methyl acetate (124 mg, 0.34 mmol) from Step C above was dissolved in methanol (7 ml) and glacial acetic acid (3 ml). Excess 10% palladium on carbon was added and the suspension was stirred under an atmosphere of hydrogen (balloon pressure) overnight. The suspension was filtered through Celite and the filtrate was concentrated under reduced pressure and purified by column chromatography (silica gel, 90:10:1 methylene chloride/methanol/concentrated ammonium hydroxide) and preparative TLC (90:10:10 methylene chloride/methanol/concentrated ammonium hydroxide) to afford (S)-7-methyl-2-(quinuclidin-3-yl)-3,4-dihydro-[1,4]diazepino[6,7,1-hi]indol-1(2H)-one. This material was dissolved in methanol and treated with HCl (1.25 M solution in methanol) and the mixture was concentrated under reduced pressure. The residue was lyophilized from water to afford (S)-7-methyl-2-(quinuclidin-3-yl)-3,4-dihydro-[1,4]diazepino[6,7,1-hi]indol-1(2H)-one hydrochloride (100 mg, 85%) as a white solid: ¹H NMR (500 MHz, CD₃OD) δ 7.80 (d, J=4.0 Hz, 1H), 7.75 (d, J=3.8 Hz, 1H), 7.17 (t, J=8.0 Hz, 1H), 7.17 (t, J=8.0 Hz, 1H), 4.90 (s, 1H), 4.22 (br s, 1H), 4.11 (br s, 1H), 3.77-3.72

(m, 2H), 3.48-3.29 (m, 6H), 2.35 (d, J=8.0 Hz, 1H), 2.21 (s, 3H), 2.06-1.96 (m, 4H); MS (ESI+) m/z 310 (M+H).

Example 4

Preparation of (S)-9-chloro-7-methyl-2-(quinuclidin-3-yl)-3,4-dihydro-[1,4]diazepino[6,7,1-hi]indol-1(2H)-one, hydrochloride salt

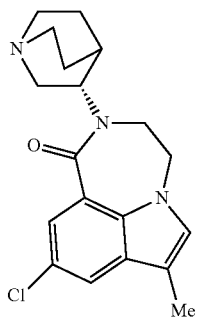 [SMILES: Cc1cn2c3c(cc(Cl)cc13)C(=O)N([C@@H]1CN3CCC1CC3)CC2]

Step A: Tetrabutylammonium chloride (100 mg, 0.4 mmol), trimethyl(prop-1-ynyl)silane (1.1 ml, 7.2 mmol), methyl 2-amino-5-chloro-3-iodobenzoate (1.0 g, 3.6 mmol), triphenylphosphine (47.2 mg, 0.1 mmol), palladium(II) acetate (20 mg, 0.1 mmol) and sodium carbonate (1.9 g, 18 mmol) in DMF were added to a sealed tube and the reaction was stirred at 100° C. for 15 h: After cooling to room temperature, the reaction mixture was diluted with ether and washed with saturated aqueous ammonium chloride and water. The organic layer was dried over sodium sulfate, filtered, and concentrated under reduced pressure. The crude material was then purified by column chromatography (silica gel, 70:30 hexanes/ethyl acetate) to afford methyl 5-chloro-3-methyl-2-(trimethylsilyl)-1H-indole-7-carboxylate (620 mg, 59%) as a light yellow solid: $^1$H NMR (500 MHz, CDCl$_3$) δ 9.50 (s, 1H), 7.80 (d, J=1.0 Hz, 1H), 7.72 (d, J=1.0 Hz, 1H), 3.98 (s, 3H), 2.37 (s, 3H), 0.40 (t, 9H); MS (ESI+) m/z 296 (M+H).

Step B: Methyl 5-chloro-3-methyl-2-(trimethylsilyl)-1H-indole-7-carboxylate (510 mg, 1.73 mmol) from Step A above and aluminum chloride (254 mg, 1.9 mmol) were added to methylene chloride (5 mL) and the reaction mixture was stirred for 3 h at 0° C. The reaction was quenched with water, extracted with ether, dried over sodium sulfate, filtered, and concentrated to afford methyl 5-chloro-3-methyl-1H-indole-7-carboxylate (410 mg, quantitative yield) as a dark green solid: $^1$H NMR (500 MHz, CDCl$_3$) δ 8.09 (s, 1H), 8.01 (d, J=1.0 Hz, 1H), 7.87 (d, J=1.0 Hz, 1H), 4.01 (s, 3H), 3.40 (s, 3H); MS (ESI+) m/z 224 (M+H).

Step C: To a stirred solution of methyl 5-chloro-3-methyl-1H-indole-7-carboxylate (1.4 g, 4.5 mmol) from Step B above in DMF (10 ml) was added sodium hydride (313 mg, 7.8 mmol) in portions. The mixture was stirred at room temperature for 1 h, then potassium iodide (60 mg, 0.4 mmol) and 2-bromo-1,1-dimethoxyethane (2.1 ml, 17.9 mmol) were added. The mixture was heated to 80° C. for 15 h. After cooling to room temperature, the reaction was quenched with saturated aqueous ammonium chloride, extracted with ethyl acetate (3×), washed with brine, filtered, and dried over sodium sulfate. The filtrate was concentrated under reduced pressure and the residue purified by column chromatography (silica gel, 70:30 hexanes/ethyl acetate) to afford methyl 5-chloro-1-(2,2-dimethoxyethyl)-3-methyl-1H-indole-7-carboxylate (908 mg, 68%) as a semitransparent liquid: $^1$H NMR (500 MHz, CDCl$_3$) δ 7.64 (d, J=1.0 Hz, 1H), 7.61 (d, J=1.0 Hz, 1H), 6.94 (s, 1H), 4.62 (t, J=5.0 Hz, 1H), 4.39 (d, J=5.0 Hz, 1H), 3.96 (s, 3H), 3.30 (s, 6H), 2.27 (s, 3H).

Step D: To a stirred solution of methyl 5-chloro-1-(2,2-dimethoxyethyl)-3-methyl-1H-indole-7-carboxylate (909 mg, 2.9 mmol) from Step C above in THF (20 ml) was added 2N HCl (20 ml). The mixture was heated to 60° C. for 4 h. The solvent was evaporated and the residue purified by column chromatography (silica gel, 70:30 hexanes/ethyl acetate) to afford methyl 5-chloro-3-methyl-1-(2-oxoethyl)-1H-indole-7-carboxylate (690 mg, 89%) as a yellow solid: MS (ESI+) m/z 266 (M+H).

Step E: To a stirred suspension of (S)-(−)-3-aminoquinuclidine dihydrochloride (621 mg, 3.1 mmol) in methylene chloride (20 mL) was added sodium hydride (250 mg, 6.2 mmol) in portions and the mixture was stirred for 1 h. Acetic acid (0.6 mL) was added dropwise and then methyl 5-chloro-3-methyl-1-(2-oxoethyl)-1H-indole-7-carboxylate (690 mg, 2.6 mmol) from Step D above was added and the mixture continued to stir at room temperature for 2 h. Sodium triacetoxyborohydride (2.2 g, 10.4 mmol) was added in one portion and stirring was continued overnight at room temperature. The solvent was removed under reduced pressure and the crude material was purified by column chromatography (silica gel, 90:10:1 methylene chloride/methanol/concentrated ammonium hydroxide) to afford (S)-methyl 5-chloro-3-methyl-1-((quinuclidin-3-ylamino)methyl)-1H-indole-7-carboxylate (1.0 g, quantitative yield) as a light yellow solid: $^1$H NMR (500 MHz, CD$_3$OD) δ 7.69 (d, J=1.0 Hz, 1H), 7.56 (d, J=1.0 Hz, 1H), 7.14 (s, 1H), 3.02-2.97 (m, 1H), 2.84-2.62 (m, 8H), 3.00-2.97 (m, 1H), 2.85-2.58 (m, 7H), 2.32 (s, 3H), 2.23-2.19 (dq, J=10.0, 2.0 Hz, 1H), 1.72-1.61 (m, 3H), 1.47-1.45 (m, 1H), 1.47-1.45 (m, 1H); MS (ESI+) m/z 362 (M+H).

Step F: To a stirred solution of (S)-methyl 1-(2-(quinuclidin-3-ylamino)ethyl)-1H-indole-7-carboxylate (1.0 g, 2.7 mmol) from Step E above in THF (15 ml) and water (15 ml) was added lithium hydroxide monohydrate (344 mg, 8.2 mmol). The mixture was stirred at room temperature overnight and then concentrated under reduced pressure. The residue was dried overnight under vacuum to afford crude lithium (S)-5-chloro-3-methyl-1-((quinuclidin-3-ylamino)methyl)-1H-indole-7-carboxylate, which was used in the next step without further purification: MS (ESI+) m/z 354 (M+H).

Step G: To a stirred solution of lithium (S)-5-chloro-3-methyl-1-((quinuclidin-3-ylamino)methyl)-1H-indole-7-carboxylate from Step F above in THF (40 mL) was added N,N-diisopropylethylamine (2.4 mL, 13.7 mmol) followed by 1-propanephosphonic acid cyclic anhydride (T3P) (4.1 mL, 13.7 mmol) at room temperature and the mixture was stirred for 3 h. The reaction was quenched with water, extracted with methylene chloride (3×), washed with brine, dried over sodium sulfate, filtered, and concentrated under reduced pressure. The crude material was purified by column chromatography (silica gel, 60:30:10 methylene chloride/methanol/concentrated ammonium hydroxide) and preparative TLC (60:30:10 methylene chloride/methanol/concentrated ammonium hydroxide) to afford (S)-9-chloro-7-methyl-2-(quinuclidin-3-yl)-3,4-dihydro-[1,4]diazepino[6,7,1-hi]indol-1(2H)-one. This material was dissolved in methanol and treated with HCl (1.25 M solution in methanol). The resulting hydrochloride salt was lyophilized from water to afford (S)-9-chloro-7-methyl-2-(quinuclidin-3-yl)-3,4-dihydro-[1,4]diazepino[6,7,1-hi]indol-1(2H)-one hydrochloride (466 mg, 47%) as a light yellow solid: $^1$H NMR (500 MHz, CDCl$_3$) δ 11.98 (s, 1H), 7.96 (d, J=1.0 Hz, 1H), 7.66 (d, J=1.0 Hz, 1H), 6.88 (s, 1H), 4.98 (br s, 1H), 4.50 (br s, 1H), 4.31 (br s, 1H), 4.23 (br s, 3H), 3.95 (t, J=6.0 Hz, 1H), 3.68 (s, 1H), 3.34 (br s, 1H), 3.23 (br s, 1H), 2.44 (br s, 1H), 2.24 (br s, 5H), 2.08-1.92 (m, 2H): MS (ESI+) m/z 344 (M+H).

Example 5

Preparation of (R)-2-(quinuclidin-3-yl)-2,3,4,5-tetrahydro-1H-[1,5]diazocino[3,2,1-hi]indol-1-one, hydrochloride salt

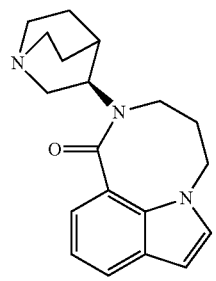 [SMILES: O=C1c2cccc3ccn(c23)CCCN1[C@H]1CN2CCC1CC2]

Step A: To a stirred solution of methyl 1H-indole-7-carboxylate (3.3 g, 18.8 mmol) in DMSO (18 mL) was added potassium tert-butoxide (2.1 g, 18.8 mmol) in portions. After stirring at room temperature for 1 h, a solution of 3-bromo-1,1-dimethoxypropane (10 g, 54.6 mmol) and potassium iodide (188 mg, 1.1 mmol) in DMSO (15 mL) was added and the mixture was stirred for 15 h. The reaction was quenched with saturated aqueous ammonium chloride and adjusted to pH 6. The aqueous phase was extracted with ethyl acetate (3×) and the combined extracts were washed with saturated aqueous sodium bicarbonate and brine, dried over sodium sulfate, filtered, and concentrated under reduced pressure. The crude material was purified by column chromatography (silica gel, 90:10 hexanes/ethyl acetate) to give methyl 1-(3,3-dimethoxypropyl)-1H-indole-7-carboxylate (4.8 g, 92%) as a light yellow oil: $^1$H NMR (500 MHz, CDCl$_3$) δ 7.79 (d, J=7.5 Hz, 1H), 7.68 (d, J=7.5 Hz, 1H), 7.12 (d, J=3.0 Hz, 1H), 7.11 (t, J=7.5 Hz, 1H), 6.56 (d, J=3.5 Hz, 1H), 4.49 (t, J=7.0 Hz, 2H), 4.09 (t, J=6.0 Hz, 1H), 3.97 (s, 3H), 3.25 (s, 6H), 1.97 (q, J=6.0 Hz, 2H).

Step B: A mixture of methyl 1-(3,3-dimethoxypropyl)-1H-indole-7-carboxylate (1.6 g, 5.8 mmol) from Step A above, 2 N HCl (15 mL) and THF (15 mL) were heated at reflux for 4 h. The reaction was quenched with solid sodium bicarbonate and adjusted to pH 8 and the aqueous phase was extracted with ethyl acetate (3×). The combined organics were washed with brine, dried over sodium sulfate, filtered, and concentrated under reduced pressure. The crude material was purified by column chromatography (silica gel, 80:20 hexanes/ethyl acetate) to give methyl 1-(3-oxopropyl)-1H-indole-7-carboxylate (278 mg, 21%) as a colorless oil: $^1$H NMR (500 MHz, CDCl$_3$) δ 9.77 (s, 1H), 7.78 (d, J=8.0 Hz, 1H), 7.73 (d, J=7.5 Hz, 1H), 7.18 (d, J=3.0 Hz, 1H), 7.12 (t, J=8.0 Hz, 1H), 6.57 (d, J=3.0 Hz, 1H), 4.72 (t, J=6.5 Hz, 2H), 3.96 (s, 3H), 2.99 (t, J=6.5 Hz, 2H).

Step C: To a stirred solution of (R)-(+)-3-aminoquinuclidine dihydrochloride (287 mg, 1.4 mmol) in 1,4-dioxane (10 mL) was added 60% sodium hydride (86 mg, 3.6 mmol) in portions. The mixture was heated at 60° C. for 1 h and then a solution of methyl 1-(3-oxopropyl)-1H-indole-7-carboxylate (278 mg, 1.2 mmol) from Step B above in 1,4-dioxane (20 mL) was added, followed by glacial acetic acid (1% of total solvent used). The reaction mixture was stirred at 60° C. for 2 h and cooled to room temperature. Sodium triacetoxyborohydride (763 mg, 3.6 mmol) was then added in portions and the reaction mixture was stirred at room temperature for 4 h. The solvent was removed under reduced pressure and the crude material was purified by column chromatography (silica gel, 80:18:2 methylene chloride/methanol/concentrated ammonium hydroxide) to give (R)-methyl 1-(3-(quinuclidin-3-ylamino)propyl)-1H-indole-7-carboxylate (317 mg, 77%) as a yellow oil: $^1$H NMR (300 MHz, CD$_3$OD) δ 7.78 (d, J=13.0 Hz, 1H), 7.62 (d, J=12.5 Hz, 1H), 7.30 (d, J=5.0 Hz, 1H), 7.10 (t, J=13.0 Hz, 1H), 6.56 (d, J=5.5 Hz, 1H), 4.49 (t, J=11.5 Hz, 2H), 3.96 (s, 3H), 3.07-2.99 (m, 1H), 2.82-2.65 (m, 5H), 2.44-2.27 (m, 3H), 1.89-1.64 (m, 5H), 1.53-1.32 (m, 2H).

Step D: A mixture of (R)-methyl 1-(3-(quinuclidin-3-ylamino)propyl)-1H-indole-7-carboxylate (317 mg, 0.93 mmol) from Step C above and lithium hydroxide monohydrate (117 mg, 2.8 mmol) in tetrahydrofuran/water (1:1, 20 mL) was stirred at reflux until the reaction was complete by LC-MS. The solvent was removed under reduced pressure to give lithium (R)-1-(3-(quinuclidin-3-ylamino)propyl)-1H-indole-7-carboxylate as an off-white solid (574 mg, quantitative yield): $^1$H NMR (500 MHz, CD$_3$OD) δ 7.49 (d, J=7.5 Hz, 1H), 7.26 (d, J=7.0 Hz, 1H), 7.19 (d, J=3.0 Hz, 1H), 6.98 (t, J=7.5 Hz, 1H), 6.43 (d, J=3.0 Hz, 1H), 4.51 (d, J=7.0 Hz, 2H), 3.05-2.99 (m, 1H), 2.83-2.68 (m, 5H), 2.49-2.32 (m, 3H), 2.01-1.92 (m, 2H), 1.71-1.61 (m, 3H), 1.51-1.47 (m, 1H), 1.36-1.28 (m, 1H); MS (ESI+) m/z 328 (M+H).

Step E: A solution of lithium (R)-1-(3-(quinuclidin-3-ylamino)propyl)-1H-indole-7-carboxylate (574 mg, 1.7 mmol) from Step D above in DMF (8 mL) was cooled in an ice bath while N,N-diisopropylethylamine (1.3 g, 10.3 mmol) was added, followed by 1-propanephosphonic acid cyclic anhydride (T3P) (3.3 g, 10.3 mmol). The reaction mixture was stirred at room temperature for 5 h. The reaction was quenched with water and the aqueous phase was extracted with methylene chloride (3×) and the combined extracts were washed with brine, dried over sodium sulfate, filtered, and concentrated under reduced pressure. The crude material was purified by column chromatography (silica gel, 80:18:2 methylene chloride/methanol/concentrated ammonium hydroxide) to give (R)-2-(quinuclidin-3-yl)-2,3,4,5-tetrahydro-1H-[1,5]diazocino[3,2,1-hi]indol-1-one (127 mg, 24%) as an off-white solid: $^1$H NMR (300 MHz, CD$_3$OD) δ 7.67 (d, J=6.6 Hz, 1H), 7.33 (d, J=7.5 Hz, 1H), 7.20 (d; J=3.3 Hz, 1H), 7.11 (t, J=7.8 Hz, 1H), 6.50 (d, J=3.0 Hz, 1H), 4.40-4.20 (m, 2H), 3.80-3.45 (m, 3H), 3.25-2.80 (m, 5H), 2.30-1.50 (m, 6H), 1.40-1.20 (m, 2H); MS (ESI+) m/z 310 (M+H).

Step F: To a stirred solution of (R)-2-(quinuclidin-3-yl)-2,3,4,5-tetrahydro-1H-[1,5]diazocino[3,2,1-hi]indol-1-one (127 mg, 0.4 mmol) from Step E above in methanol was added HCl (1.25 M in methanol) and the solution was concentrated under reduced pressure to give (R)-2-(quinuclidin-3-yl)-2,3,4,5-tetrahydro-1H-[1,5]diazocino[3,2,1-hi]indol-1-one hydrochloride (124 mg, 88%) as an off-white solid: $^1$H NMR (500 MHz, D$_2$O) δ 7.76 (d, J=8.0 Hz, 1H), 7.32 (d, J=7.5 Hz, 1H), 7.24 (d, J=3.0 Hz, 1H), 7.16 (t, J=7.5 Hz, 1H), 6.57 (d, J=3.5 Hz, 1H), 4.31-4.22 (m, 2H), 4.19-4.10 (m, 1H), 3.97-3.90 (m, 1H), 3.84-3.66 (m, 2H), 3.62-3.48 (m, 2H), 3.47-3.22 (m, 4H), 2.58-2.47 (m, 1H), 2.24-1.80 (m, 5H); MS (ESI+) m/z 310 (M+H).

Example 6

Preparation of (S)-2-(quinuclidin-3-yl)-2,3,4,5-tetrahydro-1H-[1,5]diazocino[3,2,1-hi]indol-1-one, hydrochloride salt

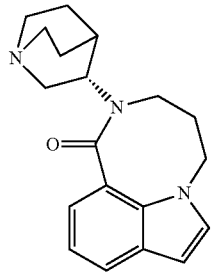 [SMILES: O=C1c2cccc3ccn(c23)CCCN1[C@@H]1CN2CCC1CC2]

Step A: The procedure described in Step C of Example 5 was used to form (S)-methyl 1-(3-(quinuclidin-3-ylamino)propyl)-1H-indole-7-carboxylate from methyl 1-(3-oxopropyl)-1H-indole-7-carboxylate (from Step B of Example 5) and (S)-(−)-3-aminoquinuclidine dihydrochloride, providing the product as a yellow oil: $^1$H NMR (500 MHz, CD$_3$OD) δ 7.78 (d, J=8.0 Hz, 1H), 7.62 (d, J=7.5 Hz, 1H), 7.29 (d, J=3.5 Hz, 1H), 7.09 (t, J=7.5 Hz, 1H), 6.56 (d, J=3.0 Hz, 1H), 4.49-4.45 (m, 2H), 3.96 (s, 3H), 3.05-2.99 (m, 1H), 2.85-2.60 (m, 5H), 2.43-2.36 (m, 1H), 2.35-2.28 (m, 2H), 1.89-1.64 (m, 5H), 1.52-1.44 (m, 1H), 1.40-1.31 (m, 1H); MS (ESI+) m/z 342 (M+H).

Step B: The procedure described in Step D of Example 5 was used to convert (S)-methyl 1-(3-(quinuclidin-3-ylamino)propyl)-1H-indole-7-carboxylate from Step A above to lithium (S)-1-(3-(quinuclidin-3-ylamino)propyl)-1H-indole-7-carboxylate, providing the product as a pale yellow solid: $^1$H NMR (500 MHz, CD$_3$OD) δ 7.49 (d, J=8.0 Hz, 1H), 7.26 (d, J=7.5 Hz, 1H), 7.20 (d, J=3.5 Hz, 1H), 6.98 (t, J=7.0 Hz, 1H), 6.43 (d, J=3.5 Hz, 1H), 4.51 (t, J=7.0 Hz, 2H), 3.05-2.97 (m, 1H), 2.86-2.78 (m, 1H), 2.78-2.62 (m, 4H), 2.49-2.42 (m, 1H), 2.42-2.35 (m, 1H), 2.35-2.29 (m, 1H), 2.00-1.92 (m, 2H), 1.82-1.73 (m, 2H), 1.70-1.62 (m, 1H), 1.54-1.44 (m, 1H), 1.38-1.27 (m, 1H).

Step C: The procedure described in Step E of Example 5 was used to convert lithium (S)-1-(3-(quinuclidin-3-ylamino)propyl)-1H-indole-7-carboxylate from Step B above to (S)-2-(quinuclidin-3-yl)-2,3,4,5-tetrahydro-1H-[1,5]diazocino[3,2,1-hi]indol-1-one, providing the product as an off-white solid: $^1$H NMR (300 MHz, CD$_3$OD) δ 7.66 (d, J=6.3 Hz, 1H), 7.33 (d, J=7.2 Hz, 1H), 7.20 (d, J=3.3 Hz, 1H), 7.11 (t, J=7.8 Hz, 1H), 6.50 (d, J=2.7 Hz, 1H), 4.40-4.25 (m, 2H), 3.80-3.45 (m, 3H), 3.24-3.00 (m, 2H), 2.95-2.90 (m, 3H), 2.25-1.55 (m, 8H); MS (ESI+) m/z 310 (M+H).

Step D: The procedure described in Step F of Example 5 was used to convert (S)-2-(quinuclidin-3-yl)-2,3,4,5-tetrahydro-1H-[1,5]diazocino[3,2,1-hi]indol-1-one from Step C above to the corresponding hydrochloride salt (off-white solid): $^1$H NMR (500 MHz, CD$_3$OD) δ 7.69 (d, J=8.0 Hz, 1H), 7.37 (d, J=7.5 Hz, 1H), 7.22 (d, J=3.0 Hz, 1H), 7.12 (t, J=7.5 Hz, 1H), 6.52 (d, J=3.0 Hz, 1H), 4.38-4.31 (m, 1H), 4.29-4.20 (m, 1H), 4.18-4.12 (m, 1H), 4.07-4.00 (m, 1H), 3.95-3.87 (m, 1H), 3.84-3.60 (m, 3H), 3.50-3.34 (m, 3H), 2.51 (s, 1H), 2.40-2.10 (m, 3H), 2.10-1.90 (m, 3H); MS (ESI+) m/z 310 (M+H).

Example 7

Preparation of (S)-7-(quinuclidin-3-yl)-8,9-dihydro-[1,4]diazepino[6,7,1-hi]indazol-6(7H)-one, hydrochloride salt

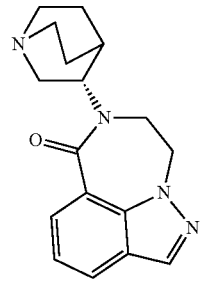 [SMILES: O=C1c2cccc3cnn(c23)CCN1[C@@H]1CN2CCC1CC2]

Step A: To a stirred solution of 2-fluoro-3-methylbenzoic acid (4.0 g, 26.0 mmol) in anhydrous methanol (52 mL) at 0° C. was added thionyl chloride (2.8 mL, 39.0 mmol) dropwise and the reaction mixture was stirred overnight at reflux. The mixture was diluted with methanol and concentrated under reduced pressure to remove the excess thionyl chloride. The residue was then dissolved in ethyl acetate, washed with saturated aqueous sodium bicarbonate, dried (Na$_2$SO$_4$), filtered, and concentrated under reduced pressure to give methyl 2-fluoro-3-methylbenzoate (3.6 g, 83%) as a clear oil that was used in the next step without further purification: $^1$H NMR (500 MHz, CDCl$_3$) δ 7.75-7.72 (m, 1H), 7.38-7.35 (m, 1H), 7.26-7.06 (m, 1H), 3.91 (s, 3H), 2.31 (s, 3H).

Step B: To a mixture of 2-fluoro-3-methylbenzoate (3.6 g, 21.6 mmol) from Step A above and N-bromosuccinimide (4.2 g, 23.8 mmol) in carbon tetrachloride (58 mL) at room temperature was added benzoyl peroxide (10 mg, cat) and the mixture was heated at reflux for 2.5 h. After the starting material was consumed, the crude reaction was concentrated under reduced pressure and purified by column chromatography (silica gel, 0% to 1% ethyl acetate in hexanes) to afford methyl 3-(bromomethyl)-2-fluorobenzoate (3.6 g, 67%): $^1$H NMR (500 MHz, CDCl$_3$) δ 7.92-7.88 (m, 1H), 7.60-7.58 (m, 1H), 7.21-7.18 (m, 1H), 4.53 (s, 2H), 3.94 (s, 3H).

Step C: Dimethylsulfoxide was degassed with argon for 1 h. Methyl 3-(bromomethyl)-2-fluorobenzoate (3.6 g, 14.5 mmol) from Step B above and solid sodium bicarbonate (10.5 g, 124.6 mmol) were added to the DMSO and the mixture was heated at 115° C. for 2 h. The reaction mixture was then diluted with ethyl acetate, washed with brine, dried (Na$_2$SO$_4$), filtered, concentrated under reduced pressure and purified by column chromatography (silica gel, 0% to 2% ethyl acetate in hexanes) to give methyl 2-fluoro-3-formylbenzoate (1.8 g, 67%): $^1$H NMR (500 MHz, CDCl$_3$) δ 10.43 (s, 1H), 8.22-8.19 (m, 1H), 8.09-8.06 (m, 1H), 7.37-7.34 (m, 1H), 3.98 (s, 3H).

Step D: To a stirred solution of 2-fluoro-3-formylbenzoate (0.5 g, 2.8 mmol) in methanol (4 mL) was added 2-hydrazinoethanol (0.2 mL, 2.8 mmol) and the mixture was stirred at room temperature. After the starting material was consumed, the solution was transferred to a microwave tube and microwaved at 150° C. for 5 h. The crude reaction was diluted with ethyl acetate, washed with water, dried (Na$_2$SO$_4$), filtered, concentrated under reduced pressure and purified by column chromatography (silica gel, 0% to 50% ethyl acetate in hexanes) to afford methyl 1-(2-hydroxyethyl)-1H-indazole-7-carboxylate (0.6 g, 95%): $^1$H NMR (500 MHz, CDCl$_3$) δ 8.04-8.02 (m, 1H), 8.00-7.98 (m, 1H), 7.95-7.93 (m, 1H), 4.87-4.80 (m, 2H), 4.14-4.10 (m, 2H), 3.99 (s, 3H); MS (ESI+) m/z 221 (M+H).

Step E: To a stirred solution of DMSO (0.4 mL, 5.2 mmol) and methylene chloride (2 mL) at −78° C. was added oxalyl chloride (0.3 mL, 3.1 mmol) dropwise. After 20 min, a solution of methyl 1-(2-hydroxyethyl)-1H-indazole-7-carboxylate (0.6 g, 2.6 mmol) from Step D above in methylene chloride (17 mL) was added and the mixture was stirred at −78° C. for 1.5 h. After N,N-diisopropylethylamine was added, the reaction was cooled to 0° C. and quenched with saturated aqueous ammonium chloride. The aqueous layer was extracted with methylene chloride and the organic extracts were dried (Na$_2$SO$_4$), filtered, concentrated under reduced pressure and purified by preparatory thin layer chromatography (30% ethyl acetate in hexanes) to give methyl 1-(2-oxoethyl)-1H-indazole-7-carboxylate (0.3 g, 53%): $^1$H NMR (500 MHz, CDCl$_3$) δ 9.79 (s, 1H), 8.16 (s, 1H), 8.10-8.09 (m, 1H), 7.99-7.97 (m, 1H), 7.25-7.21 (m, 1H), 5.61 (s, 2H), 3.92 (s, 3H).

Step F: To a stirred solution of (S)-(−)-3-aminoquinuclidine dihydrochloride (0.3 g, 1.3 mmol) in THF (13 mL) was added sodium hydride (0.1 g, 2.7 mmol) and the mixture was stirred for 1.5 h. Acetic acid (0.5 mL) and sodium triacetoxyborohydride (380 mg, 1.8 mmol) were added and stirred for 0.5 h. A solution of methyl 1-(2-oxoethyl)-1H-indazole-7-carboxylate (0.3 g, 1.3 mmol) from Step E above in THF (13 mL) was added dropwise, and the resulting suspension was stirred overnight at ambient temperature. The solvent was removed under reduced pressure, and the crude material was purified by preparative thin layer chromatography (90:9:1 methylene chloride/methanol/concentrated ammonium hydroxide) to afford (S)-methyl 1-(2-(quinuclidin-3-ylamino)ethyl)-1H-indazole-7-carboxylate: $^1$H NMR (500 MHz, DMSO-d$_6$) δ 8.25 (s, 1H), 8.03 (dd, J=8.0, 1.0 Hz, 1H), 7.85 (dd, J=7.0, 1.0 Hz, 1H), 7.22 (t, J=7.5 Hz, 1H), 4.68-4.65 (m, 2H), 3.94 (s, 3H), 2.84-2.70 (m, 3H), 2.64-2.45 (m, 2H), 2.03-1.99 (m, 2H), 1.86-1.75 (m, 2H), 1.58-1.51 (m, 3H), 1.45-1.32 (m, 1H), 1.08-1.01 (m, 1H); MS (ESI+) m/z 329 (M+H).

Step G: To a stirred solution of (S)-methyl 1-(2-(quinuclidin-3-ylamino)ethyl)-1H-indazole-7-carboxylate (370 mg, 1.12 mmol) from Step F above in tetrahydrofuran (5 mL) was added lithium hydroxide monohydrate (142 mg, 3.4 mmol), water (5 mL) and methanol (5 mL). The mixture was stirred at room temperature for 17 h and then concentrated under reduced pressure. The residue was co-evaporated with toluene (2×10 mL) and dried overnight under vacuum to afford crude lithium (S)-1-(2-(quinuclidin-3-ylamino)ethyl)-1H-indazole-7-carboxylate (360 mg, quantitative yield) which was used in the next step without further purification: $^1$H NMR (500 MHz, DMSO-d$_6$) δ 7.97 (s, 1H), 7.53 (dd, J=8.0, 1.0 Hz, 1H), 7.32 (dd, J=6.5, 1.0 Hz, 1H), 6.96 (t, J=7.0 Hz, 1H), 4.85-4.75 (m, 2H), 4.50-3.50 (br s 2H), 2.90-2.70 (m, 3H), 2.65-2.45 (m, 4H), 2.11-2.07 (m, 1H), 1.68-1.65 (m, 2H), 1.51-1.46 (m, 1H), 1.31-1.26 (m, 1H), 1.10-1.06 (m, 1H); MS (ESI+) m/z 315 (M+H).

Step H: To a suspension of lithium (S)-1-(2-(quinuclidin-3-ylamino)ethyl)-1H-indazole-7-carboxylate (360 mg, 1.1 mmol) from Step G above in THF (50 mL) was added N,N-diisopropylethylamine (1.2 mL, 6.7 mmol) and the mixture was at ambient temperature for 10 min. To the above reaction mixture was added 1-propanephosphonic acid cyclic anhydride (T3P) (3.6 g, 5.6 mmol) and the reaction was stirred for 2.5 h. The reaction was quenched with saturated aqueous sodium bicarbonate (100 mL), extracted with ethyl acetate (3×250 mL), and the combined organic layers were washed with brine, dried (Na$_2$SO$_4$), filtered, and concentrated under reduced pressure. The crude solid was purified by SCX-2 resin to afford (S)-7-(quinuclidin-3-yl)-8,9-dihydro-[1,4]diazepino[6,7,1-hi]indazol-6(7H)-one (207 mg, 63%): $^1$H NMR (500 MHz, CD$_3$OD) δ 8.17 (dd, J=7.5, 1.0 Hz, 1H), 8.15 (s, 1H), 8.00 (dd, J=8.0, 1.0 Hz, 1H), 7.31 (t, J=8.0 Hz, 1H), 4.80-4.75 (m, 2H), 4.70-3.80 (m 3H), 3.38-3.34 (m, 1H), 3.20-3.05 (m, 2H), 2.96-2.85 (m, 3H), 2.14-2.00 (m, 1H), 1.95-1.65 (m, 4H); MS (ESI+) m/z 297 (M+H).

Step I: To a stirred solution of (S)-7-(quinuclidin-3-yl)-8,9-dihydro-[1,4]diazepino[6,7,1-hi]indazol-6(7H)-one (207 mg, 0.7 mmol) from Step H above in methanol (5 mL) was added hydrochloric acid (1.25 M solution in methanol, 1.1 mL, 1.4 mmol) at room temperature. The mixture was stirred for 5 min, concentrated under reduced pressure and diluted with diethyl ether to afford (S)-7-(quinuclidin-3-yl)-8,9-dihydro-[1,4]diazepino[6,7,1-hi]indazol-6(7H)-one hydrochloride as a white solid: $^1$H NMR (500 MHz, DMSO-d$_6$) δ 10.24 (bs, 1H), 8.24 (s (1H), 8.10 (dd, J=7.0, 0.5 Hz, 1H), 8.04 (dd, J=8.0, 1.0 Hz, 1H), 7.30 (t, J=7.5 Hz, 1H), 4.80-4.60 (m, 3H), 4.30-3.90 (m, 2H), 3.70 (t, J=12.0 Hz, 1H), 3.60-3.45 (m, 2H), 3.30-3.05 (m, 3H), 2.40-2.35 (m, 1H), 2.10-1.80 (m, 4H): MS (ESI+) m/z 297 (M+H).

Example 8

Preparation of (S)-4-chloro-7-(quinuclidin-3-yl)-8,9-dihydro-[1,4]diazepino[6,7,1-hi]indazol-6(7H)-one hydrochloride

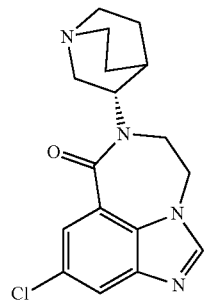 [SMILES: O=C1c2cc(Cl)cc3ncn(c23)CCN1[C@@H]1CN2CCC1CC2]

Step A: Methyl 2-amino-5-chloro-3-methylbenzoate (6.6 g, 33.1 mmol) was dissolved in CHCl$_3$ (90 mL) then cooled in an icebath while acetic anhydride (7.2 mL, 76.1 mmol) was added dropwise. After the addition was complete, the reaction mixture was stirred at room temperature for ca. 1 h, then KOAc (650 mg, 6.6 mmol) was added, followed by isoamyl nitrite (9.7 mL, 72.8 mmol). The reaction mixture was heated under reflux until the reaction was complete by TLC (overnight). While cooling to room temperature, precipitation was observed. The precipitate was collected and dried to afford methyl 5-chloro-1H-indazole-7-carboxylate as a yellow solid (4.83 g, 69%): $^1$H NMR (300 MHz, CDCl$_3$) δ 11.25 (s, 1H), 8.10 (s, 1H), 8.05 (s, 3H), 7.97 (s, 1H), 4.09 (s, 1H); MS (ESI+) m/z 211 (M+H).

Step B: Methyl 5-chloro-1H-indazole-7-carboxylate (2.65 g, 12.6 mmol; 1 eq) from Step A above was stirred in DMSO (25 mL) at room temperature while bromoacetaldehyde dimethyl acetal (3 mL, 25.2 mmol) pre-mixed with potassium iodide (209 mg, 1.3 mmol) was added. 1,8-diazabicyclo[5.4.0]undec-7-ene (DBU; 2 mL, 12.6 mmol) was then added dropwise. The reaction mixture was stirred at 80° C. (external temperature) overnight. The reaction mixture was neutralized with sat. $NH_4Cl$ then partitioned between $H_2O$ and ethyl acetate. The ethyl acetate layers were combined, dried ($Na_2SO_4$), filtered, concentrated and purified by column chromatography (silica gel, 1:1 ethyl acetate/hexanes) to afford methyl 5-chloro-1-(2,2-dimethoxyethyl)-1H-indazole-7-carboxylate as a light yellow oil (404 mg, 11%, regioisomer confirmed by NOE): $^1$H NMR (300 MHz, $CDCl_3$) δ 8.04 (s, 1H), 8.84 (s, 2H), 4.93 (d, J=5.1 Hz, 2H), 4.50 (t, J=5.1 Hz, 1H), 3.99 (s, 3H), 3.27 (s, 6H). [1.29 g starting material recovered; 846 mg, 22% undesired regioisomer methyl 5-chloro-2-(dimethoxymethyl)-2H-indazole-7-carboxylate collected as side product, dark yellow solid]

Step C: Methyl 5-chloro-1-(2,2-dimethoxyethyl)-1H-indazole-7-carboxylate (733 mg, 2.5 mmol) from Step B above was refluxed in 2 N HCl (8 mL) and THF (8 mL) until the reaction was complete by TLC (3-5 h). After cooling to room temperature, the pH of the reaction mixture was adjusted to 8 with $NaHCO_3$, then extracted with ethyl acetate. The organic layers were combined, dried ($Na_2SO_4$), filtered, concentrated and purified by column chromatography (silica gel, 1:1 ethyl acetate/hexanes) to afford methyl 5-chloro-1-(2-oxoethyl)-1H-indazole-7-carboxylate as an off-white solid (472 mg, 76%): $^1$H NMR (300 MHz, $CDCl_3$) δ 9.77 (s, 1H), 8.10 (s, 1H), 8.05 (s, 1H), 7.94 (s, 1H), 5.60 (s, 2H), 4.03 (d, J=8.4 Hz, 1H), 3.93 (s, 3H); MS (ESI+) m/z 253 (M+H).

Step D: (S)-Quinuclidin-3-amine dihydrochloride (355 mg, 1.8 mmol) was stirred in MeOH (5 mL) at room temperature while sodium methoxide (25 wt % in MeOH, 0.8 mL, 3.6 mmol) was added dropwise. The reaction mixture was stirred at room temperature for 1 h. Glacial acetic acid (0.2 mL, 4.1 mmol) was added to neutralize the basicity of the mixture. Sodium cyanoborohydride (224 mg, 3.6 mmol) was added, followed by methyl 5-chloro-1-(2-oxoethyl)-1H-indazole-7-carboxylate (472 mg, 1.9 mmol) from Step C above in MeOH (8 mL). The mixture was stirred at room temperature until the reaction was complete by TLC (1-2 h). The reaction mixture was concentrated and absorbed onto silica gel and purified by column chromatography (80:18:2 methylene chloride/methanol/concentrated ammonium hydroxide) to afford (S)-methyl 5-chloro-1-(2-(quinuclidin-3-ylamino)ethyl)-1H-indazole-7-carboxylate as a light yellow solid (525 mg, 77%): $^1$H NMR (500 MHz, $CD_3OD$) δ 8.17 (s, 1H), 8.03 (s, 1H), 7.92 (s, 1H), 4.80 (t, J=6.5 Hz, 2H), 4.02 (s, 3H), 3.50-3.38 (m, 1H), 3.25-3.05 (m, 4H), 3.05-2.90 (m, 3H), 2.65-2.55 (m, 1H), 2.10-2.00 (m, 1H), 2.00-1.90 (m, 2H), 1.90-1.75 (m, 2H), 1.65-1.55 (m, 1H); MS (ESI+) m/z 363 (M+H).

Step E: A mixture of (S)-methyl 5-chloro-1-(2-(quinuclidin-3-ylamino)ethyl)-1H-indazole-7-carboxylate (525 mg, 1.5 mmol) from Step D above and lithium hydroxide monohydrate (183 mg, 4.4 mmol) in tetrahydrofuran/water (14 mL, 1:1) was stirred at room temperature until the reaction was complete by TLC (2-3 h). The solvent was removed under reduced pressure to give lithium (S)-5-chloro-1-(2-(quinuclidin-3-ylamino)ethyl)-1H-indazole-7-carboxylate as a green solid (641 mg, 100%): $^1$H NMR (300 MHz, $CD_3OD$) δ 8.01 (s, 1H), 7.71 (s, 1H), 7.48 (s, 1H), 4.80 (t, J=6.6 Hz, 2H), 3.10-2.96 (m, 2H), 2.95-2.88 (m, 1H), 2.80-2.58 (m, 5H), 2.33-2.27 (m, 1H), 1.80-1.76 (m, 1H), 1.72-1.60 (m, 2H), 1.60-1.40 (m, 1H), 1.40-1.20 (m, 2H); MS (ESI+) m/z 349 (M+H).

Step F: Lithium (S)-5-chloro-1-(2-(quinuclidin-3-ylamino)ethyl)-1H-indazole-7-carboxylate (641 mg, 1.8 mmol) from Step E above in THF (12 mL) was cooled in an ice bath while N,N-diisopropylethylamine (2 mL, 10.8 mmol) was added, followed by 1-propanephosphonic acid cyclic anhydride ($T_3P$; 50 wt % in ethyl acetate; 7 mL, 10.8 mmol). The reaction mixture was stirred at room temperature until the reaction was complete by TLC (30 min). The mixture was concentrated into a yellow oil, diluted in MeOH, and purified by ISOLUTE® SCX-2 columns (4×5 g column) to afford (S)-4-chloro-7-(quinuclidin-3-yl)-8,9-dihydro-[1,4]diazepino[6,7,1-hi]indazol-6(7H)-one as an off-white solid (505 mg, 85%): $^1$H NMR (500 MHz, $CD_3OD$) δ 8.12 (s, 1H), 8.10 (s, 1H), 8.01 (s, 1H), 4.77-4.50 (m, 3H), 4.20-3.95 (m, 1H), 3.22-3.05 (m, 3H), 3.00-2.85 (m, 4H), 2.14 (s, 1H), 1.96-1.85 (m, 2H), 1.85-1.75 (m, 1H), 1.75-1.60 (m, 1H); MS (ESI+) m/z 331 (M+H).

Step G: (S)-4-chloro-7-(quinuclidin-3-yl)-8,9-dihydro-[1,4]diazepino[6,7,1-hi]indazol-6(7H)-one (428 mg, 1.30 mmol) from Step F above was dissolved in 1.25 M HCl in $CH_3OH$ and concentrated under reduced pressure. The resulting yellow-green solid was triturated (MeOH/DCM/diethyl ether), filtered and dried under high vacuum to give (S)-4-chloro-7-(quinuclidin-3-yl)-8,9-dihydro-[1,4]diazepino[6,7,1-hi]indazol-6(7H)-one hydrochloride as a yellow solid (359 mg, 31%): $^1$H NMR (500 MHz, $D_2O$) δ 7.81 (s, 1H), 7.68 (s, 2H), 4.43-4.20 (m, 3H), 3.80-3.65 (m, 1H), 3.65-3.50 (m, 1H), 3.40-3.20 (m, 2H), 3.20-3.00 (m, 4H), 2.26 (s, 1H), 2.00-1.70 (m, 4H); MS (ESI+) m/z 331 (M+H).

Example 9

Preparation of (S)-4-fluoro-7-(quinuclidin-3-yl)-8,9-dihydro-[1,4]diazepino[6,7,1-hi]indazol-6(7H)-one hydrochloride

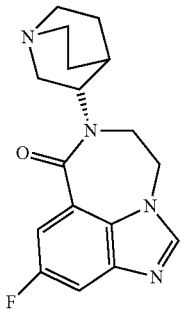

Step A: At 0° C., to 3-fluoro-5-methylbenzoic acid (8.0 g, 52 mmol) was added con. $H_2SO_4$ (60 ml) followed by $KNO_3$ (5.8 g, 57 mmol). The reaction solution was then warmed to ambient temperature and stirred for 1 h. The reaction mixture was poured into ice water to precipitate 5-fluoro-3-methyl-2-nitrobenzoic acid as a white solid after filtration (8.0 g, 77%): $^1$H NMR (500 MHz, $CDCl_3$) δ 7.63 (dd, J=8.0 Hz, 3.0 Hz, 1H), 7.27 (dd, J=8.0 Hz, 3.0 Hz, 1H); MS (ESI+) m/z 200 (M+H).

Step B: To a solution of 5-fluoro-3-methyl-2-nitrobenzoic acid (8.0 g, 40 mmol) from Step A above in DMF (100 mL) was added cesium carbonate (20.0 g, 60 mmol) followed by iodomethane (3.0 ml, 48 mmol). The reaction solution was stirred at ambient temperature overnight. The reaction mixture was diluted with water and extracted with ethyl acetate. The organic extract was separated, washed with brine, dried ($Na_2SO_4$), and concentrated in vacuo to afford methyl 5-fluoro-3-methyl-2-nitrobenzoate (8.4 g, 98%) as a yellow solid: ¹H NMR (500 MHz, DMSO-d₆) δ 7.71-7.67 (m, 2H), 3.85 (s, 3H), 2.32 (s, 3H); MS (ESI+) m/z 214 (M+H).

Step C: A solution of methyl 5-fluoro-3-methyl-2-nitrobenzoate (8.4 g, 39.4 mmol) from Step B above in methanol (150 mL) was purged with nitrogen. Palladium on charcoal was added to the solution and hydrogenation was carried out for 24 h at 1 atm. The reaction mixture was filtered through a pad of Celite and washed with methanol. The filtrate was concentrated in vacuo to afford methyl 2-amino-5-fluoro-3-methylbenzoate (6.8 g, 94%) as a white solid. ¹H NMR (500 MHz, DMSO-d₆) δ 7.32 (dd, J=10.0, 3.0 Hz, 1H), 7.17 (dd, J=9.0, 3.0 Hz, 1H), 6.40 (s, 2H), 3.80 (s, 3H), 2.13 (s, 3H); MS (ESI+) m/z 184 (M+H).

Step D: To a solution of methyl 2-amino-5-fluoro-3-methylbenzoate (1.0 g, 5.5 mmol) from Step C above in chloroform (15 mL) was added acetic anhydride (1.2 ml) while maintaining the temperature below 40° C. The reaction mixture was stirred at room temperature for 90 min then potassium acetate (157 mg, 1.6 mmol) and isoamyl nitrite (1.62 ml, 12 mmol) were added to it. The reaction mixture was heated to reflux for overnight. The reaction mixture was cooled to room temperature, extracted with dichlormethane, washed with water, saturated sodium bicarbonate and brine. The organic extract was dried (Na₂SO₄) and concentrated in vacuo to afford a red solid, which was purified by column chromatography (silica gel, 0-50% ethyl acetate/hexanes) to afford methyl 5-fluoro-1H-indazole-7-carboxylate (455 mg, 43%) as a yellow brown solid: ¹H NMR (500 MHz, CDCl₃) δ 8.25 (s, 1H), 7.96 (dd, J=9.0, 3.0 Hz, 1H), 7.81 (dd, J=9.0, 3.0 Hz, 1H), 3.98 (s, 3H); MS (ESI+) m/z 195.

Step E: The procedure described in Step B of Example 8 was used to convert methyl 5-fluoro-1H-indazole-7-carboxylate from Step D above to methyl 1-(2,2-dimethoxyethyl)-5-fluoro-1H-indazole-7-carboxylate (105 mg, 15%). ¹H NMR (500 MHz, CDCl₃) δ 8.08 (s, 1H), 7.66 (dd, J=10.0, 3.0 Hz, 1H), 7.51 (dd, J=9.0, 3.0 Hz, 1H), 4.93 (d, J=5.0 Hz, 2H), 4.51 (t, J=5.0 Hz, 1H), 3.93 (s, 3H), 331 (s, 6H); MS (ESI+) m/z 283 (M+H).

Step F: The procedure described in Step C of Example 8 was used to convert methyl 1-(2,2-dimethoxyethyl)-5-fluoro-1H-indazole-7-carboxylate from Step E above to methyl 5-fluoro-1-(2-oxoethyl)-1H-indazole-7-carboxylate: MS (ESI+) m/z 237 (M+H).

Step G: The procedure described in Step D of Example 8 was used to convert methyl 5-fluoro-1-(2-oxoethyl)-1H-indazole-7-carboxylate from Step F above to (S)-methyl 3-(2-(quinuclidin-3-ylamino)ethyl)-1H-indazole-4-carboxylate (40 mg, 61%) as a light yellow liquid: MS (ESI+) m/z 329 (M+H).

Step H: The procedure described in Step E of Example 8 was used to convert (S)-methyl 3-(2-(quinuclidin-3-ylamino)ethyl)-1H-indazole-4-carboxylate from Step G above to lithium (S)-3-(2-(quinuclidin-3-ylamino)ethyl)-1H-indazole-4-carboxylate: MS (ESI+) m/z 314 (M+H).

Step I: The procedure described in Step F of Example 8 was used to convert lithium (S)-3-(2-(quinuclidin-3-ylamino)ethyl)-1H-indazole-4-carboxylate from Step H above to (S)-4-fluoro-7-(quinuclidin-3-yl)-8,9-dihydro-[1,4]diazepino[6,7,1-hi]indazol-6(7H)-one, which was treated immediately with hydrochloric acid following the procedure described in Step G of Example 8 to afford (S)-4-fluoro-7-(quinuclidin-3-yl)-8,9-dihydro-[1,4]diazepino[6,7,1-hi]indazol-6(7H)-one hydrochloride (30 mg, 71%) as a white solid: ¹H NMR (500 MHz, CD₃OD) δ 8.13 (s, 1H), 7.93 (dd, J=10.0, 3.0, 1H), 7.71 (dd, J=9.0, 3.0 Hz, 1H), 4.74 (t, J=4.0 Hz, 2H), 4.60 (bs, 1H), 4.30 (bs, 1H), 4.03 (bs, 1H), 3.68 (s, 1H), 3.19-3.14 (m, 2H), 2.99-2.91 (m, 3H), 2.16 (dd, J=6.0, 2.0 Hz, 1H), 1.91-1.88 (m, 2H), 1.82-1.80 (m, 1H), 1.68 (s, 1H); MS (ESI+) m/z 315 (M+H).

Example 10

Preparation of (S)-4-methoxy-7-(quinuclidin-3-yl)-8,9-dihydro-[1,4]diazepino[6,7,1-hi]indazol-6(7H)-one hydrochloride

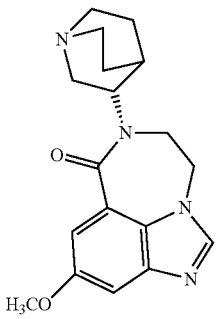

Step A: To a solution of 2-amino-3-methylbenzoic acid (10.0 g, 66 mmol) in DMSO was added 48% aqueous hydrogen bromide (18.0 ml). The reaction solution was stirred at room temperature overnight and then quenched with saturated sodium bicarbonate. The resultant mixture was stirred overnight. Precipitation was collected by filtration and dried in vacuo to give 2-amino-5-bromo-3-methylbenzoic acid (13.0 g, 85%) as a pink solid: ¹H NMR (500 MHz, DMSO) δ 7.69 (d, J=1.0 Hz, 1H), 7.33 (d, J=1.0 Hz, 1H), 2.10 (s, 3H); MS (ESI+) m/z 231 (M+H).

Step B: To a solution of 2-amino-5-bromo-3-methylbenzoic acid (3.0 g, 13 mmol) from Step A above in DMF was added cesium carbonate (6.4 g, 20 mmol) followed by iodomethane (0.8 ml, 13 mmol). The reaction was stirred at ambient temperature overnight. The mixture was washed with water and extracted with dichloromethane. The organic extract was dried (Na₂SO₄) and concentrated in vacuo to afford methyl 2-amino-5-bromo-3-methylbenzoate (3.2 g, 100%) as a grey solid: ¹H NMR (500 MHz, CDCl₃) δ 7.89 (d, J=2.4 Hz, 1H), 7.28 (d, J=2.1 Hz, 1H), 5.84 (brs, 2H), 3.87 (s, 3H), 2.15 (s, 3H); MS (ESI+) m/z 245 (M+H).

Step C: The procedure described in Step A of Example 8 was used to convert methyl 2-amino-5-bromo-3-methylbenzoate (2.3 g, 10 mmol) from Step B above to methyl 5-bromo-1H-indazole-7-carboxylate (2.2 g, 88%) as a white solid: ¹H NMR (500 MHz, CDCl₃) δ 11.25 (br s, 1H), 8.16 (d, J=1.5 Hz, 1H), 8.13 (t, J=1.5 Hz, 1H), 8.09 (d, J=1.5 Hz, 1H), 4.04 (s, 3H); MS (ESI+) m/z 256 (M+H).

Step D: The procedure described in Step B of Example 8 was used to convert methyl 5-bromo-1H-indazole-7-carboxylate (4.0 g, 16 mmol) from Step C above to methyl 5-bromo-1-(2,2-dimethoxyethyl)-1H-indazole-7-carboxylate (1.1 g, 20%) as a light transparent liquid: ¹H NMR (500 MHz, CDCl₃) δ 8.03 (s, 1H), 8.00 (d, J=2.0 Hz, 1H), 7.95 (d, J=2.0 Hz, 1H), 4.92 (d, J=5.5 Hz, 2H), 4.50 (t, J=5.5 Hz, 1H), 3.99 (s, 3H), 3.27 (s, 6H); MS (ESI+) m/z 230 (M+H).

Step E: To a solution of methyl 5-bromo-1-(2,2-dimethoxyethyl)-1H-indazole-7-carboxylate (500 mg, 1.5 mmol) from Step D above in DMSO (4 ml) was added potassium acetate (646 mg, 6.6 mmol) at room temperature under argon, followed by pinacolodiboron (445 mg, 1.8 mmol) and dichloro[1,1'bis(diphenylphosphino)ferrocene]palladium (II) dichloromethane adduct (53 mg, 0.07 mmol). The reaction vessel was evacuated and purged with argon. The reaction mixture was heated at 80° C. overnight, then allowed to cool to room temperature and concentrated in vacuo. The reaction mixture was diluted with water and diethyl ether and filtered through Celite. The filtrate obtained was extracted with diethyl ether and the organic layer was dried (Na$_2$SO4), filtered, and concentrated in vacuo. The residue obtained was purified by column chromatography (silica gel, 0-30% ethyl acetate/hexanes) to afford methyl 1-(2,2-dimethoxyethyl)-5-(4,4,5,5-tetramethyl-1,3,2-dioxaborolan-2-yl)-1H-indazole-7-carboxylate (287 mg, 50%): $^1$H NMR (500 MHz, CDCl$_3$) δ 8.38 (d, J=1.0 Hz, 1H), 8.27 (d, J=1.0 Hz, 1H), 8.10 (s, 1H), 4.95 (d, J=5.5 Hz, 2H), 4.54 (t, J=5.5 Hz, 1H), 3.98 (s, 3H), 3.26 (s, 6H), 1.37 (s, 12H); MS (ESI+) m/z 391 (M+H).

Step F: At room temperature, to a solution of methyl 1-(2,2-dimethoxyethyl)-5-(4,4,5,5-tetramethyl-1,3,2-dioxaborolan-2-yl)-1H-indazole-7-carboxylate (287 mg, 0.7 mmol) from Step E above in methanol (12 ml) was added 30% hydrogen peroxide (20.0 eq). The reaction mixture was stirred for 3 h, and then quenched with aqueous sodium sulfite. The mixture was extracted with ethyl acetate and washed with water. The organic extract was concentrated in vacuo to give methyl 1-(2,2-dimethoxyethyl)-5-hydroxy-1H-indazole-7-carboxylate as a white solid: $^1$H NMR (500 MHz, CDCl$_3$) δ 7.96 (s, 1H), 7.50 (d, J=2.5 Hz, 1H), 7.24 (d, J=2.5 Hz, 1H), 4.90 (d, J=5.5 Hz, 2H), 4.86 (s, 1H), 4.52 (t, J=5.5 Hz, 1H), 3.97 (s, 3H), 3.27 (s, 6H); MS (ESI+) m/z 249 (M+H).

Step G: To a solution of methyl 1-(2,2-dimethoxyethyl)-5-hydroxy-1H-indazole-7-carboxylate (180 mg, 0.6 mmol) from Step F above in DMF (10 ml) was added cesium carbonate (313 mg, 1.0 mmol) followed by iodomethane (40 μL, 0.64 mmol) and the reaction was stirred overnight. The reaction mixture was extracted with ethyl acetate, washed with water, dried (Na$_2$SO4), and concentrated in vacuo to afford methyl 1-(2,2-dimethoxyethyl)-5-methoxy-1H-indazole-7-carboxylate (180 mg, 96%): $^1$H NMR (500 MHz, CDCl$_3$) δ 7.98 (s, 1H), 7.56 (d, J=2.5 Hz, 1H), 7.25 (d, J=2.5 Hz, 1H), 4.90 (d, J=5.0 Hz, 2H), 4.51 (d, J=5.0 Hz, 1H), 3.97 (s, 3H), 3.87 (s, 3H), 3.27 (s, 6H); MS (ESI+) m/z 295 (M+H).

Step H: To methyl 1-(2,2-dimethoxyethyl)-5-methoxy-1H-indazole-7-carboxylate (161 mg, 0.5 mmol) from Step G above in 1,4-dioxane (3 ml) was added 2N hydrogen chloride (3 ml) and the reaction mixture was heated to 75° C. for 2 h. The solvent was concentrated in vacuo to afford methyl 5-methoxy-1-(2-oxoethyl)-1H-indazole-7-carboxylate: MS (ESI+) m/z 249 (M+H).

Step I: The procedure described in Step D of Example 8 was used to convert methyl 5-methoxy-1-(2-oxoethyl)-1H-indazole-7-carboxylate from Step H above to (S)-methyl 6-methoxy-3-(2-(quinuclidin-3-ylamino)ethyl)-1H-indazole-4-carboxylate (250 mg, 66%) as a light yellow liquid: MS (ESI+) m/z 359 (M+H).

Step J: The procedure described in Step E of Example 8 was used to convert (S)-methyl 6-methoxy-3-(2-(quinuclidin-3-ylamino)ethyl)-1H-indazole-4-carboxylate from Step I above to lithium (S)-6-methoxy-3-(2-(quinuclidin-3-ylamino)ethyl)-1H-indazole-4-carboxylate: MS (ESI+) m/z 344 (M+H).

Step K: The procedure described in Step F of Example 8 was used to convert lithium (S)-6-methoxy-3-(2-(quinuclidin-3-ylamino)ethyl)-1H-indazole-4-carboxylate from Step J above to (S)-4-methoxy-7-(quinuclidin-3-yl)-8,9-dihydro-[1,4]diazepino[6,7,1-hi]indazol-6(7H)-one, which was treated immediately with hydrochloric acid following the procedure described in Step G of Example 8 to afford (S)-4-methoxy-7-(quinuclidin-3-yl)-8,9-dihydro-[1,4]diazepino [6,7,1-hi]indazol-6(7H)-one hydrochloride (60 mg, 39%) as a white solid: $^1$H NMR (500 MHz, CD$_3$OD) δ 8.05 (s, 1H), 7.83 (dd, J=2.5 Hz, 1H), 7.50 (d, J=2.0 Hz, 1H), 4.72-4.65 (m, 3H), 4.14-4.00 (m, 2H), 3.89 (s, 3H), 3.86-3.71 (m, 2H), 3.45-3.35 (m, 4H), 2.54 (d, J=2.5 Hz, 1H), 2.28 (brs 1H), 2.15-2.11 (m, 2H), 2.20-1.99 (m, 1H); MS (ESI+) m/z 327 (M+H).

Example 11

Preparation of (S)-4-methyl-7-(quinuclidin-3-yl)-8,9-dihydro-[1,4]diazepino[6,7,1-hi]indazol-6(7H)-one hydrochloride

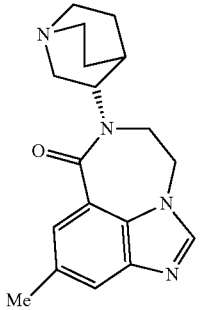

Step A: To methyl 5-bromo-1-(2,2-dimethoxyethyl)-1H-indazole-7-carboxylate from Step D of Example 10 in DMF (100 mL) was added potassium carbonate (622 mg, 4.5 mmol), tetrakis(triphenylphosphine)palladium(0) (347 mg, 0.3 mmol) and trimethylboroxine (377 mg, 3.0 mmol) and the reaction mixture was stirred at 100° C. for 24 h. Then another portion of trimethylboroxine (377 mg, 3 mmol) was added and the reaction was further stirred for 6 h. Ethyl acetate was added and the reaction was washed with water and concentrated in vacuo. The crude mixture was purified by column chromatography (silica gel, 0-30% ethyl acetate/hexanes) to afford methyl 1-(2,2-dimethoxyethyl)-5-methyl-1H-indazole-7-carboxylate (213 mg, 51%) as a white solid: $^1$H NMR (500 MHz, CDCl$_3$) δ 8.00 (s, 1H), 7.73 (s, 1H), 7.65 (s, 1H), 4.92 (d, J=5.5 Hz, 2H), 4.54 (t, J=5.5 Hz, 1H), 3.98 (s, 3H), 3.28 (s, 6H), 2.47 (s, 3H); MS (ESI+) m/z 279 (M+H).

Step B: The procedure described in Step C of Example 8 was used to convert methyl 1-(2,2-dimethoxyethyl)-5-methyl-1H-indazole-7-carboxylate (213 mg, 0.8 mmol) from Step A above to methyl 5-methyl-1-(2-oxoethyl)-1H-indazole-7-carboxylate: MS (ESI+) m/z 233 (M+H).

Step C: The procedure described in Step D of Example 8 was used to convert methyl 1-(2,2-dimethoxyethyl)-5-methyl-1H-indazole-7-carboxylate from Step B above to (S)-methyl 6-methyl-3-(2-(quinuclidin-3-ylamino)ethyl)-1H-indazole-4-carboxylate: MS (ESI+) m/z 343 (M+H).

Step D: The procedure described in Step E of Example 8 was used to convert (S)-methyl 6-methyl-3-(2-(quinuclidin-3-ylamino)ethyl)-1H-indazole-4-carboxylate from Step C above to lithium (S)-6-methyl-3-(2-(quinuclidin-3-ylamino)ethyl)-1H-indazole-4-carboxylate: MS (ESI+) m/z 328 (M+H).

Step E: The procedure described in Step F of Example 8 was used to convert lithium (S)-6-methyl-3-(2-(quinuclidin-3-ylamino)ethyl)-1H-indazole-4-carboxylate from Step D above to (S)-methyl 6-methyl-3-(2-(quinuclidin-3-ylamino)ethyl)-1H-indazole-4-carboxylate (43 mg, 17%) as an off-white solid, which was treated immediately with hydrochloric acid following the procedure described in Step G of Example 8 to afford (S)-methyl 6-methyl-3-(2-(quinuclidin-3-ylamino)ethyl)-1H-indazole-4-carboxylate hydrochloride as an off-white solid: $^1$H NMR (500 MHz, CD$_3$OD) δ 8.06 (s, 1H), 8.04 (s, 1H), 7.82 (s, 1H), 4.73-4.65 (m, 1H), 4.14-3.99 (m, 2H), 3.83-3.71 (m, 2H), 3.45-3.41 (m, 3H), 2.54 (d, J=2.5 Hz, 1H), 2.51 (s, 3H), 2.28 (br s, 1H), 2.17-2.10 (m, 2H), 2.10-1.99 (m, 1H); MS (ESI) m/z 311 (M+H).

Example 12

Preparation of (S)-4-hydroxy-7-(quinuclidin-3-yl)-8,9-dihydro-[1,4]diazepino[6,7,1-hi]indazol-6(7H)-one hydrochloride

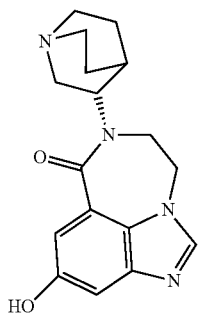

Step A: To a solution of (S)-4-methoxy-7-(quinuclidin-3-yl)-8,9-dihydro-[1,4]diazepino[6,7,1-hi]indazol-6(7H)-one (200 mg, 0.6 mmol) from Step K of Example 10 in acetic acid (5 mL) was added 48% aqueous hydrogen bromide (5 ml) and the mixture was heated to 100° C. for 3 days. After cooling to room temperature and diluting with methanol, the pH was adjusted to 8. The solvent was concentrated in vacuo and the residue was purified by prep HPLC. The product was then treated immediately with hydrochloric acid following the procedure described in Step G of Example 8 to afford (S)-4-hydroxy-7-(quinuclidin-3-yl)-8,9-dihydro-[1,4]diazepino[6,7,1-hi]indazol-6(7H)-one hydrochloride (43 mg, 21%) as an off-white solid: $^1$H NMR (500 MHz, CD$_3$OD) δ 7.98 (s, 1H), 7.76 (dd, J=2.5 Hz, 1H), 7.32 (d, J=2.0 Hz, 1H), 4.71-4.60 (m, 3H), 4.12-3.98 (m, 2H), 3.83-3.68 (m, 3H), 3.41-3.34 (m, 3H), 2.54 (d, J=2.5 Hz, 1H), 2.29 (brs 1H), 2.27-2.10 (m, 2H), 2.10-1.99 (m, 1H); MS (ESI+) m/z 313 (M+H).

Example 13

Preparation of 6-((S)-quinuclidin-3-yl)-5,6-dihydroimidazo[4,5,1-jk][1,4]benzodiazepin-7(4H)-one, hydrochloride salt

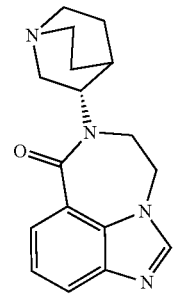 [SMILES: O=C1c2cccc3ncn(c23)CCN1[C@@H]1CN2CCC1CC2]

Step A: To a stirred solution of 2-chloro-3-nitrobenzoate (1.0 g, 5.0 mmol) in anhydrous methanol (10 mL) at 0° C. was added thionyl chloride (0.5 mL, 7.4 mmol) dropwise and the reaction mixture was stirred overnight at reflux. The mixture was diluted with methanol and concentrated under reduced pressure to remove the excess thionyl chloride and then re-dissolved in ethyl acetate, washed with saturated aqueous sodium bicarbonate, re-extracted with ethyl acetate, dried (Na$_2$SO$_4$), filtered, and concentrated under reduced pressure to give methyl 2-chloro-3-nitrobenzoate (1.1 g, 98%) as a white foam that was used in the next step without further purification: $^1$H NMR (300 MHz, DMSO-d$_6$) δ 8.21 (d, J=1.5 Hz, 1H), 8.07 (dd, J=7.8, 1.5 Hz, 1H), 7.73 (t, J=8.1 Hz, 1H), 3.91 (s, 3H).

Step B: To a stirred solution of methyl 2-chloro-3-nitrobenzoate (1.1 g, 4.9 mmol) from Step A above in THF (33 mL) was added triethylamine (0.8 mL, 6.0 mmol) followed by 2,2-dimethoxyethanamine (0.7 mL, 6.0 mmol) at room temperature. The reaction mixture was stirred overnight at reflux. The suspension was concentrated under reduced pressure and purified by column chromatography (silica gel, 0% to 10% ethyl acetate in hexanes) to afford methyl 2-(2,2-dimethoxyethylamino)-3-nitrobenzoate (1.4 g, 98%): $^1$H NMR (500 MHz, DMSO-d$_6$) δ 8.39 (t, J=4.5 Hz, 8.08-8.05 (m, 2H), 6.83 (t, J=8.0 Hz, 1H), 4.54 (t, J=5.0 Hz, 1H), 3.87 (s, 3H), 3.31 (s, 6H), 2.93 (t, J=5.0 Hz, 1H).

Step C: To an argon purged solution of methyl 2-(2,2-dimethoxyethylamino)-3-nitrobenzoate (1.4 g, 4.7 mmol) from Step B above in ethanol (50 mL) at room temperature was added 10% palladium on carbon. The reaction was stirred overnight under an atmosphere of hydrogen (balloon pressure). The reaction mixture was filtered through celite and concentrated under reduced pressure to give methyl 3-amino-2-(2,2-dimethoxyethylamino)benzoate (1.2 g, quantitative yield) as a dark red oil: $^1$H NMR (300 MHz, DMSO-d$_6$) δ 7.06 (d, J=5.0 Hz, 1H), 6.85 (dd, J=7.8, 1.2 Hz, 1H), 6.74 (t, J=7.8 Hz, 1H), 6.06 (t, J=7.5 Hz, 1H), 4.84 (s, 2H), 4.38 (t, J=5.4 Hz, 1H), 3.80 (s, 3H), 3.23 (s, 6H), 3.04 (dd, J=7.2, 5.7 Hz, 2H); MS (ESI+) m/z 254 (M+H).

Step D: To a stirred solution of methyl 3-amino-2-(2,2-dimethoxyethylamino)benzoate (0.4 g, 1.6 mmol) from Step C above in DMF (15 mL) was added trimethyl orthoformate (0.5 mL, 4.7 mmol) and the reaction was heated to reflux and stirred overnight. The reaction mixture was washed with water, extracted with methylene chloride, dried (Na₂SO₄), filtered, and concentrated under reduced pressure to give the crude material which was purified by column chromatography (silica gel, 0% to 100% ethyl acetate in hexanes) to afford methyl 1-(2,2-dimethoxyethyl)-1H-benzo[d]imidazole-7-carboxylate: ¹H NMR (500 MHz, DMSO-d₆) δ 8.25 (s, 1H), 7.90 (dd, J=8.0, 1.0 Hz, 1H), 7.69 (dd, J=8.0, 1.0 Hz, 1H), 7.29 (t, J=8.0 Hz, 1H), 4.64 (d, J=5.0 Hz, 2H), 4.48 (t, J=5.0 Hz, 1H), 3.91 (s, 3H), 3.22 (s, 6H); MS (ESI+) m/z 264 (M+H).

Step E: To a stirred solution of methyl 1-(2,2-dimethoxyethyl)-2-isopropyl-1H-benzo[d]imidazole-7-carboxylate from Step D above in methylene chloride were added water and trifluoroacetic acid and the reaction was stirred at room temperature for 2 h and then heated at reflux for 3.5 h. The reaction mixture was concentrated under reduced pressure to remove the excess trifluoroacetic acid, diluted with methylene chloride, washed with saturated aqueous sodium bicarbonate, re-extracted with methylene chloride, dried (Na₂SO₄), filtered, and concentrated under reduced pressure to give methyl 1-(2-oxoethyl)-1H-benzo[d]imidazole-7-carboxylate (0.2 g, 44% over two steps): ¹H NMR (500 MHz, DMSO-d₆) δ 9.69 (s, 1H), 7.97 (dd, J=8.0, 1.0 Hz, 1H), 7.81 (dd, J=7.5, 1.0 Hz, 1H), 7.33 (t, J=8.0 Hz, 1H), 5.48 (s, 2H), 3.84 (s, 3H); MS (ESI+) m/z 218 (M+H).

Step F: To a stirred solution of (S)-(−)-3-aminoquinuclidine dihydrochloride (0.2 g, 0.8 mmol) in methylene chloride (2 mL) was added sodium hydride (0.1 g, 1.6 mmol) and the mixture was stirred for 2 h. A solution of methyl 1-(2-oxoethyl)-1H-benzo[d]imidazole-7-carboxylate (0.2 g, 0.7 mmol) from Step E above in methylene chloride (3 mL) was added followed by acetic acid (0.7 mL) and the mixture was stirred at room temperature for 4 h. Sodium triacetoxyborohydride (0.4 g, 2.1 mmol) was then added in portions and the reaction was stirred at room temperature overnight. The crude reaction was quenched with methanol, concentrated under reduced pressure, and purified by preparative thin layer chromatography (90:9:1 methylene chloride/methanol/ammonium hydroxide) to afford (S)-methyl 1-(2-(quinuclidin-3-ylamino)ethyl)-1H-benzo[d]imidazole-7-carboxylate (0.2 g, quantitative yield): MS (ESI+) m/z 329 (M+H).

Step G: A mixture of (S)-methyl 1-(2-(quinuclidin-3-ylamino)ethyl)-1H-benzo[d]imidazole-7-carboxylate (0.2 g, 0.7 mmol) from Step F above, lithium hydroxide monohydrate (0.1 g, 2.1 mmol), water (5 mL), and tetrahydrofuran (5 mL) was heated at reflux for 5 h. The reaction solution was cooled to room temperature and concentrated under reduced pressure to give lithium (S)-1-(2-(quinuclidin-3-ylamino)ethyl)-1H-benzo[d]imidazole-7-carboxylate (0.2 g): MS (ESI+) m/z 315 (M+H).

Step H: A mixture of lithium (S)-1-(2-(quinuclidin-3-ylamino)ethyl)-1H-benzo[d]imidazole-7-carboxylate (0.2 g, 0.7 mmol) from Step G above, N,N-diisopropylethylamine (0.7 mL, 4.1 mmol), and 1-propanephosphonic acid cyclic anhydride (T3P) (2.1 mL, 3.4 mmol) in N,N-dimethylformamide (10 mL) was stirred at room temperature for 7 h. The crude reaction was concentrated under reduced pressure and then purified by SCX column and preparative thin layer chromatography (90:9:1 methylene chloride/methanol/ammonium hydroxide) to afford 6-((S)-quinuclidin-3-yl)-5,6-dihydroimidazo[4,5,1-jk][1,4]benzodiazepin-7(4H)-one: ¹H NMR (500 MHz, DMSO-d₆) δ 8.32 (s, 1H), 7.91 (d, J=8.0 Hz, 1H), 7.86 (dd, J=8.0, 1.0 Hz, 1H), 7.32 (t, J=8.0 Hz, 1H), 4.85-4.50 (m, 2H), 4.48-4.39 (m, 2H), 3.91-3.33 (m, 1H), 3.31-3.11 (m, 1H), 3.08-3.02 (m, 1H), 2.99-2.89 (m, 1H), 2.81-2.71 (m, 3H), 1.97-1.95 (m, 1H), 1.71-1.56 (m, 3H), 1.49-1.39 (m, 1H).

Step I: 6-((S)-quinuclidin-3-yl)-5,6-dihydroimidazo[4,5,1-jk][1,4]benzodiazepin-7(4H)-one from Step H above was dissolved in methanol (5 mL) and treated with hydrochloric acid (1.25 M solution in methanol, 0.1 mL, 0.08 mmol). The mixture was stirred for 0.5 h and concentrated under reduced pressure. The residue was lyophilized from acetonitrile/water (1:5, 6 mL) to afford the corresponding hydrochloride salt as a white solid: ¹H NMR (500 MHz, DMSO-d₆) δ 10.20 (br s, 1H), 8.61 (s, 1H), 7.99 (d, J=7.5 Hz, 1H), 7.94 (d, J=8.0 Hz, 1H), 7.42 (t, J=8.0 Hz, 1H), 4.77-4.55 (m, 2H), 4.49-4.15 (m, 2H), 4.14-3.75 (m, 1H), 3.74-3.61 (m, 1H), 3.60-3.39 (m, 2H), 3.38-3.21 (m, 3H), 2.36-2.34 (m, 1H), 1.97-1.81 (m, 4H); MS (ESI+) m/z 297 (M+H).

Example 14

Preparation of 2-methyl-6-((R)-quinuclidin-3-yl)-5,6-dihydroimidazo[4,5,1-jk][1,4]benzodiazepin-7(4H)-one, hydrochloride salt

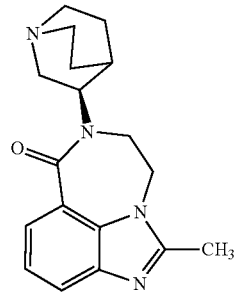 [SMILES: Cc1nc2cccc3c2n1CCN([C@H]1CN2CCC1CC2)C3=O]

Step A: To a stirred solution of methyl 3-amino-2-(2,2-dimethoxyethylamino)benzoate (1.0 g, 3.9 mmol) from Step C of Example 13 in DMF (30 mL) was added trimethyl orthoacetate (1.5 mL, 11.8 mmol) and the reaction was refluxed overnight. The reaction mixture was washed with saturated aqueous sodium bicarbonate, extracted with methylene chloride, dried (Na₂SO₄), filtered, and concentrated under reduced pressure to give the crude material which was purified by column chromatography (silica gel, 0% to 90% ethyl acetate in hexanes) to afford methyl 1-(2,2-dimethoxyethyl)-2-methyl-1H-benzo[d]imidazole-7-carboxylate (0.8 g, 72%): ¹H NMR (300 MHz, DMSO-d₆) δ 7.74 (dd, J=8.1, 1.2 Hz, 1H), 7.55 (dd, J=7.8, 1.2 Hz, 1H), 7.21 (t, J=7.5 Hz, 1H), 4.56 (d, J=4.8 Hz, 2H), 4.44 (t, J=4.8 Hz, 1H), 3.90 (s, 3H), 3.21 (s, 6H), 2.58 (s, 3H); MS (ESI+) m/z 279 (M+H).

Step B: To a stirred solution of methyl 1-(2,2-dimethoxyethyl)-2-isopropyl-1H-benzo[d]imidazole-7-carboxylate from Step A above in methylene chloride were added water and trifluoroacetic acid and the reaction was stirred at room temperature for 2 h and then heated at reflux for 3.5 h. The reaction mixture was concentrated under reduced pressure to remove the excess trifluoroacetic acid, diluted with methylene chloride, washed with saturated aqueous sodium bicarbonate, re-extracted with methylene chloride, dried (Na₂SO₄), filtered, and concentrated under reduced pressure to give methyl 2-methyl-1-(2-oxoethyl)-1H-benzo[d]imidazole-7-carboxylate (0.4 g, 56%): ¹H NMR (500 MHz, DMSO-d₆) δ 9.70 (s, 1H), 7.81 (dd, J=8.0, 1.5 Hz, 1H), 7.67

(dd, J=7.5, 1.0 Hz, 1H), 7.25 (t, J=8.0 Hz, 1H), 5.38 (s, 2H), 3.84 (s, 3H), 2.47 (s, 3H); MS (ESI+) m/z 233 (M+H).

Step C: The procedure described in Step F of Example 13 was used to convert methyl 2-methyl-1-(2-oxoethyl)-1H-benzo[d]imidazole-7-carboxylate from Step B above and (R)-(+)-3-aminoquinuclidine dihydrochloride to (R)-methyl 2-methyl-1-(2-(quinuclidin-3-ylamino)ethyl)-1H-benzo[d]imidazole-7-carboxylate, except that 1,4-dioxane was used as the solvent: MS (ESI+) m/z 343 (M+H).

Step D: The procedure described in Step G of Example 13 was used to convert (R)-methyl 2-methyl-1-(2-(quinuclidin-3-ylamino)ethyl)-1H-benzo[d]imidazole-7-carboxylate from Step C above to lithium (R)-2-methyl-1-(2-(quinuclidin-3-ylamino)ethyl)-1H-benzo[d]imidazole-7-carboxylate: MS (ESI+) m/z 329 (M+H).

Step E: The procedure described in Step H of Example 13 was used to convert lithium (R)-2-methyl-1-(2-(quinuclidin-3-ylamino)ethyl)-1H-benzo[d]imidazole-7-carboxylate from Step D above to 2-methyl-6-((R)-quinuclidin-3-yl)-5,6-dihydroimidazo[4,5,1-jk][1,4]benzodiazepin-7(4H)-one: $^1$H NMR (500 MHz, DMSO-$d_6$) δ 7.81 (d, J=7.5 Hz, 1H), 7.72 (d, J=7.5 Hz, 1H), 7.24 (t, J=7.0 Hz, 1H), 4.85-4.39 (m, 2H), 4.38-3.98 (m, 2H), 3.97-3.41 (m, 1H), 3.32-3.29 (m, 1H), 3.17-3.12 (m, 1H), 3.04-2.99 (m, 1H), 2.89-2.87 (m, 1H), 2.80-2.73 (m, 3H), 2.53-2.47 (m, 2H), 1.96-1.95 (m, 1H), 1.70-1.58 (m, 3H), 1.46-1.44 (m, 1H); MS (ESI+) m/z 311 (M+H).

Step F: The procedure described in Step I of Example 13 was used to convert 2-methyl-6-((R)-quinuclidin-3-yl)-5,6-dihydroimidazo[4,5,1-jk][1,4]benzodiazepin-7(4H)-one from Step E above to the corresponding hydrochloride salt (off-white solid): $^1$H NMR (500 MHz, DMSO-$d_6$) δ 10.66 (br s, 1H), 7.89 (d, J=8.0 Hz, 1H), 7.80 (d, J=9.0 Hz, 1H), 7.34 (t, J=8.0 Hz, 1H), 4.75-4.74 (m, 1H), 4.85-4.84 (m, 1H), 4.24-4.21 (m, 2H), 3.90-3.87 (m, 1H), 3.67-3.65 (m, 1H), 3.56-3.52 (m, 2H), 3.27-3.21 (m, 3H), 2.58 (s, 3H), 2.36-2.31 (m, 1H), 1.97-1.84 (m, 4H); MS (ESI+) m/z 311 (M+H).

Example 15

Preparation of 2-methyl-6-((S)-quinuclidin-3-yl)-5,6-dihydroimidazo[4,5,1-jk][1,4]benzodiazepin-7(4H)-one, hydrochloride salt

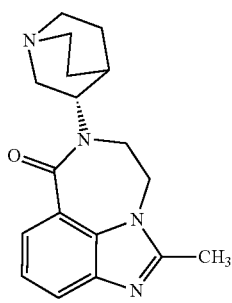 [SMILES: Cc1nc2cccc3c2n1CCN([C@@H]1CN2CCC1CC2)C3=O]

Step A: The procedure described in Step F of Example 13 was used to convert methyl 2-methyl-1-(2-oxoethyl)-1H-benzo[d]imidazole-7-carboxylate from Step B of Example 9 and (S)-(−)-3-aminoquinuclidine dihydrochloride to (S)-methyl 2-methyl-1-(2-(quinuclidin-3-ylamino)ethyl)-1H-benzo[d]imidazole-7-carboxylate, except that 1,4-dioxane was used as the solvent: MS (ESI+) m/z 343 (M+H).

Step B: The procedure described in Step G of Example 13 was used to convert (S)-methyl 2-methyl-1-(2-(quinuclidin-3-ylamino)ethyl)-1H-benzo[d]imidazole-7-carboxylate from Step A above to lithium (S)-2-methyl-1-(2-(quinuclidin-3-ylamino)ethyl)-1H-benzo[d]imidazole-7-carboxylate: MS (ESI+) m/z 329 (M+H).

Step C: The procedure described in Step H of Example 13 was used to convert lithium (S)-2-methyl-1-(2-(quinuclidin-3-ylamino)ethyl)-1H-benzo[d]imidazole-7-carboxylate from Step B above to 2-methyl-6-((S)-quinuclidin-3-yl)-5,6-dihydroimidazo[4,5,1-jk][1,4]benzodiazepin-7(4H)-one: $^1$H NMR (500 MHz, DMSO-$d_6$) δ 7.81 (d, J=7.5 Hz, 1H), 7.72 (d, J=7.5 Hz, 1H), 7.24 (t, J=7.0 Hz, 1H), 4.85-4.39 (m, 2H), 4.38-3.98 (m, 2H), 3.97-3.41 (m, 1H), 3.32-3.29 (m, 1H), 3.17-3.12 (m, 1H), 3.04-2.99 (m, 1H), 2.89-2.87 (m, 1H), 2.80-2.73 (m, 3H), 2.53-2.47 (m, 2H), 1.96-1.95 (m, 1H), 1.70-1.58 (m, 3H), 1.46-1.44 (m, 1H); MS (ESI+) m/z 311 (M+H).

Step D: The procedure described in Step I of Example 13 was used to convert 2-methyl-6-((S)-quinuclidin-3-yl)-5,6-dihydroimidazo[4,5,1-jk][1,4]benzodiazepin-7(4H)-one from Step C above to the corresponding hydrochloride salt (off-white solid): $^1$H NMR (500 MHz, DMSO-$d_6$) δ 10.66 (br s, 1H), 7.89 (d, J=8.0 Hz, 1H), 7.80 (d, J=9.0 Hz, 1H), 7.34 (t, J=8.0 Hz, 1H), 4.75-4.74 (m, 1H), 4.85-4.84 (m, 1H), 4.24-4.21 (m, 2H), 3.90-3.87 (m, 1H), 3.67-3.65 (m, 1H), 3.56-3.52 (m, 2H), 3.27-3.21 (m, 3H), 2.58 (s, 3H), 2.36-2.31 (m, 1H), 1.97-1.84 (m, 4H); MS (ESI+) m/z 311 (M+H).

Example 16

Preparation of 2-ethyl-6-((R)-quinuclidin-3-yl)-5,6-dihydroimidazo[4,5,1-jk][1,4]benzodiazepin-7(4H)-one, hydrochloride salt

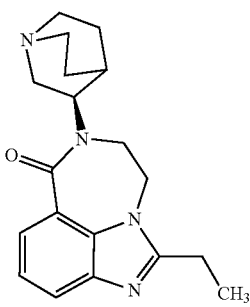 [SMILES: CCc1nc2cccc3c2n1CCN([C@H]1CN2CCC1CC2)C3=O]

Step A: The procedure described in Step A of Example 20 was used to convert methyl 3-amino-2-(2,2-dimethoxyethylamino)benzoate from Step C of Example 13 to methyl 1-(2,2-dimethoxyethyl)-2-ethyl-1H-benzo[d]imidazole-7-carboxylate, except that 1,1,1-trimethoxypropane was used instead of (trimethoxymethyl)benzene, providing the product as a brown oil: $^1$H NMR (500 MHz, CDCl$_3$) δ 7.91 (d, J=8.0 Hz, 1H), 7.72 (d, J=7.5 Hz, 1H), 7.26 (t, J=8.0 Hz, 1H), 4.65 (d, J=5.0 Hz, 2H), 4.45 (t, J=5.0 Hz, 1H), 3.97 (s, 3H), 3.29 (s, 6H), 3.01 (q, J=7.5 Hz, 2H), 1.49 (t, J=7.5 Hz, 3H); MS (ESI+) m/z 293 (M+H).

Step B: The procedure described in Step E of Example 13 was used to convert methyl 1-(2,2-dimethoxyethyl)-2-ethyl-1H-benzo[d]imidazole-7-carboxylate from Step A above to methyl 2-ethyl-1-(2-oxoethyl)-1H-benzo[d]imidazole-7-carboxylate, providing the product as a light pink solid: $^1$H NMR (500 MHz, CDCl$_3$) δ 9.79 (s, 1H), 7.97 (d, J=8.0 Hz, 1H), 7.89 (d, J=7.5 Hz, 1H), 7.29 (t, J=8.0 Hz, 1H), 5.28 (s, 2H), 3.90 (s, 3H), 2.85 (q, J=7.5 Hz, 2H), 1.46 (t, J=7.5 Hz, 3H); MS (ESI+) m/z 247 (M+H).

Step C: The procedure described in Step F of Example 13 was used to convert methyl 2-ethyl-1-(2-oxoethyl)-1H-benzo[d]imidazole-7-carboxylate from Step B above and (R)-(+)-3-aminoquinuclidine dihydrochloride to (R)-methyl 2-ethyl-(2-(quinuclidin-3-ylamino)ethyl)-1H-benzo[d]imidazole-7-carboxylate, providing the product as a white paste: $^1$H NMR (500 MHz, CDCl$_3$) δ 7.91 (d, J=8.0 Hz, 1H), 7.77 (d, J=7.5 Hz, 1H), 7.25 (t, J=8.0 Hz, 1H), 4.62-4.59 (m, 2H), 3.96 (s, 3H), 3.08-3.04 (m, 1H), 3.01 (q, J=7.5 Hz, 2H), 2.88-2.83 (m, 1H), 2.80-2.68 (m, 5H), 2.67-2.61 (m, 1H), 2.29-2.26 (m, 1H), 1.67-1.60 (m, 4H), 1.51 (t, J=7.5 Hz, 3H), 1.42-1.37 (m, 1H), 1.26-1.23 (m, 1H); MS (ESI+) m/z 357 (M+H).

Step D: The procedure described in Step G of Example 13 was used to convert (R)-methyl 2-ethyl-1-(2-(quinuclidin-3-ylamino)ethyl)-1H-benzo[d]imidazole-7-carboxylate from Step C above to lithium (R)-2-ethyl-1-(2-(quinuclidin-3-ylamino)ethyl)-1H-benzo[d]imidazole-7-carboxylate, providing the product as a white solid: $^1$H NMR (500 MHz, MeOD) δ 7.54 (d, J=8.0 Hz, 1H), 7.37 (d, J=7.5 Hz, 1H), 7.17 (t, J=8.0 Hz, 1H), 4.61 (t, J=7.0 Hz, 2H), 3.04-3.00 (m, 3H), 2.98-2.56 (m, 7H), 2.27-2.24 (m, 1H), 1.82-1.51 (m, 4H), 1.50-1.38 (m, 4H), 1.34-1.20 (m, 1H); MS (ESI+) m/z 343 (M+H).

Step E: The procedure described in Step H of Example 13 was used to convert lithium (R)-2-ethyl-1-(2-(quinuclidin-3-ylamino)ethyl)-1H-benzo[d]imidazole-7-carboxylate from Step D above to 2-ethyl-6-((R)-quinuclidin-3-yl)-5,6-dihydroimidazo[4,5,1-jk][1,4]benzodiazepin-7(4H)-one, providing the product as a white solid: $^1$H NMR (500 MHz, MeOD) δ 8.30 (br s, 1H), 8.02 (d, J=8.0 Hz, 1H), 7.76 (t, J=8.0 Hz, 1H), 4.80-3.50 (m, 8H), 3.49-3.37 (m, 3H), 3.36-3.32 (m, 2H), 2.55-2.14 (m, 4H), 2.03-1.96 (m, 1H), 1.57 (t, J=7.5 Hz, 3H); MS (ESI+) m/z 325 (M+H).

Step F: The procedure described in Step I of Example 13 was used to convert 2-ethyl-6-((R)-quinuclidin-3-yl)-5,6-dihydroimidazo[4,5,1-jk][1,4]benzodiazepin-7(4H)-one to the corresponding hydrochloride salt (white solid): $^1$H NMR (500 MHz, MeOD) δ 8.30 (br s, 1H), 8.02 (d, J=8.0 Hz, 1H), 7.75 (t, J=8.0 Hz, 1H), 4.79-3.54 (m, 8H), 3.52-3.33 (m, 3H), 3.33-3.17 (m, 2H), 2.55-1.94 (m, 5H), 1.57 (t, J=7.5 Hz, 3H); MS (ESI+) m/z 325 (M+H).

Example 17

Preparation of 2-ethyl-6-((S)-quinuclidin-3-yl)-5,6-dihydroimidazo[4,5,1-jk][1,4]benzodiazepin-7(4H)-one, hydrochloride salt

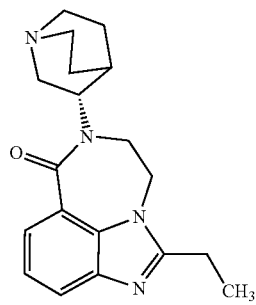 [SMILES: CCc1nc2cccc3c2n1CCN([C@@H]1CN2CCC1CC2)C3=O]

Step A: The procedure described in Step A of Example 20 was used to convert methyl 3-amino-2-(2,2-dimethoxyethylamino)benzoate from Step C of Example 13 to methyl 1-(2,2-dimethoxyethyl)-2-ethyl-1H-benzo[d]imidazole-7-carboxylate, except that 1,1,1-trimethoxypropane was used instead of (trimethoxymethyl)benzene, providing the product as a brown oil: $^1$H NMR (500 MHz, CDCl$_3$) δ 7.91 (d, J=8.0 Hz, 1H), 7.72 (d, J=7.5 Hz, 1H), 7.26 (t, J=8.0 Hz, 1H), 4.65 (d, J=5.0 Hz, 2H), 4.45 (t, J=5.0 Hz, 1H), 3.97 (s, 3H), 3.29 (s, 6H), 3.01 (q, J=7.5 Hz, 2H), 1.49 (t, J=7.5 Hz, 3H); MS (ESI+) m/z 293 (M+H).

Step B: The procedure described in Step E of Example 13 was used to convert methyl 1-(2,2-dimethoxyethyl)-2-ethyl-1H-benzo[d]imidazole-7-carboxylate from Step A above to methyl 2-ethyl-1-(2-oxoethyl)-1H-benzo[d]imidazole-7-carboxylate, providing the product as a light pink solid: $^1$H NMR (500 MHz, CDCl$_3$) δ 9.79 (s, 1H), 7.97 (d, J=8.0 Hz, 1H), 7.89 (d, J=7.5 Hz, 1H), 7.29 (t, J=8.0 Hz, 1H), 5.28 (s, 2H), 3.90 (s, 3H), 2.85 (q, J=7.5 Hz, 2H), 1.46 (t, J=7.5 Hz, 3H); MS (ESI+) m/z 247 (M+H).

Step C: The procedure described in Step F of Example 13 was used to convert methyl 2-ethyl-1-(2-oxoethyl)-1H-benzo[d]imidazole-7-carboxylate from Step B above and (S)-(−)-3-aminoquinuclidine dihydrochloride to (S)-methyl 2-ethyl-1-(2-(quinuclidin-3-ylamino)ethyl)-1H-benzo[d]imidazole-7-carboxylate, providing the product as a white paste: $^1$H NMR (500 MHz, CDCl$_3$) δ 7.92 (d, J=8.0 Hz, 1H), 7.78 (d, J=8.0 Hz, 1H), 7.25 (t, J=7.5 Hz, 1H), 4.62 (t, J=6.5 Hz, 2H), 3.96 (s, 3H), 3.18-3.14 (m, 1H), 3.00 (q, J=7.5 Hz, 2H), 2.88-2.72 (m, 8H), 2.42-2.39 (d, 1H), 1.75-1.67 (m, 3H), 1.51 (q, J=7.5 Hz, 3H), 1.46-1.26 (m, 2H); MS (ESI+) m/z 357 (M+H).

Step D: The procedure described in Step G of Example 13 was used to convert (S)-methyl 2-ethyl-1-(2-(quinuclidin-3-ylamino)ethyl)-1H-benzo[d]imidazole-7-carboxylate from Step C above to lithium (S)-2-ethyl-1-(2-(quinuclidin-3-ylamino)ethyl)-1H-benzo[d]imidazole-7-carboxylate, providing the product as a light green paste: $^1$H NMR (500 MHz, MeOD) δ 7.55 (d, J=8.0 Hz, 1H), 7.37 (d, J=7.5 Hz, 1H), 7.17 (d, J=8.0 Hz, 1H), 4.61 (t, J=5.5 Hz, 2H), 3.01-2.98 (m, 3H), 2.95-2.86 (m, 1H), 2.87-2.57 (m, 6H), 2.28-2.24 (m, 1H), 1.76-1.57 (m, 3H), 1.52-1.38 (m, 4H), 1.34-1.20 (m, 2H); MS (ESI+) m/z 343 (M+H).

Step E: The procedure described in Step H of Example 13 was used to convert lithium (S)-2-ethyl-1-(2-(quinuclidin-3-ylamino)ethyl)-1H-benzo[d]imidazole-7-carboxylate from Step D above to 2-ethyl-6-((S)-quinuclidin-3-yl)-5,6-dihydroimidazo[4,5,1-jk][1,4]benzodiazepin-7(4H)-one, providing the product as a colorless oil: $^1$H NMR (500 MHz, MeOD) δ 8.31 (br s, 1H), 8.02 (d, J=8.0 Hz, 1H), 7.76 (t, J=8.0 Hz, 1H), 4.51-3.64 (m, 7H), 3.44-3.39 (m, 3H), 2.55-2.11 (m, 4H), 1.75-1.54 (m, 5H), 1.05 (t, J=7.0 Hz, 2H); MS (ESI+) m/z 325 (M+H).

Step F: The procedure described in Step I of Example 13 was used to convert 2-ethyl-6-((S)-quinuclidin-3-yl)-5,6-dihydroimidazo[4,5,1-jk][1,4]benzodiazepin-7(4H)-one from Step E above to the corresponding hydrochloride salt (white solid): $^1$H NMR (500 MHz, MeOD) δ 8.30 (br s, 1H), 8.01 (d, J=8.5 Hz, 1H), 7.75, (t, J=8.0 Hz, 1H), 4.66-4.23 (m, 3H), 4.20-3.52 (m, 5H), 3.50-3.35 (m, 4H), 2.90-2.29 (m, 2H), 2.28-2.70 (m, 4H), 1.57 (t, J=7.5 Hz, 3H); MS (ESI+) m/z 325 (M+H).

Example 18

Preparation of 2-isopropyl-6-((R)-quinuclidin-3-yl)-5,6-dihydroimidazo[4,5,1-jk][1,4]benzodiazepin-7(4H)-one, hydrochloride salt

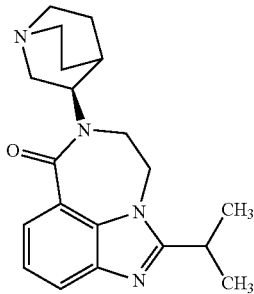 [SMILES: CC(C)c1nc2cccc3c2n1CCN([C@H]1CN2CCC1CC2)C3=O]

Step A: To a stirred solution of methyl 3-amino-2-(2,2-dimethoxyethylamino)benzoate (0.5 g, 2.0 mmol) from Step C of Example 13 in DMF (15 mL) and H₂O (0.5 mL) were added oxone (0.8 g, 1.3 mmol) and iso-butyraldehyde (0.2 mL, 2.2 mmol) and the reaction was stirred overnight at room temperature. The reaction mixture was washed with saturated aqueous sodium bicarbonate, re-extracted with methylene chloride, dried (Na₂SO₄), filtered, and concentrated under reduced pressure. The crude material was purified by column chromatography (silica gel, 0% to 30% ethyl acetate in hexanes) to afford methyl 1-(2,2-dimethoxyethyl)-2-isopropyl-1H-benzo[d]imidazole-7-carboxylate (0.5 g, 85%): ¹H NMR (500 MHz, DMSO-d₆) δ 7.79 (dd, J=8.0, 1.0 Hz, 1H), 7.56 (dd, J=7.5, 1.0 Hz, 1H), 7.22 (t, J=8.0 Hz, 1H), 4.61 (d, J=5.0 Hz, 2H), 4.38 (t, J=5.0 Hz, 1H), 3.90 (s, 3H), 3.38-3.33 (m, 1H), 3.19 (s, 6H), 1.32 (d, J=7.0 Hz, 6H); MS (ESI+) m/z 306 (M+H).

Step B: To a stirred solution of methyl 1-(2,2-dimethoxyethyl)-2-isopropyl-1H-benzo[d]imidazole-7-carboxylate from Step A above in methylene chloride and water was added trifluoroacetic acid and the reaction was stirred at room temperature for 1.5 h and then heated at reflux for 2 h. The reaction mixture was concentrated under reduced pressure to remove the excess trifluoroacetic acid, diluted with methylene chloride, washed with saturated aqueous sodium bicarbonate, re-extracted with methylene chloride, dried (Na₂SO₄), filtered, and concentrated under reduced pressure to give methyl 2-isopropyl-1-(2-oxoethyl)-1H-benzo[d]imidazole-7-carboxylate: ¹H NMR (300 MHz, DMSO-d₆) δ 9.69 (s, 1H), 7.87 (dd, J=8.1, 0.9 Hz, 7.68 (dd, J=7.5, 0.9 Hz, 1H), 7.26 (t, J=7.8 Hz, 1H), 5.44 (s, 2H), 3.84 (s, 3H), 3.22-3.17 (m, 1H), 1.34-1.27 (m, 6H); MS (ESI+) m/z 261 (M+H).

Step C: The procedure described in Step F of Example 13 was used to convert methyl 2-isopropyl-1-(2-oxoethyl)-1H-benzo[d]imidazole-7-carboxylate from Step B above and (R)-(+)-3-aminoquinuclidine dihydrochloride to (R)-methyl 2-isopropyl-1-(2-(quinuclidin-3-ylamino)ethyl)-1H-benzo[d]imidazole-7-carboxylate, except that 1,4-dioxane was used as the solvent: MS (ESI+) m/z 371 (M+H).

Step D: The procedure described in Step G of Example 13 was used to convert (R)-methyl 2-isopropyl-1-(2-(quinuclidin-3-ylamino)ethyl)-1H-benzo[d]imidazole-7-carboxylate from Step C above to lithium (R)-2-isopropyl-1-(2-(quinuclidin-3-ylamino)ethyl)-1H-benzo[d]imidazole-7-carboxylate: MS (ESI+) m/z 357 (M+H).

Step E: The procedure described in Step H of Example 13 was used to convert lithium (R)-2-isopropyl-1-(2-(quinuclidin-3-ylamino)ethyl)-1H-benzo[d]imidazole-7-carboxylate from Step D above to 2-isopropyl-6-((R)-quinuclidin-3-yl)-5,6-dihydroimidazo[4,5,1-jk][1,4]benzodiazepin-7(4H)-one: ¹H NMR (500 MHz, DMSO-d₆) δ 7.82 (d, J=7.5 Hz, 1H), 7.76 (dd, J=8.0, 1.0 Hz, 1H), 7.25 (t, J=8.0 Hz, 1H), 4.89-4.49 (m, 2H), 4.48-4.01 (m, 1H), 3.98-3.41 (m, 1H), 3.24-3.12 (m, 3H), 3.04-2.73 (m, 5H), 1.96-1.95 (m, 1H), 1.75-1.58 (m, 3H), 1.44-1.31 (m, 7H); MS (ESI+) m/z 339 (M+H).

Step F: The procedure described in Step I of Example 13 was used to convert 2-isopropyl-6-((R)-quinuclidin-3-yl)-5,6-dihydroimidazo[4,5,1-jk][1,4]benzodiazepin-7(4H)-one from Step E above to the corresponding hydrochloride salt (white solid): ¹H NMR (500 MHz, DMSO-d₆) δ 10.29 (br s, 1H), 7.84 (d, J=8.0 Hz, 1H), 7.80 (dd, J=8.0, 1.0 Hz, 1H), 7.27 (t, J=8.0 Hz, 1H), 4.73-4.44 (m, 2H), 4.43-4.01 (m, 1H), 3.98-3.69 (m, 1H), 3.68-3.16 (m, 8H), 2.28-2.27 (m, 1H), 1.92-1.77 (m, 4H), 1.37-1.33 (m, 6H); MS (ESI+) m/z 339 (M+H).

Example 19

Preparation of 2-isopropyl-6-((S)-quinuclidin-3-yl)-5,6-dihydroimidazo[4,5,1-jk][1,4]-benzodiazepin-7(4H)-one, hydrochloride salt

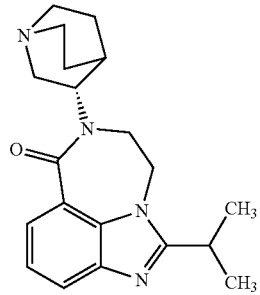 [SMILES: CC(C)c1nc2cccc3c2n1CCN([C@@H]1CN2CCC1CC2)C3=O]

Step A: To a stirred solution of methyl 3-amino-2-(2,2-dimethoxyethylamino)benzoate (0.5 g, 2.0 mmol) from Step C of Example 13 in DMF (15 mL) and H₂O (0.5 mL) were added oxone (0.8 g, 1.3 mmol) and iso-butyraldehyde (0.2 mL, 2.2 mmol) and the reaction was stirred overnight at room temperature. The reaction mixture was washed with saturated aqueous sodium bicarbonate, re-extracted with methylene chloride, dried (Na₂SO₄), filtered, and concentrated under reduced pressure. The crude material was purified by column chromatography (silica gel, 0% to 30% ethyl acetate in hexanes) to afford methyl 1-(2,2-dimethoxyethyl)-2-isopropyl-1H-benzo[d]imidazole-7-carboxylate (0.5 g, 85%): ¹H NMR (500 MHz, DMSO-d₆) δ 7.79 (dd, J=8.0, 1.0 Hz, 1H), 7.56 (dd, J=7.5, 1.0 Hz, 1H), 7.22 (t, J=8.0 Hz, 1H), 4.61 (d, J=5.0 Hz, 2H), 4.38 (t, J=5.0 Hz, 1H), 3.90 (s, 3H), 3.38-3.33 (m, 1H), 3.19 (s, 6H), 1.32 (d, J=7.0 Hz, 6H); MS (ESI+) m/z 306 (M+H).

Step B: To a stirred solution of methyl 1-(2,2-dimethoxyethyl)-2-isopropyl-1H-benzo[d]imidazole-7-carboxylate from Step A above in methylene chloride and water was added trifluoroacetic acid and the reaction was stirred at room temperature for 1.5 h and then heated at reflux for 2 h. The reaction mixture was concentrated under reduced pressure to remove the excess trifluoroacetic acid, diluted with methylene chloride, washed with saturated aqueous sodium bicarbonate, re-extracted with methylene chloride, dried (Na$_2$SO$_4$), filtered, and concentrated under reduced pressure to give methyl 2-isopropyl-1-(2-oxoethyl)-1H-benzo[d]imidazole-7-carboxylate: $^1$H NMR (300 MHz, DMSO-d$_6$) δ 9.69 (s, 1H), 7.87 (dd, J=8.1, 0.9 Hz, 1H), 7.68 (dd, J=7.5, 0.9 Hz, 1H), 7.26 (t, J=7.8 Hz, 1H), 5.44 (s, 2H), 3.84 (s, 3H), 3.22-3.17 (m, 1H), 1.34-1.27 (m, 6H); MS (ESI+) m/z 261 (M+H).

Step C: The procedure described in Step F of Example 13 was used to convert methyl 2-isopropyl-1-(2-oxoethyl)-1H-benzo[d]imidazole-7-carboxylate from Step B above and (S)-(−)-3-aminoquinuclidine dihydrochloride to (S)-methyl 2-isopropyl-1-(2-(quinuclidin-3-ylamino)ethyl)-1H-benzo[d]imidazole-7-carboxylate, except that 1,4-dioxane was used as the solvent: MS (ESI+) m/z 371 (M+H).

Step D: The procedure described in Step G of Example 13 was used to convert (S)-methyl 2-isopropyl-1-(2-(quinuclidin-3-ylamino)ethyl)-1H-benzo[d]imidazole-7-carboxylate from Step C above to lithium (S)-2-isopropyl-1-(2-(quinuclidin-3-ylamino)ethyl)-1H-benzo[d]imidazole-7-carboxylate: MS (ESI+) m/z 357 (M+H).

Step E: The procedure described in Step H of Example 13 was used to convert lithium (S)-2-isopropyl-1-(2-(quinuclidin-3-ylamino)ethyl)-1H-benzo[d]imidazole-7-carboxylate from Step D above to 2-isopropyl-6-((S)-quinuclidin-3-yl)-5,6-dihydroimidazo[4,5,1-jk][1,4]benzodiazepin-7(4H)-one: $^1$H NMR (500 MHz, DMSO-d$_6$) δ 7.82 (d, J=7.5 Hz, 1H), 7.76 (dd, J=8.0, 1.0 Hz, 1H), 7.25 (t, J=8.0 Hz, 1H), 4.89-4.49 (m, 2H), 4.48-4.01 (m, 1H), 3.98-3.41 (m, 1H), 3.24-3.12 (m, 3H), 3.04-2.73 (m, 5H), 1.96-1.95 (m, 1H), 1.75-1.58 (m, 3H), 1.44-1.31 (m, 7H); MS (ESI+) m/z 339 (M+H).

Step F: The procedure described in Step I of Example 13 was used to convert 2-isopropyl-6-((S)-quinuclidin-3-yl)-5,6-dihydroimidazo[4,5,1-jk][1,4]benzodiazepin-7(4H)-one from Step E above to the corresponding hydrochloride salt (white solid): $^1$H NMR (500 MHz, DMSO-d$_6$) δ 10.29 (br s, 1H), 7.84 (d, J=8.0 Hz, 1H), 7.80 (dd, J=8.0, 1.0 Hz, 1H), 7.27 (t, J=8.0 Hz, 1H), 4.73-4.44 (m, 2H), 4.43-4.01 (m, 1H), 3.98-3.69 (m, 1H), 3.68-3.16 (m, 8H), 2.28-2.27 (m, 1H), 1.92-1.77 (m, 4H), 1.37-1.33 (m, 6H); MS (ESI+) m/z 339 (M+H).

Example 20

Preparation of 2-phenyl-6-((R)-quinuclidin-3-yl)-5,6-dihydroimidazo[4,5,1-jk][1,4]benzodiazepin-7(4H)-one, hydrochloride salt

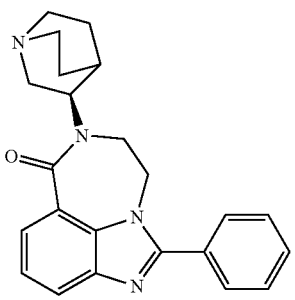 [SMILES: O=C1c2cccc3nc(-c4ccccc4)n(c23)CCN1[C@H]1CN2CCC1CC2]

Step A: Methyl 3-amino-2-(2,2-dimethoxyethylamino)benzoate (922 mg, 3.6 mmol) from Step C of Example 13 was stirred in glacial acetic acid (2.5 mL) and (trimethoxymethyl)benzene (2.0 g, 10.9 mmol) at 70° C. for 3 h. The reaction mixture was cooled to room temperature, concentrated under reduced pressure, and purified by column chromatography (silica gel, 80:20 hexanes/ethyl acetate) to give methyl 1-(2,2-dimethoxyethyl)-2-phenyl-1H-benzo[d]imidazole-7-carboxylate as a brown oil (1.0 g, 83%): $^1$H NMR (500 MHz, CDCl$_3$) δ 7.99 (d, J=8.0 Hz, 1H), 7.95 (d, J=8.0 Hz, 1H), 7.72-7.70 (m, 2H), 7.53-7.51 (m, 3H), 7.33 (t, J=8.0 Hz, 1H), 4.76 (d, J=5.0 Hz, 2H), 4.24 (t, J=5.0 Hz, 1H), 3.99 (s, 3H), 3.07 (s, 6H); MS (ESI+) m/z 341 (M+H).

Step B: Methyl 1-(2,2-dimethoxyethyl)-2-phenyl-1H-benzo[d]imidazole-7-carboxylate (719 mg, 2.1 mmol) from Step A above was heated to reflux in 1:1 trifluoroacetic acetic acid/water (6 mL) and 1,2-dichloroethane (2 mL) for 2 h. The reaction mixture was concentrated, diluted with ethyl acetate, and pH adjusted to 8 with saturated aqueous sodium bicarbonate. The aqueous phase was extracted with additional ethyl acetate and the combined organic extracts were washed with brine, dried over sodium sulfate, filtered, and concentrated under reduced pressure to give methyl 1-(2-oxoethyl)-2-phenyl-1H-benzo[d]imidazole-7-carboxylate as a light pink solid (526 mg, 85%): $^1$H NMR (500 MHz, CDCl$_3$) δ 9.80 (s, 1H), 8.06 (d, J=8.0 Hz, 1H), 7.98 (d, J=8.0 Hz, 1H), 7.63 (d, J=8.0 Hz, 2H), 7.54-7.50 (m, 3H), 7.37 (d, J=7.5 Hz, 1H), 5.26 (s, 2H), 3.92 (s, 3H).

Step C: The procedure described in Step F of Example 13 was used to convert 1-(2-oxoethyl)-2-phenyl-1H-benzo[d]imidazole-7-carboxylate from Step B above and (R)-(+)-3-aminoquinuclidine dihydrochloride to (R)-methyl 2-phenyl-1-(2-(quinuclidin-3-ylamino)ethyl)-1H-benzo[d]imidazole-7-carboxylate, providing the product as a white paste: $^1$H NMR (500 MHz, CDCl$_3$) δ 8.02 (d, J=12.0 Hz, 1H), 7.86 (d, J=12.0 Hz, 1H), 7.74-7.72 (m, 2H), 7.54-7.52 (m, 3H), 7.35 (t, J=13.0 Hz, 1H), 4.73 (t, J=10.5 Hz, 2H), 4.00 (s, 3H), 2.88-2.59 (m, 7H), 2.35 (s, 1H), 1.98 (s, 1H), 1.71-1.03 (m, 6H); MS (ESI+) m/z 405 (M+H).

Step D: The procedure described in Step G of Example 13 was used to convert (R)-methyl 2-phenyl-1-(2-(quinuclidin-3-ylamino)ethyl)-1H-benzo[d]imidazole-7-carboxylate from Step C above to lithium (R)-2-phenyl-1-(2-(quinuclidin-3-ylamino)ethyl)-1H-benzo[d]imidazole-7-carboxylate, providing the product as a white solid: $^1$H NMR (500 MHz, DMSO-d$_6$) δ 7.71 (d, J=7.5 Hz, 2H), 7.56-7.50 (m, 3H), 7.46 (d, J=7.5 Hz, 1H), 7.24 (d, J=7.5 Hz, 1H), 7.07 (d, J=7.5 Hz, 1H), 4.77-4.64 (m, 2H), 2.64-2.18 (m, 7H), 1.89-1.85 (m, 1H), 1.44-0.96 (m, 7H); MS (ESI+) m/z 391 (M+H).

Step E: The procedure described in Step H of Example 13 was used to convert lithium (R)-2-phenyl-1-(2-(quinuclidin-3-ylamino)ethyl)-1H-benzo[d]imidazole-7-carboxylate from Step D above to 2-phenyl-6-((R)-quinuclidin-3-yl)-5,6-dihydroimidazo[4,5,1-jk][1,4]benzodiazepin-7(4H)-one, providing the product as a white solid: $^1$H NMR (500 MHz, MeOD) δ 8.03 (d, J=7.5 Hz, 1H), 7.93 (d, J=7.5 Hz, 1H), 7.89-7.87 (m, 2H), 7.64-7.61 (m, 3H), 7.46 (d, J=7.5 Hz, 1H), 4.63-4.49 (m, 2H), 4.31-4.34 (m, 3H), 3.23-2.86 (m, 6H), 2.12-1.96 (m, 1H), 1.90-1.64 (m, 4H); MS (ESI+) m/z 373 (M+H).

Step F: The procedure described in Step I of Example 13 was used to convert 2-phenyl-6-((R)-quinuclidin-3-yl)-5,6-dihydroimidazo[4,5,1-jk][1,4]benzodiazepin-7(4H)-one from Step E above to the corresponding hydrochloride salt (white solid): $^1$H NMR (500 MHz, D$_2$O) δ 8.25-8.22 (m, 1H), 8.11 (d, J=8.0 Hz, 1H), 7.93 (d, J=7.5 Hz, 2H), 7.88 (t, J=7.5

Hz, 1H), 7.81 (t, J=8.0 Hz, 3H), 4.94-4.81 (m, 3H), 4.44-3.55 (m, 5H), 3.54-3.30 (m, 3H), 2.61-2.02 (m, 5H); MS (ESI+) m/z 373 (M+H).

Example 21

Preparation of 2-phenyl-6-((S)-quinuclidin-3-yl)-5,6-dihydroimidazo[4,5,1-jk][1,4]benzodiazepin-7(4H)-one, hydrochloride salt

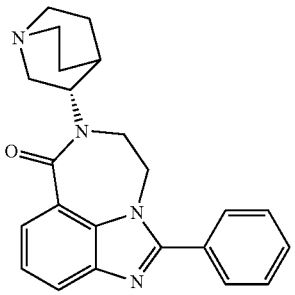 [SMILES: O=C1c2cccc3nc(-c4ccccc4)n(c23)CCN1[C@@H]1CN2CCC1CC2]

Step A: The procedure described in Step F of Example 13 was used to convert 1-(2-oxoethyl)-2-phenyl-1H-benzo[d]imidazole-7-carboxylate from Step B of Example 20 and (S)-(−)-3-aminoquinuclidine dihydrochloride to (S)-methyl 2-phenyl-1-(2-(quinuclidin-3-ylamino)ethyl)-1H-benzo[d]imidazole-7-carboxylate, providing the product as a white paste: $^1$H NMR (500 MHz, DMSO-$d_6$) δ 7.95 (d, J=8.0 Hz, 1H), 7.76-7.75 (m, 2H), 7.72 (d, J=8.0 Hz, 1H), 7.59-7.58 (m, 3H), 7.36 (t, J=8.0 Hz, 1H), 4.52 (t, J=6.0 Hz, 2H), 3.95 (s, 3H), 2.70-2.54 (m, 1H), 2.48-2.30 (m, 5H), 2.20-2.10 (m, 1H), 1.95-1.77 (m, 2H), 1.50-1.21 (m, 4H), 1.17-1.00 (m, 1H), 0.99-0.84 (m, 1H); MS (ESI+) m/z 405 (M+H).

Step B: The procedure described in Step G of Example 13 was used to convert (S)-methyl 2-phenyl-1-(2-(quinuclidin-3-ylamino)ethyl)-1H-benzo[d]imidazole-7-carboxylate from Step A above to lithium (S)-2-phenyl-1-(2-(quinuclidin-3-ylamino)ethyl)-1H-benzo[d]imidazole-7-carboxylate, providing the product as a white solid: $^1$H NMR (500 MHz, MeOD) δ 7.76-7.73 (m, 2H), 7.67 (d, J=8.0 Hz, 1H), 7.61-7.56 (m, 3H), 7.51 (d, J=7.5 Hz, 1H), 7.28 (t, J=8.0 Hz, 1H), 4.76-4.68 (m, 2H), 2.90-2.74 (m, 2H), 2.70-2.60 (m, 5H), 2.59-2.44 (m, 1H), 2.09-2.05 (m, 1H), 1.62-1.45 (m, 3H), 1.40-1.23 (m, 2H), 1.22-1.10 (m, 1H); MS (ESI+) m/z 391 (M+H).

Step C: The procedure described in Step H of Example 13 was used to convert lithium (S)-2-phenyl-1-(2-(quinuclidin-3-ylamino)ethyl)-1H-benzo[d]imidazole-7-carboxylate from Step B above to 2-phenyl-6-((S)-quinuclidin-3-yl)-5,6-dihydroimidazo[4,5,1-jk][1,4]benzodiazepin-7(4H)-one, providing the product as a white solid: $^1$H NMR (500 MHz, DMSO-$d_6$) δ 7.93-7.89 (m, 3H), 7.62-7.58 (m, 2H), 7.39 (t, J=8.0 Hz, 1H), 7.27 (s, 2H), 6.66 (s, 2H), 4.67-3.49 (m, 5H), 3.17-2.85 (m, 5H), 2.03-1.24 (m, 4H); MS (ESI+) m/z 373 (M+H).

Step D: The procedure described in Step I of Example 13 was used to convert 2-phenyl-6-((S)-quinuclidin-3-yl)-5,6-dihydroimidazo[4,5,1-jk][1,4]benzodiazepin-7(4H)-one from Step C above to the corresponding hydrochloride salt (white solid): $^1$H NMR (500 MHz, D$_2$O) δ 8.28-8.25 (m, 1H), 8.15 (d, J=8.0 Hz, 1H), 7.94 (d, J=8.0 Hz, 2H), 7.90 (t, J=8.0 Hz, 1H), 7.84-7.79 (m, 3H), 4.94-4.83 (m, 3H), 4.38-3.55 (m, 5H), 3.53-3.28 (m, 3H), 2.62-2.10 (m, 5H); MS (ESI+) m/z 373 (M+H).

Example 22

Preparation of 2-(4-fluorophenyl)-6-((S)-quinuclidin-3-yl)-5,6-dihydroimidazo[4,5,1-jk][1,4]benzodiazepin-7(4H)-one, hydrochloride salt

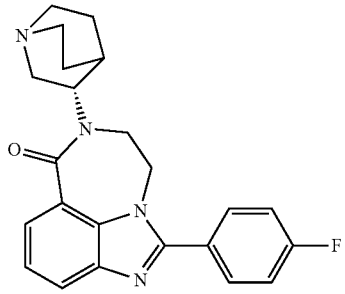 [SMILES: O=C1c2cccc3nc(-c4ccc(F)cc4)n(c23)CCN1[C@@H]1CN2CCC1CC2]

Step A: To a stirred solution of methyl 3-amino-2-(2,2-dimethoxyethylamino)benzoate (1.0 g, 3.9 mmol) from Step C of Example 13 in DMF (9 mL) and H$_2$O (0.3 mL) were added oxone (1.6 g, 2.6 mmol) and 4-fluorobenzaldehyde (0.5 mL, 4.3 mmol) and the mixture was stirred overnight at room temperature. The reaction mixture was washed with saturated aqueous sodium bicarbonate, re-extracted with methylene chloride, dried (Na$_2$SO$_4$), filtered, and concentrated under reduced pressure to give the crude material which was purified by column chromatography (silica gel, 5% to 100% ethyl acetate in hexanes) to afford methyl 1-(2,2-dimethoxyethyl)-2-(4-fluorophenyl)-1H-benzo[d]imidazole-7-carboxylate (1.1 g, 79%): $^1$H NMR (500 MHz, CDCl$_3$) δ 7.97 (dd, J=8.0, 1.0 Hz, 1H), 7.80 (dd, J=8.0, 1.0 Hz, 1H), 7.73-7.70 (m, 2H), 7.32 (t, J=8.0 Hz, 1H), 7.24-7.20 (m, 2H), 4.72 (d, J=5.0 Hz, 2H), 4.24 (t, J=5.0 Hz, 1H), 3.94 (s, 3H), 3.38-3.33 (m, 1H), 3.19 (s, 6H); MS (ESI+) m/z 359 (M+H).

Step B: The solution of methyl 1-(2,2-dimethoxyethyl)-2-(4-fluorophenyl)-1H-benzo[d]imidazole-7-carboxylate (1.1 g, 3.1 mmol) from Step A above in 1,2-dichloroethane (5 mL) with water (3 mL) and trifluoroacetic acid (3 mL) was stirred at reflux for 2.5 h. The reaction mixture was concentrated under reduced pressure, the residue was diluted with methylene chloride, neutralized with saturated aqueous sodium bicarbonate, dried (Na$_2$SO$_4$), filtered, and concentrated under reduced pressure to afford methyl 2-(4-fluorophenyl)-1-(2-oxoethyl)-1H-benzo[d]imidazole-7-carboxylate (820 mg, 84%) as a clear oil: $^1$H NMR (500 MHz, CDCl$_3$) δ 9.80 (s, 1H), 8.05 (d, J=8.0, Hz, 1H), 7.98 (d, J=7.5, Hz, 1H), 7.62 (dd, J=7.5, 5.0 Hz, 2H), 7.36 (t, J=8.0 Hz, 1H), 7.21 (t, J=7.5 Hz, 2H), 5.25 (s, 2H), 3.92 (s, 3H); MS (ESI+) m/z 313 (M+H).

Step C: The procedure described in Step F of Example 13 was used to convert methyl 2-(4-fluorophenyl)-1-(2-oxoethyl)-1H-benzo[d]imidazole-7-carboxylate from Step B above and (S)-3-aminoquinuclidine dihydrochloride to (S)-methyl 2-(4-fluorophenyl)-1-(2-(quinuclidin-3-ylamino)ethyl)-1H-benzo[d]imidazole-7-carboxylate, except that 1,4-dioxane was used as the solvent: MS (ESI+) m/z 423 (M+H).

Step D: The procedure described in Step G of Example 13 was used to convert (S)-methyl 2-(4-fluorophenyl)-1-(2-(quinuclidin-3-ylamino)ethyl)-1H-benzo[d]imidazole-7-carboxylate from Step C above to lithium (S)-2-(4-fluorophenyl)-1-(2-(quinuclidin-3-ylamino)ethyl)-1H-benzo[d]imidazole-7-carboxylate: MS (ESI+) m/z 408 (M+H).

Step E: The procedure described in Step H of Example 13 was used to convert lithium (S)-2-(4-fluorophenyl)-1-(2-(quinuclidin-3-ylamino)ethyl)-1H-benzo[d]imidazole-7-carboxylate from Step D above to 2-(4-fluorophenyl)-6-((S)-quinuclidin-3-yl)-5,6-dihydroimidazo[4,5,1-jk][1,4]benzodiazepin-7(4H)-one: $^1$H NMR (500 MHz, CD$_3$OD) δ 8.02 (d, J=7.5 Hz, 1H), 7.95-7.90 (m 3H), 7.44 (t, J=8.0 Hz, 1H), 7.40-7.34 (m, 2H), 4.64-4.44 (m, 2H), 4.40-4.20 (m, 1H), 3.96-3.66 (m, 2H), 3.20-3.08 (m, 2H), 2.98-2.82 (m, 3H), 2.32-2.10 (m, 2H), 1.94-1.60 (m, 4H); MS (ESI+) m/z 391 (M+H).

Step F: The procedure described in Step I of Example 13 was used to convert 2-(4-fluorophenyl)-6-((S)-quinuclidin-3-yl)-5,6-dihydroimidazo[4,5,1-jk][1,4]benzodiazepin-7(4H)-one from Step E above to the corresponding hydrochloride salt (white solid): $^1$H NMR (500 MHz, CD$_3$OD) δ 8.29 (s, 1H), 8.08-8.03 (m, 3H), 7.76 (t, J=8.0 Hz, 1H), 7.56-7.50 (m, 2H), 4.95-4.44 (m, 3H), 4.34-3.60 (m, 5H), 3.50-3.34 (m, 3H), 2.60-1.96 (m, 5H); MS (ESI+) m/z 391 (M+H).

Example 23

Preparation of 2-(2-chlorophenyl)-6-((S)-quinuclidin-3-yl)-5,6-dihydroimidazo[4,5,1-jk][1,4]benzodiazepin-7(4H)-one, hydrochloride salt

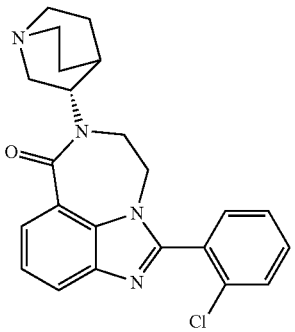 [SMILES: O=C1c2cccc3nc(-c4ccccc4Cl)n(c23)CCN1[C@@H]1CN2CCC1CC2]

Step A: Methyl 3-amino-2-(2,2-dimethoxyethylamino) benzoate (498 mg, 2.0 mmol) from Step C of Example 13, 2-chlorobenzaldehyde (303 mg, 2.15 mmol) and 4 Å molecular sieves were stirred in methylene chloride (6 mL) at room temperature for 1 h. To this mixture was added iodobenzene 1,1-diacetate (1.26 g, 3.92 mmol) and the reaction mixture was heated (external temperature=55° C.) for 10 min. The reaction was quenched with saturated aqueous sodium bicarbonate, 10% aqueous sodium thiosulfate and pH adjusted to 8. The organic phase was extracted with methylene chloride, washed with brine, dried over sodium sulfate, filtered, and concentrated under reduced pressure. The crude material was purified by column chromatography (silica gel, 3:1 hexanes/ethyl acetate) to give methyl 2-(2-chlorophenyl)-1-(2,2-dimethoxyethyl)-1-benzo[d]imidazole-7-carboxylate as a brown oil (275 mg, 38%): $^1$H NMR (500 MHz, MeOD) δ 7.91 (d, J=8.0 Hz, 1H), 7.82 (d, J=7.5 Hz, 1H), 7.66-7.60 (m, 3H), 7.56 (d, J=7.5 Hz, 1H), 7.40 (t, J=7.5 Hz, 1H), 4.28 (t, J=4.5 Hz, 1H), 4.27-4.08 (m, 2H), 3.98 (s, 3H), 3.12 (s, 3H), 3.09 (s, 3H); MS (ESI+) m/z 375 (M+H).

Step B: The procedure described in Step E of Example 13 was used to convert methyl 2-(2-chlorophenyl)-1-(2,2-dimethoxyethyl)-1H-benzo[d]imidazole-7-carboxylate from Step A above to methyl 2-(2-chlorophenyl)-1-(2-oxoethyl)-1H-benzo[d]imidazole-7-carboxylate, providing the product as a red liquid: $^1$H NMR (500 MHz, CDCl$_3$) δ 9.67 (s, 1H), 8.08 (d, J=8.0 Hz, 1H), 8.01 (d, J=8.0 Hz, 1H), 7.55 (m, 3H), 7.43 (t, J=7.5 Hz, 1H), 7.39 (t, J=8.0 Hz, 1H), 3.91 (s, 3H), 3.73 (s, 2H); MS (ESI+) m/z 329 (M+H).

Step C: The procedure described in Step F of Example 13 was used to convert methyl 2-(2-chlorophenyl)-1-(2-oxoethyl)-1H-benzo[d]imidazole-7-carboxylate from Step B above and (S)-(−)-3-aminoquinuclidine dihydrochloride to (S)-methyl 2-(2-chlorophenyl)-1-(2-(quinuclidin-3-ylamino)ethyl)-1H-benzo[d]imidazole-7-carboxylate, providing the product as a light pink paste: $^1$H NMR (500 MHz, CDCl$_3$) δ 8.03 (d, J=8.0 Hz, 1H), 7.90 (d, J=8.0 Hz, 1H), 7.60 (d, J=7.5 Hz, 1H), 7.56 (d, J=8.0 Hz, 1H), 7.51 (t, J=7.5 Hz, 1H), 7.44 (t, J=7.5 Hz, 1H), 7.35 (t, J=8.0 Hz, 1H), 3.98 (s, 3H), 2.97-2.82 (m, 1H), 2.80-2.51 (m, 6H), 2.47-2.32 (m, 2H), 1.65-1.36 (m, 4H), 1.34-1.00 (m, 3H); MS (ESI+) m/z 439 (M+H).

Step D: The procedure described in Step G of Example 13 was used to convert (S)-methyl 2-(2-chlorophenyl)-1-(2-(quinuclidin-3-ylamino)ethyl)-1H-benzo[d]imidazole-7-carboxylate from Step C above to lithium (S)-2-(2-chlorophenyl)-1-(2-(quinuclidin-3-ylamino)ethyl)-1H-benzo[d]imidazole-7-carboxylate, providing the product as a white solid: $^1$H NMR (500 MHz, MeOD) δ 7.67-7.64 (m, 3H), 7.62 (t, J=8.0 Hz, 1H), 7.55-7.51 (m, 2H), 7.30 (t, J=7.5 Hz, 1H), 4.80-4.20 (m, 2H), 3.10-2.75 (m, 2H), 2.74-2.23 (m, 7H), 2.22-1.96 (m, 1H), 1.85-1.46 (m, 3H), 1.45-1.20 (m, 2H); MS (ESI+) m/z 425 (M+H).

Step E: The procedure described in Step H of Example 13 was used to convert lithium (S)-2-(2-chlorophenyl)-1-(2-(quinuclidin-3-ylamino)ethyl)-1H-benzo[d]imidazole-7-carboxylate from Step D above to 2-(2-chlorophenyl)-6-((S)-quinuclidin-3-yl)-5,6-dihydroimidazo[4,5,1-jk][1,4]benzodiazepin-7(4H)-one, providing the product as a pink solid: $^1$H NMR (500 MHz, MeOD) δ 8.11 (d, J=8.0 Hz, 1H), 7.96 (d, J=8.0 Hz, 1H), 7.68-7.62 (m, 3H), 7.57 (t, J=7.5 Hz, 1H), 7.49 (t, J=8.0 Hz, 1H), 4.91-3.37 (m, 6H), 3.27-2.82 (m, 5H), 2.25-1.97 (m, 1H), 1.92-1.19 (m, 4H); MS (ESI+) m/z 407 (M+H).

Step F: The procedure described in Step I of Example 13 was used to convert 2-(2-chlorophenyl)-6-((S)-quinuclidin-3-yl)-5,6-dihydroimidazo[4,5,1-jk][1,4]benzodiazepin-7 (4H)-one from Step E above to the corresponding hydrochloride salt (white solid): $^1$H NMR (500 MHz, D$_2$O) δ 8.43 (s, 1H), 8.16 (d, J=8.0 Hz, 1H), 7.94-7.86 (m, 4H), 7.75-7.72 (m, 1H), 4.81-4.02 (m, 5H), 4.01-3.54 (m, 3H), 3.53-3.31 (m, 4H), (m, 4H); MS (ESI+) m/z 407 (M+H).

Example 24

Preparation of 6-((R)-quinuclidin-3-yl)-5,6-dihydroimidazo[4,5,1-jk][1,4]benzodiazepine-2,7(1H,4H)-dione, hydrochloride salt

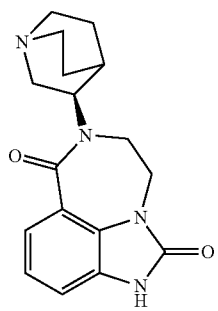 [SMILES: O=C1c2cccc3[nH]c(=O)n(c23)CCN1[C@H]1CN2CCC1CC2]

Step A: The solution of methyl 3-amino-2-(2,2-dimethoxyethylamino)benzoate (0.7 g, 2.4 mmol) from Step C of Example 13 in THF (23 mL) with di(1H-imidazol-2-yl)methanone (0.4 g, 2.6 mmol) was refluxed overnight. The reaction mixture was washed with saturated aqueous sodium bicarbonate, re-extracted with methylene chloride, dried (Na$_2$SO$_4$), filtered, and concentrated under reduced pressure to give the crude material which was purified by column chromatography (silica gel, 0% to 100% ethyl acetate in hexanes) to afford methyl 3-(2,2-dimethoxyethyl)-2-oxo-2,3-dihydro-1H-benzo[d]imidazole-4-carboxylate (0.4 g, 60%): $^1$H NMR (300 MHz, DMSO-d$_6$) δ 11.29 (s, 1H), 7.30 (dd, J=7.8, 1.2 Hz, 1H), 7.17 (dd, J=7.8, 1.5 Hz, 1H), 7.05 (t, J=7.8 Hz, 1H), 4.31 (t, J=5.4 Hz, 1H), 4.23-4.22 (m, 2H), 3.85 (s, 3H), 3.18 (s, 6H).

Step B: The solution of 3-(2,2-dimethoxyethyl)-2-oxo-2,3-dihydro-1H-benzo[d]imidazole-4-carboxylate (0.4 g, 1.4 mmol) in methylene chloride (10 mL) with water (3 mL) and TFA (3 mL) was stirred at room temperature for 1.5 h. The reaction mixture was concentrated under reduced pressure to remove the excess trifluoroacetic acid, diluted with methylene chloride, washed with saturated aqueous sodium bicarbonate, re-extracted with methylene chloride, dried (Na$_2$SO$_4$), filtered, and concentrated under reduced pressure to give methyl 2-oxo-3-(2-oxoethyl)-2,3-dihydro-1H-benzo[d]imidazole-4-carboxylate (0.2 g, 61%): $^1$H NMR (500 MHz, DMSO-d$_5$) δ 11.43 (s, 1H), 9.61 (s, 1H), 7.45 (d, J=8.0 Hz, 1H), 7.26 (d, J=8.0 Hz, 1H), 7.12-7.09 (m, 1H), 4.95-4.94 (m, 2H), 3.79 (s, 3H); MS (ESI+) m/z 234 (M+H).

Step C: The procedure described in Step F of Example 13 was used to convert methyl 2-oxo-3-(2-oxoethyl)-2,3-dihydro-1H-benzo[d]imidazole-4-carboxylate from Step B above and (R)-(+)-3-aminoquinuclidine dihydrochloride to (R)-methyl 2-oxo-3-(2-(quinuclidin-3-ylamino)ethyl)-2,3-dihydro-1H-benzo[d]imidazole-4-carboxylate, except that 1,4-dioxane was used as the solvent: MS (ESI+) m/z 345 (M+H).

Step D: The procedure described in Step G of Example 13 was used to convert (R)-methyl 2-oxo-3-(2-(quinuclidin-3-ylamino)ethyl)-2,3-dihydro-1H-benzo[d]imidazole-4-carboxylate from Step C above to lithium (R)-2-oxo-3-(2-(quinuclidin-3-ylamino)ethyl)-2,3-dihydro-1H-benzo[d]imidazole-4-carboxylate: MS (ESI+) m/z 299 (M+H).

Step E: The procedure described in Step H of Example 13 was used to convert lithium (R)-2-oxo-3-(2-(quinuclidin-3-ylamino)ethyl)-2,3-dihydro-1H-benzo[d]imidazole-4-carboxylate from Step D above to 6-((R)-quinuclidin-3-yl)-5,6-dihydroimidazo[4,5,1-jk][1,4]benzodiazepine-2,7(1H,4H)-dione: MS (ESI+) m/z 312 (M+H).

Step F: The procedure described in Step I of Example 13 was used to convert 6-((R)-quinuclidin-3-yl)-5,6-dihydroimidazo[4,5,1-jk][1,4]benzodiazepine-2,7(1H,4H)-dione from Step E above to the corresponding hydrochloride salt (off-white solid): $^1$H NMR (500 MHz, DMSO-d$_6$) δ 11.19 (s, 1H), 10.14 (s, 1H), 7.58 (d, J=8.0 Hz, 1H), 7.17 (d, J=7.5 Hz, 1H), 7.10-7.07 (m, 1H), 4.72-4.70 (m, 1H), 4.44-3.39 (m, 7H), 3.27-3.17 (m, 3H), 2.31-2.30 (m, 1H), 1.94-1.75 (m, 4H); MS (ESI+) m/z 313 (M+H).

Example 25

Preparation of 6-((S)-quinuclidin-3-yl)-5,6-dihydroimidazo[4,5,1-jk][1,4]benzodiazepine-2,7(1H,4H)-dione, hydrochloride salt

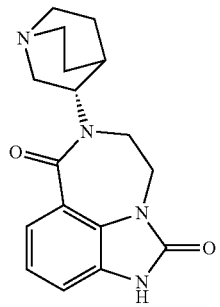 [SMILES: O=C1c2cccc3[nH]c(=O)n(c23)CCN1[C@@H]1CN2CCC1CC2]

Step A: The procedure described in Step F of Example 13 was used to convert methyl 2-oxo-3-(2-oxoethyl)-2,3-dihydro-1H-benzo[d]imidazole-4-carboxylate from Step B of Example 19 and (S)-(−)-3-aminoquinuclidine dihydrochloride to (S)-methyl 2-oxo-3-(2-(quinuclidin-3-ylamino)ethyl)-2,3-dihydro-1H-benzo[d]imidazole-4-carboxylate, except that 1,4-dioxane was used as the solvent: MS (ESI+) m/z 345 (M+H).

Step B: The procedure described in Step G of Example 13 was used to convert (S)-methyl 2-oxo-3-(2-(quinuclidin-3-ylamino)ethyl)-2,3-dihydro-1H-benzo[d]imidazole-4-carboxylate from Step A above to lithium (S)-2-oxo-3-(2-(quinuclidin-3-ylamino)ethyl)-2,3-dihydro-1H-benzo[d]imidazole-4-carboxylate: MS (ESI+) m/z 299 (M+H).

Step C: The procedure described in Step H of Example 13 was used to convert lithium (S)-2-oxo-3-(2-(quinuclidin-3-ylamino)ethyl)-2,3-dihydro-1H-benzo[d]imidazole-4-carboxylate from Step B above to 6-((S)-quinuclidin-3-yl)-5,6-dihydroimidazo[4,5,1-jk][1,4]benzodiazepine-2,7(1H,4H)-dione: MS (ESI+) m/z 312 (M+H).

Step D: The procedure described in Step I of Example 13 was used to convert 6-((S)-quinuclidin-3-yl)-5,6-dihydroimidazo[4,5,1-jk][1,4]benzodiazepine-2,7(1H,4H)-dione from Step C above to the corresponding hydrochloride salt (white solid): $^1$H NMR (500 MHz, DMSO-d$_6$) δ 11.19 (s, 1H), 10.14 (s, 1H), 7.58 (d, J=8.0 Hz, 1H), 7.17 (d, J=7.5 Hz, 1H), 7.10-7.07 (m, 1H), 4.72-4.70 (m, 1H), 4.44-3.39 (m, 7H), 3.27-3.17 (m, 3H), 2.31-2.30 (m, 1H), 1.94-1.75 (m, 4H); MS (ESI+) m/z 313 (M+H).

Example 26

Preparation of 6-((S)-quinuclidin-3-yl)-5,6-dihydro-1H-[1,2,5]thiadiazolo[4,3,2-jk][1,4]benzodiazepin-7(4H)-one 2,2-dioxide, hydrochloride salt

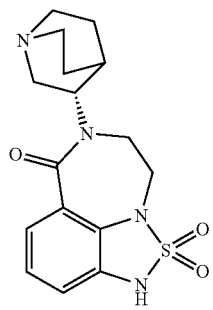 [SMILES: O=C1c2cccc3c2N(CCN1[C@@H]1CN2CCC1CC2)S(=O)(=O)N3]

Step A: To a stirred solution of 2-chloro-3-nitrobenzoic acid (1.0 g, 5.0 mmol) in anhydrous methanol (10 mL) at 0° C. was added thionyl chloride (0.5 mL, 7.4 mmol) dropwise and the reaction mixture was stirred overnight at reflux. The mixture was diluted with methanol and concentrated under reduced pressure to remove the excess thionyl chloride. The residue was then re-dissolved in ethyl acetate, washed with saturated aqueous sodium bicarbonate, re-extracted with ethyl acetate, dried (Na$_2$SO$_4$), filtered, and concentrated under reduced pressure to give methyl 2-chloro-3-nitrobenzoate (1.1 g, 98%) as a white foam that was used in the next step without further purification: $^1$H NMR (300 MHz, DMSO-d$_6$) δ 8.21 (d, J=1.5 Hz, 1H), 8.07 (dd, J=7.8, 1.5 Hz, 1H), 7.73 (t, J=8.1 Hz, 1H), 3.91 (s, 3H).

Step B: To a stirred solution of methyl 2-chloro-3-nitrobenzoate (1.1 g, 4.9 mmol) from Step A above in THF (33 mL) was added triethylamine (0.8 mL, 6.0 mmol) followed by 2,2-dimethoxyethanamine (0.7 mL, 6.0 mmol) at room temperature. The reaction mixture was stirred overnight at reflux and then the suspension was concentrated under reduced pressure. The crude material was purified by column chromatography (silica gel, 0% to 10% ethyl acetate in hexanes) to afford methyl 2-(2,2-dimethoxyethylamino)-3-nitrobenzoate (1.4 g, 98%): $^1$H NMR (500 MHz, DMSO-d$_6$) δ 8.39 (t, J=4.5 Hz, 1H), 8.08-8.05 (m, 2H), 6.83 (t, J=8.0 Hz, 1H), 4.54 (t, J=5.0 Hz, 1H), 3.87 (s, 3H), 3.31 (s, 6H), 2.93 (t, J=5.0 Hz, 1H).

Step C: To an argon purged solution of methyl 2-(2,2-dimethoxyethylamino)-3-nitrobenzoate (1.4 g, 4.7 mmol) from Step B above in ethanol (50 mL) at room temperature was added 10% palladium on carbon. A hydrogen balloon was then attached and the suspension was stirred overnight at room temperature. The reaction mixture was filtered through celite and concentrated under reduced pressure to give methyl 3-amino-2-(2,2-dimethoxyethylamino)benzoate (1.2 g, quantitative yield) as a dark red oil: $^1$H NMR (300 MHz, DMSO-d$_6$) δ 7.06 (d, J=5.0 Hz, 1H), 6.85 (dd, J=7.8, 1.2 Hz, 1H), 6.74 (t, J=7.8 Hz, 1H), 6.06 (t, J=7.5 Hz, 1H), 4.84 (s, 2H), 4.38 (t, J=5.4 Hz, 1H), 3.80 (s, 3H), 3.23 (s, 6H), 3.04 (dd, J=7.2, 5.7 Hz, 2H); MS (ESI+) m/z 254 (M+H).

Step D: A solution of methyl 3-amino-2-(2,2-dimethoxyethylamino)benzoate (0.5 g, 2.0 mmol) from Step C above and sulfuric diamide (0.2 g, 2.4 mmol) in diglyme (2 mL) was added to boiling diglyme (5 mL) dropwise and continued to reflux for 35 min. The flask was cooled to room temperature and the solvent was removed in vacuo. The crude reaction was purified by column chromatography (silica gel, 0% to 100% ethyl acetate in hexanes) to afford methyl 3-(2,2-dimethoxyethyl)-1,3-dihydro-2,1,3-benzothiadiazole-4-carboxylate 2,2-dioxide (0.2 g, 27%): $^1$H NMR (500 MHz, DMSO-d$_6$) δ 7.08 (br s, 1H), 6.59 (dd, J=8.0, 1.5 Hz, 1H), 6.52 (t, J=8.0 Hz, 1H), 6.46 (dd, J=6.0, 1.5 Hz, 1H), 4.41 (t, J=5.0 Hz, 1H), 3.82 (d, J=5.0 Hz, 2H), 3.74 (s, 3H), 3.14 (s, 6H).

Step E: The solution of methyl 3-(2,2-dimethoxyethyl)-1,3-dihydro-2,1,3-benzothiadiazole-4-carboxylate 2,2-dioxide (0.2 g, 0.5 mmol) from Step D above in methylene chloride (10 mL) with water (1 mL) and trifluoroacetic acid (0.5 mL) was stirred at room temperature for 3.5 h. The reaction mixture was concentrated under reduced pressure and dried overnight under high vacuum to remove the excess trifluoroacetic acid, providing methyl 3-(2-oxoethyl)-1,3-dihydro-2,1,3-benzothiadiazole-4-carboxylate 2,2-dioxide (0.2 g): $^1$H NMR (500 MHz, DMSO-d$_6$) δ 9.56 (s, 1H), 7.42 (dd, J=7.5, 1.5 Hz, 1H), 7.19-6.99 (m, 2H), 4.71 (s, 2H), 3.78 (s, 3H).

Step F: The procedure described in Step F of Example 13 was used to convert methyl 3-(2-oxoethyl)-1,3-dihydro-2,1,3-benzothiadiazole-4-carboxylate 2,2-dioxide from Step E above and (S)-(−)-3-aminoquinuclidine dihydrochloride to (S)-methyl 3-[2-(quinuclidin-3-ylamino)ethyl]-1,3-dihydro-2,1,3-benzothiadiazole-4-carboxylate 2,2-dioxide: $^1$H NMR (500 MHz, DMSO-d$_6$) δ 11.43 (s, 1H), 9.61 (s, 1H), 7.45 (d, J=8.0 Hz, 1H), 7.26 (d, J=8.0 Hz, 1H), 7.12-7.09 (m, 1H), 4.95-4.94 (m, 2H), 3.79 (s, 3H); MS (ESI+) m/z 381 (M+H).

Step G: The procedure described in Step G of Example 13 was used to convert (S)-methyl 3-[2-(quinuclidin-3-ylamino)ethyl]-1,3-dihydro-2,1,3-benzothiadiazole-4-carboxylate 2,2-dioxide from Step F above to lithium (S)-3-[2-(quinuclidin-3-ylamino)ethyl]-1,3-dihydro-2,1,3-benzothiadiazole-4-carboxylate 2,2-dioxide: MS (ESI+) m/z 367 (M+H).

Step H: The procedure described in Step H of Example 13 was used to convert lithium (S)-3-[2-(quinuclidin-3-ylamino)ethyl]-1,3-dihydro-2,1,3-benzothiadiazole-4-carboxylate 2,2-dioxide from Step G above to 6-((S)-quinuclidin-3-yl)-5,6-dihydro-1H-[1,2,5]thiadiazolo[4,3,2-jk][1,4]benzodiazepin-7(4H)-one 2,2-dioxide: MS (ESI+) m/z 349 (M+H).

Step I: The procedure described in Step I of Example 13 was used to convert 6((S)-quinuclidin-3-yl)-5,6-dihydro-1H-[1,2,5]thiadiazolo[4,3,2-jk][1,4]benzodiazepin-7(4H)-one 2,2-dioxide from Step H above to the corresponding hydrochloride salt (off-white solid): $^1$H NMR (500 MHz, DMSO-d$_6$) δ 9.82 (br s, 1H), 7.38 (d, J=6.5 Hz, 1H), 6.99-6.95 (m, 2H), 4.66-4.65 (m, 1H), 4.07-4.04 (m, 1H), 3.95-3.90 (m, 2H), 3.79-3.65 (m, 2H), 3.52-3.44 (m, 2H), 3.39-3.22 (m, 4H), 2.29-2.27 (m, 1H), 1.97-1.80 (m, 4H); MS (ESI+) m/z 349 (M+H).

Example 27

Preparation of 6-(4-methoxybenzyl)-2-(quinuclidin-4-ylmethyl)-2,3,4,6-tetrahydro-1H-azepino[5,4,3-cd]indol-1-one hydrochloride

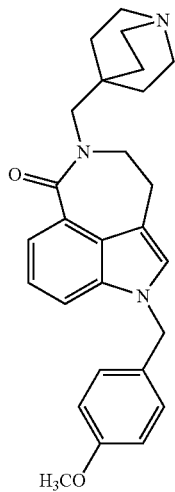 [SMILES: COc1ccc(Cn2cc3c4c(cccc42)C(=O)N(CC24CCN(CC2)CC4)CC3)cc1]

Quinuclidin-4-ylmethanamine was synthesized from quinuclidine-4-carbonitrile according to a reported method (PCT Publication No. WO 99/021855, which is hereby incorporated by reference in its entirety).

Step A: To a solution of methyl indole-4-carboxylate (10.0 g, 57.1 mmol) was added sodium hydride (60% dispersion in mineral oil (5.7 g, 142.8 mmol) in DMF (200 mL) at 0° C. The mixture was stirred under an atmosphere of nitrogen for 15 min. To this were added 4-methoxybenzyl bromide (10.7 g, 68.5 mmol) and tetrabuylammonium iodide (3.2 g, 8.6 mmol). The resulting mixture continued to stir for 10 min and then warmed to room temperature and stirred for 2.5 h. The mixture was quenched with sat. aqueous ammonium chloride (200 mL) and extracted with diethyl ether (3×500 mL). The combined organic layers were washed with brine (3×200 mL), dried ($Na_2SO_4$), filtered, and concentrated in vacuo. The crude material was purified by column chromatography (silica gel, 5 to 20% ethyl acetate in hexanes), providing methyl 1-(4-methoxybenzyl)-1H-indole-4-carboxylate (16.6 g, 98%) as a pale yellow oil: $^1$H NMR δ (500 MHz, $CDCl_3$) 7.90 (d, J=10.0 Hz, 1H), 7.49 (d, J=1.0 Hz, 1H), 7.26-7.25 (m, 1H), 7.20 (t, J=10.0 Hz, 1H), 7.16-7.15 (m, 1H), 7.04 (d, J=10.0 Hz, 2H), 6.82 (d, J=10.0 Hz, 2H), 5.29 (s, 2H), 3.98 (s, 3H), 3.77 (s, 3H); MS (ESI+) m/z 296 (M+H).

Step B: Phosphorus oxychloride (7.74 ml, 84.6 mmol) was added slowly to ice-cold DMF (200 mL) and the resulting mixture was stirred at 0° C. for 1 h. To this mixture was added a solution of methyl 1-(4-methoxybenzyl)-1H-indole-4-carboxylate (16.6 g, 56.4 mmol) from Step A above in DMF (100 mL) and the mixture was stirred for 2 h. The reaction mixture was poured into an ice/water mixture and the pH was adjusted to 7 by adding 1 N NaOH. The compound was extracted with ethyl acetate (3×500 mL) and the combined organic layers were washed with water (4×250 mL) and brine (4×250 mL), dried ($Na_2SO_4$), filtered, and concentrated under reduced pressure. The crude material was purified by silica gel chromatography (ethyl acetate/hexanes: 20-40%) to afford methyl 3-formyl-1-(4-methoxybenzyl)-1H-indole-4-carboxylate (16.7 g, 93%) as an off-white solid: $^1$H NMR (500 MHz, $CDCl_3$) δ 10.48 (s, 1H), 7.99 (s, 1H), 7.85 (dd, J=10.0, 5.0 Hz, 1H), 7.55 (dd, J=10.0, 5.0 Hz, 1H), 7.30 (t, J=10.0 Hz, 1H), 7.12 (d, J=10.0 Hz, 2H), 6.86 (d, J=10.0 Hz, 2H), 5.31 (s, 2H), 3.99 (s, 3H), 3.71 (s, 3H); MS (ESI+) m/z 324 (M+H).

Step C: To a −78° C. cooled suspension of (methoxymethyl)triphenylphosphonium chloride (35.4 g, 103.3 mmol) in tetrahydrofuran (500 mL) was carefully added a solution of LiHMDS (1.0M in THF, 103.3 mL, 103.3 mmol. The resulting dark red mixture was stirred at −40° C. for 30 min. To this was added a solution of methyl 3-formyl-1-(4-methoxybenzyl)-1H-indole-4-carboxylate (16.7 g, 51.7 mmol) from Step B above in tetrahydrofuran slowly and the mixture was stirred for 1 h. The reaction was quenched with sat. aqueous sodium chloride (200 mL) and extracted with ethyl acetate (3×500 mL). The combined organic layers were washed with brine (2×750 mL), dried ($Na_2SO_4$), filtered, and concentrated in vacuo to afford a yellow oil (17.4 g, 96%). The oil was purified by column chromatography (silica gel, 5 to 30% ethyl acetate in hexanes) to afford a mixture of (E/Z)-methyl 3-(3-methoxyallyl)-1-(4-methoxybenzyl)-1H-indole-4-carboxylatemethyl (17.4 g, 96%) as a pale yellow oil. A mixture of tetrahydrofuran (500 mL) and 1N hydrochloric acid (100 mL) was added to the pale yellow oil (11.0 g, 31.3 mmol) and the resulting biphasic mixture was heated to reflux for 1 h. The mixture was cooled to room temperature and diluted with ethyl acetate (500 mL). The organic layer was separated and washed with brine (2×200 mL), dried ($Na_2SO_4$), filtered, and concentrated in vacuo. The crude material was purified by column chromatography (silica gel, ethyl acetate/hexanes: 10/90-40/60) to afford methyl 1-(4-methoxybenzyl)-3-(3-oxopropyl)-1H-indole-4-carboxylate (16.7 g, 93%) as an off-white solid: $^1$H NMR (500 MHz, $CDCl_3$) δ 9.82 (s, 1H), 7.77 (dd, J=10.0, 5.0 Hz, 1H), 7.47 (dd, J=10.0, 5.0 Hz, 1H), 7.19 (t, J=10.0 Hz, 1H), 7.12 (s, 1H), 7.05 (d, J=5.0 Hz, 2H), 6.84 (d, J=5.0 Hz, 2H), 5.25 (s, 2H), 4.00 (s, 2H), 3.90 (s, 3H): 3.77 (s, 3H); MS (ESI+) m/z 338 (M+H).

Step D: To a solution of quinuclidin-4-ylmethanamine dihydrochloride (433 mg, 2.0 mmol) in MeOH (20 mL) at room temperature was added sodium methoxide (25 wt % in MeOH, 0.9 mL, 4.1 mmol) dropwise. The reaction mixture was stirred at room temperature for 1 h and then glacial acetic acid (0.3 mL, 4.7 mmol) was added to neutralize the basicity of the mixture. Sodium cyanoborohydride (255 mg, 4.1 mmol) was added, followed by methyl 1-(4-methoxybenzyl)-3-(2-oxoethyl)-1H-indole-4-carboxylate (691 mg, 2.4 mmol) from Step C above in MeOH (25 mL). The mixture was stirred at room temperature until the reaction was complete by TLC (1-2 h). The reaction mixture was concentrated, absorbed onto silica gel, and purified by column chromatography (80:18:2 methylene chloride/methanol/concentrated ammonium hydroxide) to afford methyl 1-(4-methoxybenzyl)-3-(2-(quinuclidin-4-ylmethylamino)ethyl)-1H-indole-4-carboxylate as colourless oil (53%): $^1$H NMR (300 MHz, $CD_3OD$) δ 7.62 (d, J=8.1 Hz, 1H), 7.58 (d, J=7.5 Hz, 1H), 7.29 (s, 1H), 7.20-7.07 (m, 3H), 6.84 (d, J=6.0 Hz, 2H), 5.31 (s, 2H), 3.93 (s, 3H), 3.74 (s, 3H), 3.13 (t, J=7.2 Hz, 2H), 2.95 (t, J=7.8 Hz, 6H), 2.84 (t, J=7.2 Hz, 2H), 2.44 (s, 2H), 1.46 (t, J=7.8 Hz, 6H); MS (ESI+) m/z 462 (M+H).

Step E: A mixture of methyl 1-(4-methoxybenzyl)-3-(2-(quinuclidin-4-ylmethylamino)ethyl)-1H-indole-4-carboxylate (520 mg, 1.1 mmol) from Step D above and lithium hydroxide monohydrate (142 mg, 3.4 mmol) in tetrahydrofuran/water (30 mL, 1:1) was stirred at reflux until the reaction was complete by LC-MS. The solvent was removed under reduced pressure to give lithium 1-(4-methoxybenzyl)-3-(2-(quinuclidin-4-ylmethylamino)ethyl)-1H-indole-4-carboxylate as a white solid (878 mg, crude): $^1$H NMR (500 MHz, CD$_3$OD) δ 7.31 (d, J=8.0 Hz, 1H), 7.15 (d, J=7.0 Hz, 1H), 7.10-7.05 (m, 4H), 6.80 (d, J=8.5 Hz, 2H), 5.25 (s, 1H), 3.74 (s, 3H), 3.13 (t, J=7.0 Hz, 2H), 2.81 (t, J=7.0 Hz, 2H), 2.77 (t, J=7.5 Hz, 6H), 2.30 (s, 2H), 1.89 (s, 1H), 1.31 (t, J=7.5 Hz, 6H); MS (ESI+) m/z 448 (M+H).

Step F: Lithium 1-(4-methoxybenzyl)-3-(2-(quinuclidin-4-ylmethylamino)ethyl)-1H-indole-4-carboxylate (845 mg, 1.9 mmol) from Step E above in THF (30 mL) was cooled in an ice bath while N,N-diisopropylethylamine (1.8 mL, 11.2 mmol) was added, followed by 1-propanephosphonic acid cyclic anhydride (T$_3$P; 50 wt % in ethyl acetate; 7 mL, 11.2 mmol). The reaction mixture was stirred at room temperature until the reaction was complete by TLC (30 min-1 h). The mixture was concentrated and then purified with ISOLUTE® SCX-2 columns to give 6-(4-methoxybenzyl)-2-(quinuclidin-4-ylmethyl)-2,3,4,6-tetrahydro-1H-azepino[5,4,3-cd]indol-1-one as an off-white solid (418 mg, 52%): $^1$H NMR (300 MHz, CD$_3$OD) δ 7.72 (d, J=6.9 Hz, 1H), 7.52 (d, J=7.8 Hz, 1H), 7.26-7.15 (m, 2H), 7.11 (d, J=8.7 Hz, 2H), 6.83 (d, J=8.7 Hz, 2H), 5.29 (s, 2H), 3.90-3.72 (m, 7H), 3.06 (t, J=4.2 Hz, 2H), 2.90 (t, J=7.5 Hz, 6H), 1.62 (t, J=7.8 Hz, 6H); MS (ESI+) m/z 430 (M+H).

Step G: 6-(4-Methoxybenzyl)-2-(quinuclidin-4-ylmethyl)-2,3,4,6-tetrahydro-1H-azepino[5,4,3-cd]indol-1-one (~6 mg, 0.01 mmol) from Step F above was dissolved in 1.25 M HCl in CH$_3$OH and concentrated under reduced pressure to give 6-(4-methoxybenzyl)-2-(quinuclidin-4-ylmethyl)-2,3,4,6-tetrahydro-1H-azepino[5,4,3-cd]indol-1-one hydrochloride as a white solid (15 mg, 100%): $^1$H NMR (500 MHz, CD$_3$OD) δ 7.73 (d, J=7.5 Hz, 1H), 7.55 (d, J=8.5 Hz, 1H), 7.22 (t, J=8.0 Hz, 2H), 7.11 (d, J=8.5 Hz, 2H), 6.84 (d, J=7.5 Hz, 2H), 5.30 (s, 2H), 4.00-3.70 (m, 7H), 3.38 (t, J=8.0 Hz, 6H), 3.09 (t, J=4.5 Hz, 2H), 1.98 (t, J=8.0 Hz, 6H); MS (ESI+) m/z 430 (M+H).

Example 28

Preparation of 2-(quinuclidin-4-ylmethyl)-2,3,4,6-tetrahydro-1H-azepino[5,4,3-cd]indol-1-one hydrochloride

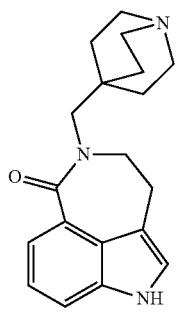 [SMILES: O=C1c2cccc3[nH]cc(c23)CCN1CC12CCN(CC1)CC2]

Step A: A solution of 6-(4-methoxybenzyl)-2-(quinuclidin-4-ylmethyl)-2,3,4,6-tetrahydro-1H-azepino[5,4,3-cd]indol-1-one (363 mg, 0.84 mmol) from Step G of Example 27 in anisole (12 mL) was added dropwise to a mixture of aluminum chloride (2.35 g, 17.61 mmol) in anisole (18 mL) at 0° C. The mixture was stirred in an icebath until the reaction was complete by TLC (~1 h). The reaction was quenched with sat. NaHCO$_3$ and the pH was adjusted to 7-8 with sat. NaHCO$_3$. The aqueous phase was extracted several times with methylene chloride. The combined organic layers were dried (Na$_2$SO$_4$), filtered, concentrated and purified by column chromatography (silica gel, 80:18:2 methylene chloride/methanol/concentrated ammonium hydroxide) to afford 2-(quinuclidin-4-ylmethyl)-2,3,4,6-tetrahydro-1H-azepino [5,4,3-cd]indol-1-one as a white solid (141 mg, 54%): $^1$H NMR (500 MHz, CD$_3$OD) δ 7.71 (d, J=7.5 Hz, 1H), 7.53 (d, J=8.5 Hz, 1H), 7.21 (t, J=8.0 Hz, 1H), 7.16 (s, 1H), 3.79 (broad s, 4H), 3.13-3.05 (m, 8H), 1.78 (t, J=8.0 Hz, 6H); MS (ESI+) m/z 310 (M+H).

Step B: 2-(Quinuclidin-4-ylmethyl)-2,3,4,6-tetrahydro-1H-azepino[5,4,3-cd]indol-1-one (141 mg, 0.45 mmol) from Step A above was dissolved in 1.25 M HCl in methanol and concentrated under reduced pressure to give 2-(quinuclidin-4-ylmethyl)-2,3,4,6-tetrahydro-1H-azepino[5,4,3-cd]indol-1-one hydrochloride as a white solid (56 mg, 36%): $^1$H NMR (300 MHz, CD$_3$OD) δ 7.72 (d, J=7.5 Hz, 1H), 7.54 (d, J=8.1 Hz, 1H), 7.21 (t, J=7.8 Hz, 1H), 7.18 (s, 1H), 3.81 (s, 4H), 3.38 (t, J=7.8 Hz, 6H), 3.11 (s, 2H), 1.99 (t, J=8.1 Hz, 6H); MS (ESI+) m/z 310 (M+H).

Example 29

Preparation of 4-(quinuclidin-4-ylmethyl)-3,4-dihydropyrazolo[3,4,5-de]isoquinolin-5(1H)-one, hydrochloride salt

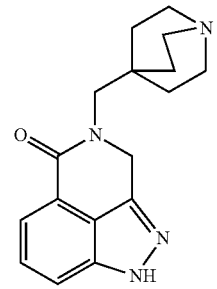 [SMILES: O=C1c2cccc3[nH]nc(c23)CN1CC12CCN(CC1)CC2]

Quinuclidin-4-ylmethanamine was synthesized from quinuclidine-4-carbonitrile according to a reported method (PCT Publication No. WO 99/021855, which is hereby incorporated by reference in its entirety).

Step A: To a stirred solution of quinuclidin-4-ylmethanamine (1.0 g, 7.14 mmol) in 1,4-dioxane (30 mL) was added methyl 3-formyl-1H-indazole-4-carboxylate (1.2 g, 6.0 mmol) in 1,4-dioxane (10 mL). Then glacial acetic acid (1% of total solvent used) was added and the reaction mixture was stirred at 60° C. for 2 h. It was cooled to room temperature and sodium triacetoxyborohydride (3.8 g, 17.9 mmol) was added. The reaction mixture was stirred at room temperature for 4 h). The solvent was removed under reduced pressure and the crude material was purified by column chromatography (silica gel, 70:27:3 dichloromethane/methanol/concentrated ammonium hydroxide) to give methyl 3-((quinuclidin-4-ylmethylamino)methyl)-1H-indazole-4-carboxylate as a brown oil (2.1 g, quantitative yield): $^1$H NMR (500 MHz, CD$_3$OD) δ 7.87 (d, J=8.0 Hz, 1H), 7.81 (d, J=8.0 Hz, 1H), 7.49 (t, J=8.0 Hz, 1H), 4.38 (s, 2H), 3.99 (s, 3H), 3.27 (t, J=8.0 Hz, 6H), 2.68 (s, 2H), 1.78 (t, J=8.0 Hz, 6H); MS (ESI+) m/z 329 (M+H).

Step B: A mixture of methyl 3-((quinuclidin-4-ylmethylamino)methyl)-1H-indazole-4-carboxylate (2.9 g, 8.9 mmol) from Step A above and lithium hydroxide monohydrate (1.1 g, 26.7 mmol) in tetrahydrofuran/water (1:1, 30 mL) was stirred at reflux until the reaction was complete by LC-MS. The solvent was removed under reduced pressure to give lithium 3-((quinuclidin-4-ylmethylamino)methyl)-1H-indazole-4-carboxylate as a brown solid (3.9 g, quantitative yield): $^1$H NMR (500 MHz, CD$_3$OD) δ 7.49 (d, J=8.5 Hz, 1H), 7.43 (d, J=7.0 Hz, 1H), 7.35 (t, J=8.0 Hz, 1H), 4.17 (s, 2H), 2.82 (t, J=8.0 Hz, 6H), 2.26 (s, 2H), 1.42 (t, J=8.0 Hz, 6H); MS (ESI+) m/z 315 (M+H).

Step C: Lithium 3-((quinuclidin-4-ylmethylamino)methyl)-1H-indazole-4-carboxylate (3.9 g, 12.1 mmol) from Step B above in THF (20 mL) was cooled in an ice bath while N,N-diisopropylethylamine (9.4 g, 72.8 mmol) was added, followed by 1-propanephosphonic acid cyclic anhydride (T3P) (23.0 g, 72.8 mmol). The reaction mixture was stirred at room temperature for 5 h and then concentrated under reduced pressure. The crude material was purified by column chromatography (silica gel, 60:36:4 dichloromethane/methanol/concentrated ammonium hydroxide) to give 4-(quinuclidin-4-ylmethyl)-3,4-dihydropyrazolo[3,4,5-de]isoquinolin-5(1H)-one as a yellow oil (468 mg, 13%): $^1$H NMR (500 MHz, CD$_3$OD) δ 7.62-7.60 (m, 1H), 7.54-7.53, (m, 2H), 5.15 (s, 2H), 3.53 (s, 2H), 2.93 (t, J=8.0 Hz, 6H), 1.67 (t, J=8.0 Hz, 6H); MS (ESI+) m/z 297 (M+H).

Step D: 4-(Quinuclidin-4-ylmethyl)-3,4-dihydropyrazolo[3,4,5-de]isoquinolin-5(1H)-one (468 mg, 1.58 mmol) from Step C above was dissolved in HCl (1.25 M in methanol) and concentrated under reduced pressure to give 4-(quinuclidin-4-ylmethyl)-3,4-dihydropyrazolo[3,4,5-de]isoquinolin-5(1H)-one hydrochloride as an off-white solid (305 mg, 58%): $^1$H NMR (500 MHz, CD$_3$OD) δ 7.63-7.61 (m, 1H), 7.55-7.53 (m, 2H), 5.15 (s, 2H), 3.58 (s, 2H), 3.08 (t, J=8.0 Hz, 6H), 1.78 (t, J=8.0 Hz, 6H); MS (ESI+) m/z 297 (M+H).

Examples 30 and 31

Preparation of 7-(quinuclidin-3-ylmethyl)-7,8-dihydropyrazolo[3,4,5-de]isoquinolin-6(2H)-one, enantiomers A and B, hydrochloride salts

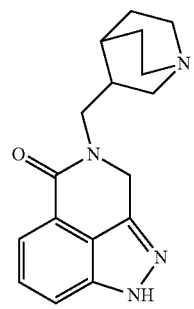 [SMILES: O=C1c2cccc3[nH]nc(c23)CN1CC1CN2CCC1CC2]

Quinuclidin-3-ylmethanamine was synthesized from quinuclidine-3-carbonitrile according to a reported method (U.S. Pat. No. 4,853,376, which is hereby incorporated by reference in its entirety).

Step A: The procedure described in Step A of Example 29 was used to convert methyl 3-formyl-1H-indazole-4-carboxylate and quinuclidin-3-ylmethanamine to methyl 3-((quinuclidin-3-ylmethylamino)methyl)-1H-indazole-4-carboxylate: $^1$H NMR (500 MHz, CD$_3$OD) δ 7.90 (dd, J=7.3, 0.7 Hz, 1H), 7.81 (dd, J=8.4, 0.7 Hz, 1H), 7.49 (dd, J=8.4, 7.3 Hz, 1H), 4.45 (d, J=3.0 Hz, 2H), 3.99 (s, 3H), 3.41-3.30 (m, 2H), 3.23-3.12 (m, 4H), 2.96 (dd, J=12.3, 7.7 Hz, 1H), 2.90 (dd, J=12.3, 7.7 Hz, 1H), 2.82-2.78 (m, 1H), 2.29-2.25 (m, 1H), 2.06-2.03 (m, 1H), 1.96-1.90 (m, 1H), 1.89-1.85 (m, 1H), 1.77-1.70 (m, 1H); MS (ESI+) m/z 329 (M+H).

Step B: The procedure described in Step B of Example 29 was used to convert methyl 3-((quinuclidin-3-ylmethylamino)methyl)-1H-indazole-4-carboxylate from Step A above to lithium 3-((quinuclidin-3-ylmethylamino)methyl)-1H-indazole-4-carboxylate: MS (ESI+) m/z 315 (M+H).

Step C: The procedure described in Step C of Example 29 was used to convert lithium 3-((quinuclidin-3-ylmethylamino)methyl)-1H-indazole-4-carboxylate from Step B above to 7-(quinuclidin-3-ylmethyl)-7,8-dihydropyrazolo[3,4,5-de]isoquinolin-6(2H)-one: MS (ESI+) m/z 297 (M+H).

Step D: 7-(Quinuclidin-3-ylmethyl)-7,8-dihydropyrazolo[3,4,5-de]isoquinolin-6(2H)-one from Step C above was resolved by preparative chiral HPLC (CHIRALCEL OD column, using 80:20:0.1 heptane/isopropanol/diethylamine as the eluent) to give enantiomers A and B.

Step E: The procedure described in Step D of Example 29 was used to convert 7-(quinuclidin-3-ylmethyl)-7,8-dihydropyrazolo[3,4,5-de]isoquinolin-6(2H)-one, enantiomer A (absolute stereochemistry unknown) from Step D above to the corresponding hydrochloride salt: $^1$H NMR (500 MHz, CD$_3$OD) δ 7.65-7.63 (m, 1H), 7.57-7.53 (m, 2H), 5.16 (s, 2H), 3.92 (dd, J=14.0, 8.2 Hz, 1H), 3.87 (dd, J=14.0, 7.4 Hz, 1H), 3.55-3.50 (m, 1H), 3.47-3.41 (m, 1H), 3.39-3.24 (m, 3H), 3.13-3.09 (m, 1H), 2.75-2.70 (m, 1H), 2.44-2.38 (m, 1H), 2.07 (bs, 1H), 2.03-1.88 (m, 3H); MS (ESI+) m/z 297 (M+H).

Step F: The procedure described in Step D of Example 29 was used to convert 7-(quinuclidin-3-ylmethyl)-7,8-dihydropyrazolo[3,4,5-de]isoquinolin-6(2H)-one, enantiomer B (absolute stereochemistry unknown) from Step D above to the corresponding hydrochloride salt: $^1$H NMR (500 MHz, CD$_3$OD) δ 7.65-7.63 (m, 1H), 7.57-7.53 (m, 2H), 5.16 (s, 2H), 3.92 (dd, J=14.0, 8.2 Hz, 1H), 3.87 (dd, J=14.0, 7.4 Hz, 1H), 3.55-3.50 (m, 1H), 3.47-3.41 (m, 1H), 3.39-3.24 (m, 3H), 3.13-3.09 (m, 1H), 2.75-2.70 (m, 1H), 2.44-2.38 (m, 1H), 2.07 (bs, 1H), 2.03-1.88 (m, 3H); MS (ESI+) m/z 297 (M+H).

Example 32

Preparation of 7-(quinuclidin-4-ylmethyl)-8,9-dihydro-[1,4]diazepino[6,7,1-hi]indazol-6(7H)-one hydrochloride

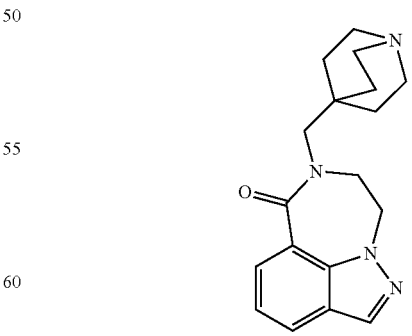

Step A: To a solution of 2-fluoro-3-methylbenzoic acid (12.4 g, 80.2 mmol) in methanol (100 mL) at 0° C. was added thionyl chloride (14 g, 120.3 mmol) dropwise. The reaction mixture was stirred at reflux until complete by TLC (1-2 h).

After cooling to room temperature, the mixture was partitioned between sat. NaHCO₃ and ethyl acetate. The combined organic layers were dried (Na₂SO₄), filtered and concentrated to give methyl 2-fluoro-3-methylbenzoate as a yellow oil (13.8 g, 100%): $^1$H NMR (300 MHz, CDCl₃) δ 7.74 (t, J=8.1 Hz, 1H), 7.37 (t, J=7.8 Hz, 1H), 7.08 (t, J=7.5 Hz, 1H), 3.90 (s, 3H), 2.31 (s, 3H).

Step B: To a solution of methyl 2-fluoro-3-methylbenzoate (13.8 g, 82.3 mmol) from Step A above and N-bromosuccinimide (16.0 g, 90.6 mmol) in carbon tetrachloride (82 mL) at room temperature was added a catalytic amount of benzoyl peroxide. The yellow mixture was heated under reflux until the reaction was complete by TLC (overnight) and then it was concentrated and purified by column chromatography (silica gel, 9:1 hexanes/ethyl acetate) to afford methyl 3-(bromomethyl)-2-fluorobenzoate as a light yellow oil (11.5 g, 56%): $^1$H NMR (500 MHz, CDCl₃) δ 7.90 (t, J=8.0 Hz, 1H), 7.59 (t, J=7.5 Hz, 1H), 7.19 (t, J=7.5 Hz, 1H), 4.53 (s, 2H), 3.90 (s, 3H).

Step C: A mixture of methyl 3-(bromomethyl)-2-fluorobenzoate (11.5 g, 46.4 mmol) from Step B above and solid sodium bicarbonate (33.0 g, 398.7 mmol) in DMSO (150 mL) was refluxed until the reaction was complete by TLC (2-3 h). The mixture was cooled in an ice bath immediately and then partitioned between brine and ethyl acetate. The combined organics were concentrated and purified by column chromatography (silica gel, 9:1 hexanes/ethyl acetate) to afford methyl 2-fluoro-3-formylbenzoate as a white solid (5.44 g, 64%): $^1$H NMR (300 MHz, CDCl₃) δ 10.43 (s, 1H), 8.21 (t, J=7.8 Hz, 1H), 8.07 (t, J=6.0 Hz, 1H), 7.35 (t, J=7.8 Hz, 1H), 3.93 (s, 3H).

Step D: A mixture of methyl 2-fluoro-3-formylbenzoate (3.6 g, 19.9 mmol) from Step C above and hydroxy ethyl hydrazine (1.5 g, 19.9 mmol) in MeOH (16 mL) was irradiated with microwaves at 150° C. for 1.5 h. The reaction mixture was cooled and partitioned between H₂O and ethyl acetate. The aqueous phase was extracted with additional ethyl acetate and then the combined organic extracts were dried (Na₂SO₄) filtered, concentrated and purified by column chromatography (silica gel, 70:30 hexanes/ethyl acetate) to afford methyl 1-(2-hydroxyethyl)-1H-indazole-7-carboxylate as a yellow solid (2.83 g, 65%): $^1$H NMR (500 MHz, CDCl₃) δ 8.13 (s, 1H), 7.99 (d, J=7.5 Hz, 1H), 7.94 (d, J=8.0 Hz, 1H); 7.18 (t, J=8.5 Hz, 1H), 4.84 (t, J=5.0 Hz, 2H), 4.13-4.07 (m, 2H), 3.99 (s, 3H), 3.20-3.10 (m, 1H).

Step E: Oxalyl chloride (1.3 mL, 15.5 mmol) was added dropwise to a mixture of dimethyl sulfoxide (1.8 mL, 25.8 mmol) and methylene chloride (4 mL) at −78° C. After addition was complete, the mixture was stirred at −78° C. for 30 min. A solution of methyl 1-(2-hydroxyethyl)-1H-indazole-7-carboxylate (2.8 g, 12.9 mmol) from Step D above in methylene chloride (40 mL) and added dropwise while maintaining the temperature at −78° C. The reaction was then stirred at −78° C. for 1-2 h. The reaction was quenched with N,N-diisopropylethylamine, cooled to 0° C., and sat. NaHCO₃ was added. The aqueous phase was extracted several times with methylene chloride and the combined organic layers were dried (Na₂SO₄), filtered and concentrated to give methyl 1-(2-oxoethyl)-1H-indazole-7-carboxylate as a yellow oil (3.8 g, crude): $^1$H NMR (300 MHz, CDCl₃) δ 9.79 (s, 1H), 8.16 (s, 1H), 8.14-8.08 (m, 2H), 7.98 (d, J=7.5 Hz, 1H), 5.61 (s, 2H), 3.99 (s, 3H); MS (ESI+) m/z 219 (M+H).

Step F: To a stirred solution of quinuclidin-4-ylmethanamine dihydrochloride (894 mg, 4.2 mmol) in methanol (12 mL) at room temperature was added sodium methoxide (25 wt % in MeOH, 1.8 mL, 8.4 mmol) dropwise. The reaction was stirred at room temperature for 1 h and then glacial acetic acid (0.6 mL, 9.7 mmol) was added to neutralize the basicity of the mixture. Sodium cyanoborohydride (528 mg, 8.4 mmol) was added, followed by a solution of methyl 1-(2-oxoethyl)-1H-indazole-7-carboxylate (920 mg, 4.2 mmol) from Step E above in methanol (10 mL). The mixture was stirred at room temperature until the reaction was complete by TLC (1-2 h). The reaction mixture was concentrated, absorbed onto silica gel, and purified by column chromatography (80:18:2 methylene chloride/methanol/concentrated ammonium hydroxide) to afford methyl 1-(2-(quinuclidin-4-ylmethylamino)ethyl)-1H-indazole-7-carboxylate as a yellow oil (563 mg, 39%): $^1$H NMR (300 MHz, CD₃OD) δ 8.26 (s, 1H), 8.09-8.03 (m, 2H), 7.27 (t, J=7.2 Hz, 1H), 4.95 (t, J=5.7 Hz, 2H), 4.01 (s, 3H), 3.50-3.44 (m, 2H), 3.39 (t, J=7.8 Hz, 6H), 2.93 (s, 2H), 1.85 (t, J=8.1 Hz, 6H).

Step G: A mixture of methyl 1-(2-(quinuclidin-4-ylmethylamino)ethyl)-1H-indazole-7-carboxylate (563 mg, 1.7 mmol) from Step F above and lithium hydroxide monohydrate (207 mg, 4.9 mmol) in tetrahydrofuran/water (16 mL; 1:1) was stirred at reflux until the reaction was complete by TLC and/or LC-MS. The solvent was removed under reduced pressure to give lithium 1-(2-(quinuclidin-4-ylmethylamino)ethyl)-1H-indazole-7-carboxylate (1.20 g, crude): $^1$H NMR (300 MHz, CD₃OD) δ 8.03 (s, 1H), 7.72 (d, J=8.1 Hz, 1H), 7.55 (d, J=7.2 Hz, 1H), 7.11 (t, J=7.4 Hz, 1H), 3.28-3.20 (m, 2H); 2.98 (t, J=6.6 Hz, 2H), 2.81 (t, J=7.5 Hz, 6H), 2.28 (s, 2H), 1.36 (t, J=8.1 Hz, 6H).

Step H: Lithium 1-(2-(quinuclidin-4-ylmethylamino)ethyl)-1H-indazole-7-carboxylate (1.2 g, 3.6 mmol) from Step G above in THF (30 mL) was cooled in an ice bath while N,N-diisopropylethylamine (4 mL, 21.6 mmol) was added, followed by 1-propanephosphonic acid cyclic anhydride (T₃P; 50 wt % in EtOAc; 14 mL, 21.6 mmol). The reaction mixture was stirred at room temperature until the reaction was complete by TLC (overnight). The mixture was concentrated in vacuo and then purified with ISOLUTE® SCX-2 columns to give 7-(quinuclidin-4-ylmethyl)-8,9-dihydro-[1,4]diazepino[6,7,1-hi]indazol-6(7H)-one (267 mg, 24%).

Step I: 7-(Quinuclidin-4-ylmethyl)-8,9-dihydro-[1,4]diazepino[6,7,1-hi]indazol-6(7H)-one (267 mg, 0.9 mmol) from Step H above was dissolved in 1.25 M HCl in methanol and concentrated under reduced pressure to give 7-(quinuclidin-4-ylmethyl)-8,9-dihydro-[1,4]diazepino[6,7,1-hi]indazol-6(7H)-one hydrochloride as an off-white solid (299 mg, 100%): $^1$H NMR (500 MHz, D₂O) δ 8.04 (s, 1H), 7.92 (d, J=7.0 Hz, 2H), 7.21 (t, J=8.0 Hz, 1H), 4.54 (s, 2H), 3.86 (s, 2H), 3.55 (s, 2H), 3.23 (t, J=7.5 Hz, 6H), 1.83 (t, J=7.5 Hz, 6H); MS (ESI+) m/z 311 (M+H).

Examples 33 and 34

Preparation of 7-(quinuclidin-3-ylmethyl)-7,8-dihydropyrazolo[3,4,5-de]isoquinolin-6(2H)-one, enantiomers A and B, hydrochloride salts

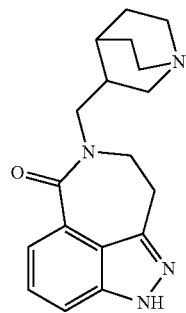 [SMILES: O=C1c2cccc3[nH]nc(c23)CCN1CC1CN2CCC1CC2]

Quinuclidin-3-ylmethanamine was synthesized from quinuclidine-3-carbonitrile according to a reported method (U.S. Pat. No. 4,853,376, which is hereby incorporated by reference in its entirety).

Step A: To a solution of methyl 3-formyl-1H-indazole-4-carboxylate (49.5 g, 242 mmol) was added cesium carbonate (158 g, 485 mmol) in DMF (750 mL) at 0° C. The mixture was stirred under an atmosphere of nitrogen for 15 min. To this solution were added 4-methoxybenzyl bromide (41.6 g, 267 mmol) and sodium iodide (7.3 g, 48.5 mmol). The resulting mixture continued to stir for 10 min and then warmed to room temperature and stirred for 2.5 h. The mixture was filtered to remove solid cesium carbonate and the filtrate was quenched with sat. aqueous sodium chloride (200 mL) and extracted with diethyl ether (3×500 mL). The combined organic layers were washed with brine (3×200 mL), dried (Na$_2$SO$_4$), filtered, and concentrated under reduced pressure. The crude material was purified by column chromatography (silica gel, 10 to 25% ethyl acetate in hexanes) to afford methyl 3-formyl-1-(4-methoxybenzyl)-1H-indazole-4-carboxylate (41.8 g, 53%): $^1$H NMR δ (300 MHz, CDCl$_3$) 10.53 (s, 1H), 7.77 (dd, J=7.2, 1.0 Hz, 1H), 7.58 (d, J=9.0, 1.0 Hz, 1H), 7.44 (dd, J=9.0, 7.20, Hz, 1H), 7.20 (dd, J=6.6, 2.1 Hz, 2H), 6.89 (dd, J=6.9, 2.1 Hz, 2H), 5.68 (s, 2H), 4.01 (s, 3H), 3.77 (s, 3H); MS (ESI+) m/z 325 (M+H). In addition, methyl 3-formyl-2-(4-methoxybenzyl)-2H-indazole-4-carboxylate (24.2 g, 31%) was also isolated: $^1$H NMR δ (300 MHz, CDCl$_3$) 10.88 (s, 1H), 8.10 (t, J=7.2 Hz, 2H), 7.42 (dd, J=9.0, 1.0 Hz, 1H), 7.36 (dd, J=9.0, 7.20, Hz, 1H), 6.82 (dd, J=6.6, 2.1 Hz, 2H), 6.07 (s, 2H), 4.01 (s, 3H), 3.77 (s, 3H); MS (ESI+) m/z 325 (M+H).

To a −78° C. cooled suspension of (methoxymethyl)triphenylphosphonium chloride (119 g, 347 mmol) in tetrahydrofuran (1000 mL) was carefully added a solution of lithium bis(trimethylsilyl)amide (1.0M in THF, 347 mL, 347 mmol). The resulting dark red mixture was stirred at −40° C. for 30 min. To this was added a solution of methyl 3-formyl-1-(4-methoxybenzyl)-1H-indazole-4-carboxylate (45 g, 139 mmol) in tetrahydrofuran slowly and the mixture was stirred for 30 min. The reaction was quenched with sat. aqueous sodium chloride (500 mL) and extracted with ethyl acetate (3×500 mL). The combined organic layers were washed with brine (4×300 mL), dried (Na$_2$SO$_4$), filtered, and concentrated under reduced pressure. The crude oil was purified by column chromatography (silica gel, 5 to 30% ethyl acetate in hexanes) to afford methyl 1-(4-methoxybenzyl)-3-(2-methoxyvinyl)-1H-indazole-4-carboxylate (40.3 g, 82%) as a yellow oil. A mixture of tetrahydrofuran (950 mL) and 6N hydrochloric acid (30 mL) was added to methyl 1-(4-methoxybenzyl)-3-(2-methoxyvinyl)-1H-indazole-4-carboxylate (40.3 g, 114.5 mmol) and the resulting biphasic mixture was heated to reflux for 2.5 h. The mixture was cooled to room temperature and diluted with ethyl acetate (1500 mL). The organic layer was separated and washed with brine (4×500 mL), dried (Na$_2$SO$_4$), filtered, and concentrated under reduced pressure to afford methyl 1-(4-methoxybenzyl)-3-(2-oxoethyl)-1H-indazole-4-carboxylate (30 g, 77%) as a yellow solid: $^1$H NMR δ (300 MHz, DMSO-d$_3$) 9.78 (s, 1H), 8.04 (d, J=8.0 Hz, 1H), 7.49 (dd, J=7.2, 0.6 Hz, 1H), 7.48 (dd, J=8.7, 7.5 Hz, 1H), 7.22-7.19 (m, 2H), 6.88-6.85 (m, 2H), 5.61 (s, 2H), 4.26 (s, 2H), 3.84 (s, 3H), 3.69 (s, 3H); MS (ESI+) m/z 339 (M+H).

Step C: The procedure described in Step A of Example 29 was used to convert methyl 1-(4-methoxybenzyl)-3-(2-oxoethyl)-1H-indazole-4-carboxylate from Step B above and quinuclidin-3-ylmethanamine to methyl 1-(4-methoxybenzyl)-3-(2-(quinuclidin-3-ylmethylamino)ethyl)-1H-indazole-4-carboxylate: $^1$H NMR (500 MHz, CD$_3$OD) δ 7.78 (dd, J=8.5, 0.7 Hz, 1H), 7.74 (dd, J=7.2, 0.7 Hz, 1H), 7.43 (dd, J=8.5, 7.3 Hz, 1H), 7.13 (d, J=8.8 Hz, 2H), 6.84 (d, J=8.8 Hz, 2H), 5.55 (s, 2H), 3.97 (s, 3H), 3.74 (s, 3H), 3.41 (t, J=7.1 Hz, 2H), 3.32-3.29 (m, 1H), 3.09-3.05 (m, 2H), 2.97-2.85 (m, 4H), 2.77 (dd, J=12.0, 8.1 Hz, 1H), 2.67 (dd, J=12.0, 7.1 Hz, 1H), 2.47-2.42 (m, 1H), 1.96-1.90 (m, 1H), 1.76-1.70 (m, 3H), 1.65-1.60 (m, 1H), 1.51-1.44 (m, 1H); MS (ESI+) m/z 463 (M+H).

Step D: The procedure described in Step B of Example 29 was used to convert methyl 1-(4-methoxybenzyl)-3-(2-(quinuclidin-3-ylmethylamino)ethyl)-1H-indazole-4-carboxylate from Step C above to lithium 1-(4-methoxybenzyl)-3-(2-(quinuclidin-3-ylmethylamino)ethyl)-1H-indazole-4-carboxylate: MS (ESI+) m/z 449 (M+H).

Step E: The procedure described in Step C of Example 29 was used to convert lithium 1-(4-methoxybenzyl)-3-(2-(quinuclidin-3-ylmethylamino)ethyl)-1H-indazole-4-carboxylate from Step D above to 2-(4-methoxybenzyl)-7-(quinuclidin-3-ylmethyl)-8,9-dihydro-2H-azepino[5,4,3-cd]indazol-6(7H)-one: $^1$H NMR (500 MHz, CD$_3$OD) δ 7.84 (d, J=7.2 Hz, 1H), 7.72 (d, J=8.3 Hz, 1H), 7.51 (dd, J=8.4, 7.3 Hz, 1H), 7.18 (d, J=8.8 Hz, 2H), 6.84 (d, J=8.7 Hz, 2H), 5.54 (s, 2H), 3.91-3.87 (m, 3H), 3.75-3.71 (m, 1H), 3.74 (s, 3H), 3.23-3.20 (m, 2H), 3.18-3.15 (m, 1H), 3.07-2.91 (m, 4H), 2.69-2.64 (m, 1H), 2.39-2.33 (m, 1H), 2.16-2.08 (m, 1H), 1.83-1.77 (m, 2H), 1.75-1.69 (m, 1H), 1.64-1.57 (m, 1H); MS (ESI+) m/z 431 (M+H).

Step F: A solution of 2-(4-methoxybenzyl)-7-(quinuclidin-3-ylmethyl)-8,9-dihydro-2H-azepino[5,4,3-cd]indazol-6(7H)-one (219 mg, 0.51 mmol) in trifluoroacetic acid (3 mL) was subjected to microwave irradiation at 130° C. for 18 min. The mixture was diluted with methanol and concentrated in vacuo. The resulting residue was converted to the free base by elution through an SCX-2 cartridge and then purified by column chromatography (silica gel, (12%-100% solvent mixture B in methylene chloride; solvent mixture B=70:27:3 methylene chloride/methanol/concentrated ammonium hydroxide) to afford 7-(quinuclidin-3-ylmethyl)-8,9-dihydro-2H-azepino[5,4,3-cd]indazol-6(7H)-one (140 mg, 88%) as a colorless oil: MS (ESI+) m/z 311 (M+H).

Step G: 7-(quinuclidin-3-ylmethyl)-8,9-dihydro-2H-azepino[5,4,3-cd]indazol-6(7H)-one from Step F above was resolved by preparative chiral HPLC (CHIRALCEL OD column, using 80:20:0.1 heptane/isopropanol/diethylamine as the eluent) to give enantiomers A and B.

Step H: The procedure described in Step D of Example 29 was used to convert 7-(quinuclidin-3-ylmethyl)-8,9-dihydro-2H-azepino[5,4,3-cd]indazol-6(7H)-one, enantiomer A (absolute stereochemistry unknown) from Step G above to the corresponding hydrochloride salt: $^1$H NMR (500 MHz, CD$_3$OD) δ 7.86 (d, J=7.3 Hz, 1H), 7.71 (d, J=8.3 Hz, 1H), 7.54 (dd, J=8.3, 7.3 Hz, 1H), 3.94-3.88 (m, 4H), 3.56-3.51 (m, 1H), 3.45-3.29 (m, 5H), 3.26-3.23 (m, 2H), 2.69-2.62 (m, 1H), 2.36 (br s, 1H), 2.10 (br s, 1H), 2.06-1.98 (m, 2H), 1.94-1.88 (m, 1H); MS (ESI+) m/z 311 (M+H).

Step I: The procedure described in Step D of Example 29 was used to convert 7-(quinuclidin-3-ylmethyl)-8,9-dihydro-2H-azepino[5,4,3-cd]indazol-6(7H)-one, enantiomer B (absolute stereochemistry unknown) from Step G above to the corresponding hydrochloride salt: $^1$H NMR (500 MHz, CD$_3$OD) δ 7.86 (d, J=7.3 Hz, 1H), 7.71 (d, J=8.3 Hz, 1H), 7.54 (dd, J=8.3, 7.3 Hz, 1H), 3.94-3.88 (m, 4H), 3.56-3.51 (m, 1H), 3.45-3.29 (m, 5H), 3.26-3.23 (m, 2H), 2.69-2.62 (m, 1H), 2.36 (br s, 1H), 2.10 (br s, 1H), 2.06-1.98 (m, 2H), 1.94-1.88 (m, 1H); MS (ESI+) m/z 311 (M+H).

Example 35

Compound Affinity for the Human 5-HT$_3$ Receptor

The relative affinity of the various compounds for the human 5-HT$_3$ receptor was measured in a radioligand binding assay, using a scintillation proximity assay (SPA) format. Test compounds were dissolved to 10 mM in 100% DMSO, then serially diluted at 10× assay concentrations in 100% DMSO in 96-well polypropylene plates and further diluted to 4× assay concentrations with the assay buffer. Samples were incubated in 50 mM Tris-HCl, pH 7.5, 3 mM MgCl$_2$, 1 mM EDTA and 10% DMSO with 10 nM [9-methyl-$^3$H]BRL-43694 (Perkin Elmer), 3 μg of human 5-HT$_3$ receptor membranes (Perkin Elmer) and 0.5 mg/mL SPA beads (WGA PVT, Amersham Biosciences) in a final volume of 0.2 mL. Binding reactions were set up in wells of PicoPlates-96 (Perkin Elmer) by adding consecutively 50 μL of each competing compound or buffer, SPA beads, the radioligand and 5-HT$_3$ receptor membranes. After an overnight incubation at room temperature on a Nutator mixer, plates were centrifuged for 15 min at 1,500 rpm, followed by incubation in the dark for 30 min. Radioactivity was counted in the TopCount microplate counter (Perkin Elmer) for 5 min. Total binding control contained compound dilution buffer only; nonspecific binding was determined in the presence of 30 μM MDL-72222. Specific binding was determined by subtracting nonspecific binding from total binding. All experiments were performed in duplicate using ten concentrations of competing ligand, with ondansetron included as a control in every run. IC$_{50}$ values were determined from specific binding data using XLfit4.1 curve fitting software from IDBS Ltd. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor.

Example 36

Agonist Activity at Recombinant Human 5-HT$_{3A}$ Receptors

Human embryonic kidney (HEK293) cells expressing the h5-HT$_{3A}$ receptor subunit were seeded directly into poly-D-lysine coated, black-walled, clear bottomed, 96 well plates with approximately 1×10$^5$ cells per well. After 48 hrs incubation in DMEM growth media (100 μL), cells were washed twice (each 200 μL) in Hank's balanced salt solution (Invitrogen) before incubation (1 hr) with Fluo-4 acetoxymethyl (AM) ester (100 μL, 2.5 μM; Molecular Probes). Cells were washed twice (each 200 μL) in Hank's balanced salt solution and incubated for a further 30 min in Hank's balanced salt solution (100 μL) prior to assay (25° C.). Alteration in [Ca$^{2+}$]$_i$ was measured (relative fluorescence units [RFU]) using a Flexstation (excitation 488 nm and emission 515 nm; frequency of recording 3 sec). After recording for at least 80 sec, vehicle (Hank's balanced salt solution) or drug was automatically administered to the well (50 μL). Baseline was calculated from the 5 data points immediately prior to the first drug administration and the maximum response was that achieved over the 240 sec following drug administration. In all experiments the muscarinic receptor agonist carbachol (1 mM) was added 240 sec after the test drug administration. Muscarinic receptors are endogenously expressed by HEK293 cells; in every experiment, carbachol elicited a response comparable to the maximum response elicited by the maximal effective concentration of 5-HT.

Example 37

Von Bezold-Jarisch Model In Vivo

5-HT$_3$ receptor modulators have proven efficacy in the treatment of human GI disorders as demonstrated by the approval of alosetron and ramosetron for IBS-D. In vivo activity at 5-HT$_3$ receptors can be assessed using the 5-HT$_3$ mediated transient bradycardia observed after the intravenous administration of 5-HT or 5-HT$_3$ selective agonists in anesthetized mice (von Bezold-Jarisch reflex). This is a well characterized and widely used model to assess 5-HT$_3$ receptor function in vivo (King et al., 5-*Hydroxtryptamine*-3 *Receptor Antagonists*, CRC Press, pp. 74-75 (1993), which is hereby incorporated by reference in its entirety). Certain compounds (Table 1) were evaluated for their ability to inhibit serotonin induced bradycardia in vivo in the mouse (Saxena et al., *Arch. Int. Pharmacodyn.*, 277:235-252 (1985), which is hereby incorporated by reference in its entirety). Test substances and vehicle [2% Tween 80] were each administered orally to a group of 5 male ICR mice each weighing 24±2 g. A dosing volume of 10 mL/kg was used. Sixty minutes later, 5-HT (0.1 mg/kg IV)-induced bradycardia was recorded in urethane (2250 mg/kg IP, given 10 minutes before 5-HT)-anesthetized animals. The highest oral dose tested is reported in Table 1.

TABLE I

Biological Activity of Exemplified Compounds

| Example Number | h5-HT$_{3A}$ K$_i$ (nM) | HEK293 h5-HT$_{3A}$* | Inhibition of 5-HT Induced Bradycardia in Mice |
|---|---|---|---|
| 1 | 74 | | |
| 2 | 4 | 7 | |
| 3 | 5 | 13 | |
| 4 | 0.2 | | |
| 5 | 416 | | |
| 6 | 205 | | |
| 7 | 8 | 19 | 77% @ 3 mg/kg |
| 8 | 0.5 | | |
| 9 | 6 | | |

TABLE I-continued

Biological Activity of Exemplified Compounds

| Example Number | h5-HT$_{3A}$ K$_i$ (nM) | HEK293 h5-HT$_{3A}$* | Inhibition of 5-HT Induced Bradycardia in Mice |
|---|---|---|---|
| 10 | 14 | | |
| 11 | 0.8 | | |
| 12 | 2 | | |
| 13 | 32 | | |
| 14 | 40% inhibition @ 10 μM | | |
| 15 | 80% inhibition @ 10 μM | | |
| 16 | 39% inhibition @ 10 μM | | |
| 17 | 130 | | |
| 18 | 51% inhibition @ 10 μM | | |
| 19 | 74% inhibition @ 10 μM | | |
| 20 | 23% inhibition @ 10 μM | | |
| 21 | 406 | | |
| 22 | 69% inhibition @ 10 μM | | |
| 23 | 206 | | |
| 24 | 75% inhibition @ 10 μM | | |
| 25 | 7 | 83 | |
| 26 | 701 | | |
| 27 | 8 | | |
| 28 | 30 | | |
| 29 | 2 | 1 | 87% @ 3 mg/kg |
| 30 (Enant. A) | 217 | | |
| 31 (Enant. B) | 24 | | |
| 32 | 73 | | |
| 33 (Enant. A) | 579 | | |
| 34 (Enant. B) | 241 | | |
| Alosetron | 0.5 | NR | |
| Ramosetron | 0.06 | NR | |

*% agonist response at 1 μM is normalized to the response of 5-HT (5-HT response = 100% at 3 μM); NR = no response The present invention is not limited to the compounds found in the above examples, and many other compounds falling within the scope of the invention may also be prepared using the procedures set forth in the above synthetic schemes. The preparation of additional compounds of formula I or II using these methods will be apparent to one of ordinary skill in the chemical arts.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula I:

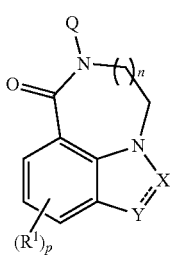

formula I wherein:
------ represents an optional double bond;
Q is a saturated, bicyclic, heterocyclic amine comprising at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —OR$^7$, and —NR$^7$R$^8$;

X is CH, CH$_2$, CR$^2$, C(R$^2$)$_2$, N, NH, C=O, or SO$_2$;
Y is CH, CH$_2$, CR$^2$, C(R$^2$)$_2$, N, NH, NR$^3$, O, or C=O;
R$^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R$^2$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R$^3$ is selected from the group consisting of H, $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R$^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R$^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R$^4$ and R$^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)$R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;

p is 0, 1, 2, or 3;

q is 0, 1, or 2; and wherein heteroaryl is an aromatic monocyclic or multicyclic ring system of 5 to 14 ring atoms in which one or more atoms in the ring system are nitrogen, oxygen, or sulfur;

or a pharmaceutically acceptable salt thereof.

2. The compound according to claim 1, wherein Q has an empirical formula $C_{7-10}H_{12-19}N_{1-2}$.

3. The compound according to claim 1, wherein Q is an azabicycloheptane, azabicyclooctane, or azabicyclononane.

4. The compound according to claim 3, wherein Q is quinuclidine.

5. The compound according to claim 1, wherein the saturated, bicyclic, heterocyclic amine is attached to the amide N of formula I in the (S) configuration.

6. The compound according to claim 1, wherein the saturated, bicyclic, heterocyclic amine is attached to the amide N of formula I in the (R) configuration.

7. The compound according to claim 1, wherein X is CH or $CR^2$.

8. The compound according to claim 1, wherein X is N.

9. The compound according to claim 1, wherein X is C=O.

10. The compound according to claim 1, wherein X is $SO_2$.

11. The compound according to claim 1, wherein Y is N or NH.

12. The compound according to claim 1, wherein Y is CH or $CR^2$.

13. The compound according to claim 1, wherein $R^2$ is substituted phenyl.

14. The compound according to claim 1, selected from the group consisting of:

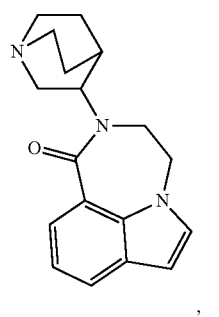
,
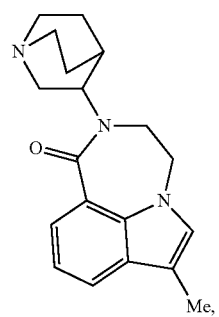
Me,

-continued

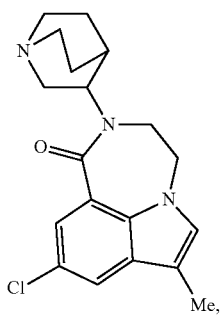
Me,
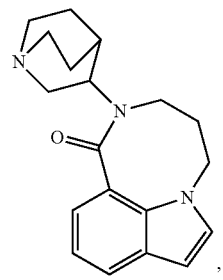
,

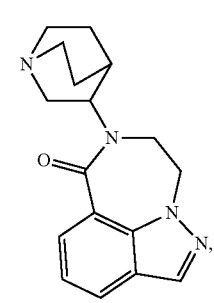
,
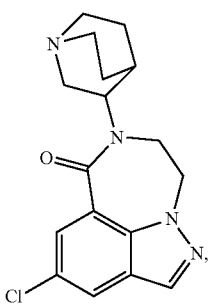
,

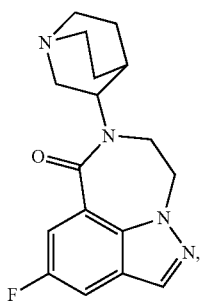
,
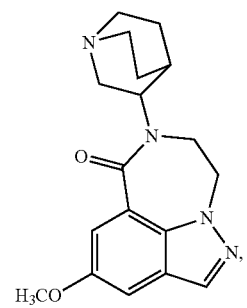
,

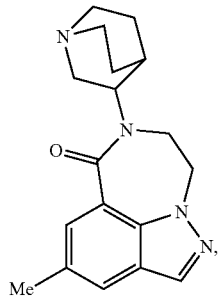
,
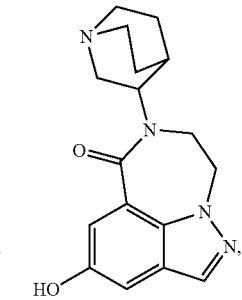
,

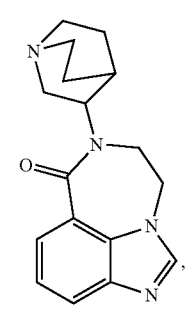
,
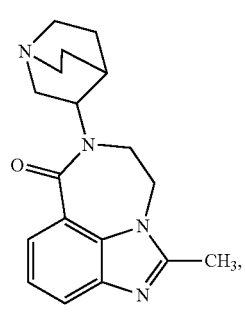
,

-continued

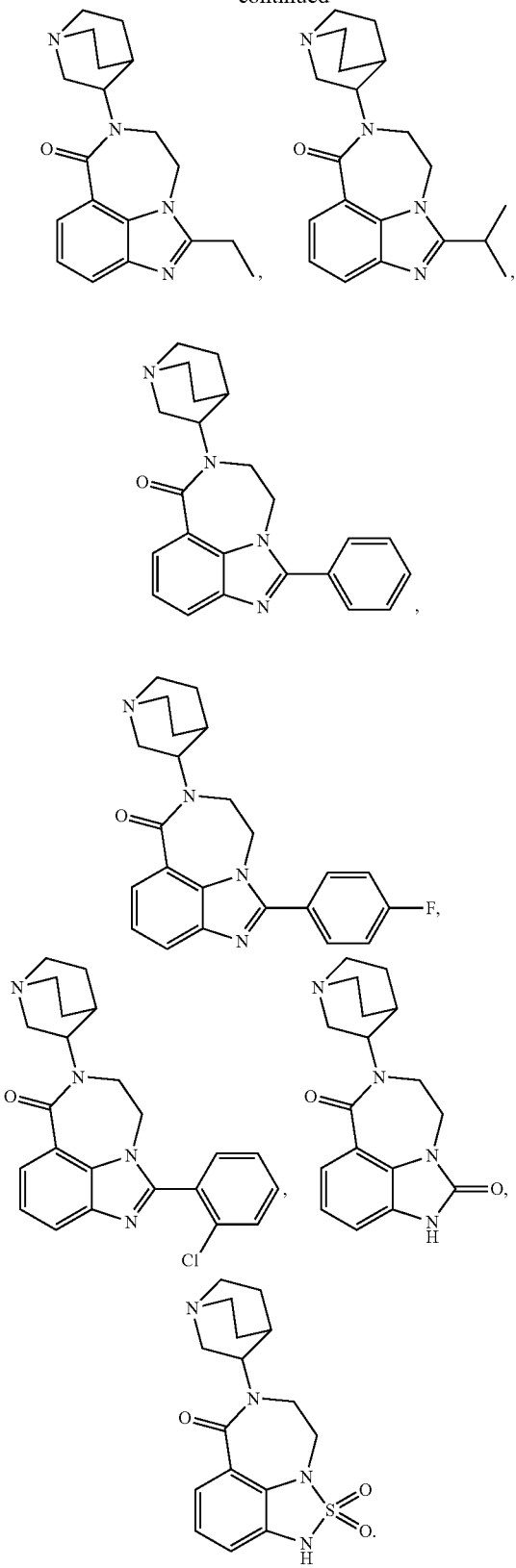

15. A pharmaceutical composition comprising a therapeutically effective amount of the compound according to claim 1 and a pharmaceutically acceptable carrier.

16. A compound of formula II:

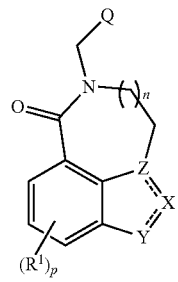

formula II wherein:
- - - - - represents an optional double bond;
Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, —OR$^7$, and —NR$^7$R$^8$;
X is CH, $CH_2$, CR$^2$, C(R$^2$)$_2$, N, NH, C=O, or $SO_2$;
Y is CH, $CH_2$, CR$^2$, C(R$^2$)$_2$, N, NH, NR$^3$, O, or C=O;
Z is C or N;
R$^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;
R$^2$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;
R$^3$ is selected from the group consisting of H, $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_3$-$C_6$ alkenyl, $C_3$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R[4] is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R[6], phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R[5] is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R[4] and R[5] are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

R[6] is $C_1$-$C_4$ alkyl, $C_1$-$C_4$ haloalkyl, or phenyl;

R[7] and R[8] are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R[6], phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 0, 1, or 2, with the provisos that: (1) when Z is N, then n is 1 or 2; and (2) when Z is C, then n is 0, 1, or 2;

p is 0, 1, 2, or 3;

q is 0, 1, or 2; and wherein heteroaryl is an aromatic monocyclic or multi-cyclic ring system of 5 to 14 ring atoms in which one or more atoms in the ring system are nitrogen, oxygen, or sulfur;

or a pharmaceutically acceptable salt thereof.

17. The compound according to claim 16, wherein Q has an empirical formula $C_{7-10}H_{12-19}N_{1-2}$.

18. The compound according to claim 16, wherein Q is an azabicycloheptane, azabicyclooctane, or azabicyclononane.

19. The compound according to claim 18, wherein Q is quinuclidine.

20. The compound according to claim 16, wherein the saturated, bicyclic, heterocyclic amine is attached to the amide N of formula II in the (S) configuration.

21. The compound according to claim 16, wherein the saturated, bicyclic, heterocyclic amine is attached to the amide N of formula II in the (R) configuration.

22. The compound according to claim 16, wherein X is CH or CR[2].

23. The compound according to claim 16, wherein X is N.

24. The compound according to claim 16, wherein X is C=O.

25. The compound according to claim 16, wherein X is $SO_2$.

26. The compound according to claim 16, wherein Y is N or NH.

27. The compound according to claim 16, wherein Y is CH or CR[2].

28. The compound according to claim 16, wherein Z is C.

29. The compound according to claim 16, wherein Z is N.

30. The compound according to claim 16, wherein R[2] is substituted phenyl.

31. The compound according to claim 16, selected from the group consisting of:

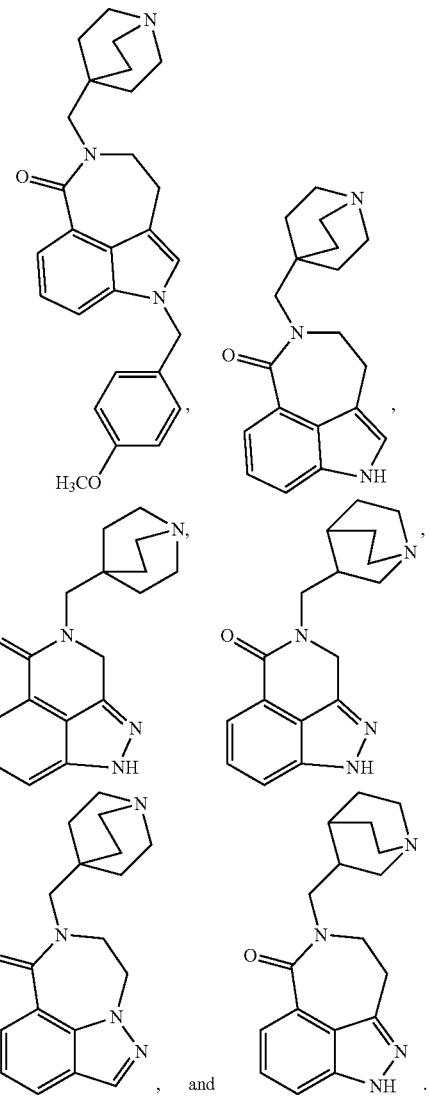

32. A pharmaceutical composition comprising a therapeutically effective amount of the compound according to claim 16 and a pharmaceutically acceptable carrier.

33. A process of preparing a product compound of formula Ia:

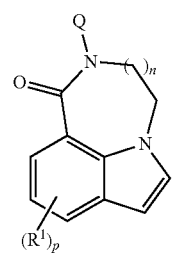

formula Ia wherein:

Q is a saturated, bicyclic, heterocyclic amine comprising at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —$OR^7$, and —$NR^7R^8$;

$R^1$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^4$ and $R^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;
p is 0, 1, 2, or 3; and
q is 0, 1, or 2;

wherein heteroaryl is an aromatic monocyclic or multicyclic ring system of 5 to 14 ring atoms in which one or more atoms in the ring system are nitrogen, oxygen, or sulfur;

said process comprising:
treating a first intermediate compound of formula III:

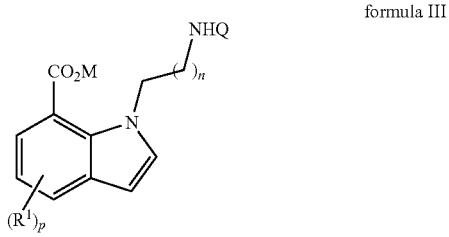

formula III wherein M is H or a counterion, under amide bond formation conditions effective to produce the product compound.

34. The process according to claim 33, wherein M is a counterion selected from the group consisting of $Li^+$ and $Na^+$.

35. A process of preparing a product compound of formula Ib:

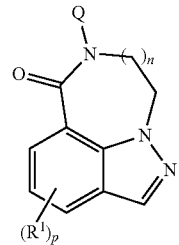

formula Ib wherein:
Q is a saturated, bicyclic, heterocyclic amine comprising at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —$OR^7$, and —$NR^7R^8$;

$R^1$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^4$ and $R^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;

p is 0, 1, 2, or 3; and q is 0, 1, or 2;

wherein heteroaryl is an aromatic monocyclic or multicyclic ring system of 5 to 14 ring atoms in which one or more atoms in the ring system are nitrogen, oxygen, or sulfur;

said process comprising:

treating a first intermediate compound of formula IV:

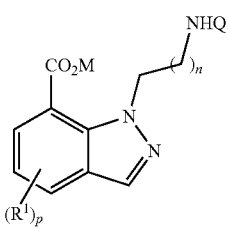

formula IV wherein M is H or a counterion, under amide bond formation conditions effective to produce the product compound.

36. The process according to claim 35, wherein M is a counterion selected from the group consisting of $Li^+$ and $Na^+$.

37. A process of preparing a product compound of formula Ic:

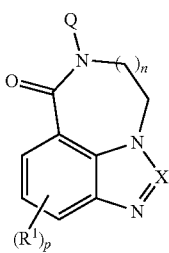

formula Ic wherein:

Q is a saturated, bicyclic, heterocyclic amine comprising at least two atoms between the amide nitrogen of the compound of formula I and any amine nitrogen of Q and wherein the saturated, bicyclic, heterocyclic amine is optionally substituted with from 1 to 3 substituents independently selected at each occurrence thereof from the group consisting of $C_1$-$C_3$ alkyl, halogen, —CN, —$OR^7$, and —$NR^7R^8$;

X is CH, $CH_2$, $CR^2$, $C(R^2)_2$, N, NH, C=O, or $SO_2$;

$R^1$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, and —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^2$ is individually selected at each location from the group consisting of H, halogen, —$OR^4$, —$NR^4R^5$, —$NR^4C(O)R^5$, —$NR^4C(O)_2R^5$, —$NR^5C(O)NR^5R^6$, —$S(O)_qR^5$, —CN, —$C(O)R^5$, —$C(O)NR^4R^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —$OR^7$, and —$NR^7R^8$, and phenyl which is optionally substituted 1-3 times with halogen, $C_1$-$C_4$ alkyl, $C_1$-$C_4$ haloalkyl, $C_1$-$C_4$ alkoxy, —CN, —$OR^7$, or —$NR^7R^8$;

$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^4$ and $R^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —$C(O)R^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;

p is 0, 1, 2, or 3; and q is 0, 1, or 2;

wherein heteroaryl is an aromatic monocyclic or multicyclic ring system of 5 to 14 ring atoms in which one or more atoms in the ring system are nitrogen, oxygen, or sulfur;

said process comprising:

treating a first intermediate compound of formula V:

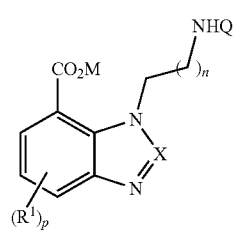

formula V wherein M is H or a counterion, under amide bond formation conditions effective to produce the product compound.

38. The process according to claim 37, wherein M is a counterion selected from the group consisting of Li+ and Na+.

39. A process of preparing a product compound of formula IIa:

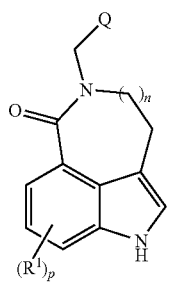

formula IIa wherein:
Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, —OR$^7$, and —NR$^7$R$^8$;

$R^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

$R^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

$R^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or $R^4$ and $R^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

$R^6$ is $C_1$-$C_4$ alkyl, $C_1$-$C_4$ haloalkyl, or phenyl;

$R^7$ and $R^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 0, 1, or 2;
p is 0, 1, 2, or 3; and
q is 0, 1, or 2;

wherein heteroaryl is an aromatic monocyclic or multicyclic ring system of 5 to 14 ring atoms in which one or more atoms in the ring system are nitrogen, oxygen, or sulfur;

said process comprising:
treating a first intermediate compound of formula VI:

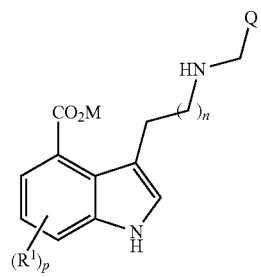

formula VI wherein M is H or a counterion, under amide bond formation conditions effective to produce the product compound.

40. The process according to claim 39, wherein M is a counterion selected from the group consisting of Li+ and Na+.

41. A process of preparing a product compound of formula IIb:

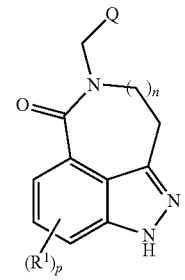

formula IIb wherein:
Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, —OR$^7$, and —NR$^7$R$^8$;

$R^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R$^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R$^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R$^4$ and R$^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

R$^6$ is $C_1$-$C_4$ alkyl, $C_1$-$C_4$ haloalkyl, or phenyl;

R$^7$ and R$^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 0, 1, or 2;

p is 0, 1, 2, or 3; and q is 0, 1, or 2;

wherein heteroaryl is an aromatic monocyclic or multicyclic ring system of 5 to 14 ring atoms in which one or more atoms in the ring system are nitrogen, oxygen, or sulfur;

said process comprising:

treating a first intermediate compound of formula VII:

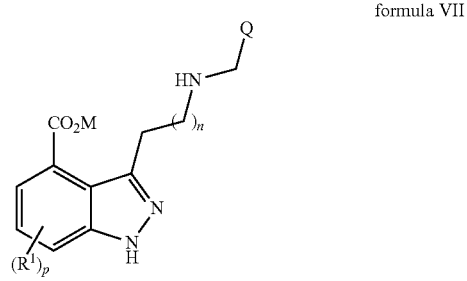

formula VII wherein M is H or a counterion, under amide bond formation conditions effective to produce the product compound.

42. The process according to claim 41, wherein M is a counterion selected from the group consisting of Li$^+$ and Na$^+$.

43. A process of preparing a product compound of formula IIc:

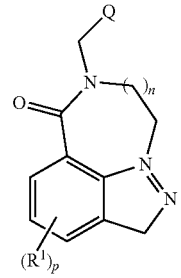

formula IIc wherein:

Q is a saturated, bicyclic, heterocyclic amine, wherein the saturated, bicyclic, heterocyclic amine is optionally substituted with from 1 to 3 substituents independently selected at each occurrence thereof from the group consisting of $C_1$-$C_3$ alkyl, halogen, —CN, —OR$^7$, and —NR$^7$R$^8$;

R$^1$ is individually selected at each location from the group consisting of H, halogen, —OR$^4$, —NR$^4$R$^5$, —NR$^4$C(O)R$^5$, —NR$^4$C(O)$_2$R$^5$, —NR$^5$C(O)NR$^5$R$^6$, —S(O)$_q$R$^5$, —CN, —C(O)R$^5$, —C(O)NR$^4$R$^5$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl, wherein each of $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl, and heteroaryl is optionally substituted with from 1 to 3 substituents independently selected at each occurrence thereof from $C_1$-$C_3$ alkyl, halogen, —CN, —OR$^7$, —NR$^7$R$^8$, and phenyl which is optionally substituted 1-3 times with halogen, $C_1$-$C_4$ alkyl, $C_1$-$C_4$ haloalkyl, $C_1$-$C_4$ alkoxy, —CN, —OR$^7$, or —NR$^7$R$^8$;

R$^4$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy;

R$^5$ is H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, phenyl, or benzyl, wherein phenyl or benzyl is optionally substituted 1 to 3 times with halogen, cyano, $C_1$-$C_4$ alkyl, $C_1$-$C_4$ haloalkyl, or $C_1$-$C_4$ alkoxy; or R$^4$ and R$^5$ are taken together with the nitrogen to which they are attached to form a five- to seven-membered heterocyclic ring, which comprises from 1 to 2 heteroatoms selected from the group consisting of nitrogen, oxygen, and sulfur, and is optionally substituted from 1 to 4 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

R$^6$ is $C_1$-$C_4$ alkyl, $C_1$-$C_4$ haloalkyl, or phenyl;

R$^7$ and R$^8$ are each independently H, $C_1$-$C_4$ alkyl, $C_1$-$C_4$ haloalkyl, $C_1$-$C_4$ alkoxyalkyl, $C_3$-$C_6$ cycloalkyl, $C_4$-$C_7$ cycloalkylalkyl, —C(O)R$^6$, phenyl, or benzyl, wherein phenyl or benzyl is optionally substituted from 1 to 3 times with a substituent selected independently at each occurrence thereof from the group consisting of halogen, cyano, $C_1$-$C_4$ alkyl, $C_1$-$C_4$ haloalkyl, and $C_1$-$C_4$ alkoxy;

n is 1 or 2;
p is 0, 1, 2, or 3; and
q is 0, 1, or 2;
wherein heteroaryl is an aromatic monocyclic or multi-cyclic ring system of 5 to 14 ring atoms in which one or more atoms in the ring system are nitrogen, oxygen, or sulfur;
said process comprising:
treating a first intermediate compound of formula VIII:

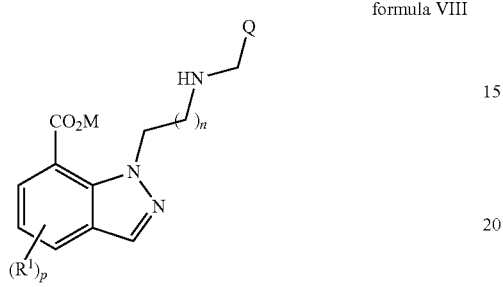

formula VIII wherein M is H or a counterion, under amide bond formation conditions effective to produce the product compound.

44. The process according to claim 43, wherein M is a counterion selected from the group consisting of $Li^+$ and $Na^+$.

* * * * *

UNITED STATES PATENT AND TRADEMARK OFFICE
CERTIFICATE OF CORRECTION

PATENT NO. : 8,710,046 B2
APPLICATION NO. : 13/384050
DATED : April 29, 2014
INVENTOR(S) : Peter R. Guzzo, David D. Manning and William Earley Page 1 of 1

It is certified that error appears in the above-identified patent and that said Letters Patent is hereby corrected as shown below:

In the Claims

In claim 5, at col. 93, line 30, delete "(5)" and insert in its place --(*S*)--.

In claim 43, at col. 106, lines 5-15, delete

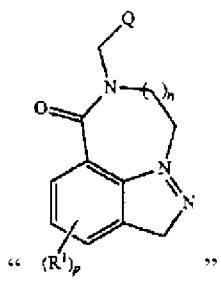

"                "

and replace with

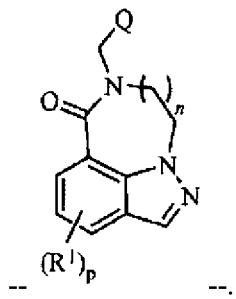

--              --.

Signed and Sealed this
Twenty-ninth Day of July, 2014

Michelle K. Lee
*Deputy Director of the United States Patent and Trademark Office*